(12) United States Patent
Svendsen et al.

(10) Patent No.: US 12,161,676 B2
(45) Date of Patent: Dec. 10, 2024

(54) METHODS OF USE OF ISLET CELLS

(71) Applicant: CEDARS-SINAI MEDICAL CENTER, Los Angeles, CA (US)

(72) Inventors: Clive Svendsen, Pacific Palisades, CA (US); Dhruv Sareen, Porter Ranch, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1087 days.

(21) Appl. No.: 16/982,691

(22) PCT Filed: Mar. 22, 2019

(86) PCT No.: PCT/US2019/023749
§ 371 (c)(1),
(2) Date: Sep. 21, 2020

(87) PCT Pub. No.: WO2019/183597
PCT Pub. Date: Sep. 26, 2019

(65) Prior Publication Data
US 2021/0000880 A1    Jan. 7, 2021

Related U.S. Application Data

(60) Provisional application No. 62/647,548, filed on Mar. 23, 2018.

(51) Int. Cl.
*A61K 35/39* (2015.01)
*C12N 5/071* (2010.01)

(52) U.S. Cl.
CPC ............ *A61K 35/39* (2013.01); *C12N 5/0678* (2013.01); *C12N 2501/115* (2013.01); *C12N 2501/119* (2013.01); *C12N 2501/15* (2013.01); *C12N 2501/155* (2013.01); *C12N 2501/165* (2013.01); *C12N 2501/999* (2013.01); *C12N 2506/45* (2013.01)

(58) Field of Classification Search
CPC .................. A61K 35/39; C12N 5/0678; C12N 2501/115; C12N 2501/119; C12N 2501/15; C12N 2501/155; C12N 2501/165; C12N 2501/999; C12N 2506/45

See application file for complete search history.

(56) References Cited

U.S. PATENT DOCUMENTS

| | | |
|---|---|---|
| 6,300,080 B1 | 10/2001 | Brenner et al. |
| 7,989,197 B2 | 8/2011 | Yoo et al. |
| 8,647,861 B2 | 2/2014 | Ingber et al. |
| 9,790,470 B2 | 10/2017 | Vallier et al. |
| 10,174,289 B2 | 1/2019 | Wells et al. |
| 11,326,149 B2 | 5/2022 | Kerns et al. |
| 2004/0247571 A1 | 12/2004 | Meijer et al. |
| 2007/0077649 A1 | 4/2007 | Sammak et al. |
| 2007/0128722 A1 | 6/2007 | Lin |
| 2007/0281353 A1 | 12/2007 | Vacanti et al. |
| 2008/0044847 A1 | 2/2008 | Shusta et al. |
| 2008/0132445 A1 | 6/2008 | Ormandy et al. |
| 2008/0305086 A1 | 12/2008 | Poole |
| 2009/0075374 A1 | 3/2009 | Palecek et al. |
| 2009/0123383 A1 | 5/2009 | Frangioni |
| 2009/0214649 A1 | 8/2009 | Gazit et al. |
| 2009/0258337 A1 | 10/2009 | Yagi |
| 2009/0317852 A1 | 12/2009 | Parker et al. |
| 2009/0324559 A1 | 12/2009 | Sakurada et al. |
| 2010/0136690 A1 | 6/2010 | Sundstorm et al. |
| 2011/0064700 A1 | 3/2011 | Cardozo et al. |
| 2011/0097796 A1 | 4/2011 | Loa |
| 2011/0111499 A1 | 5/2011 | Torihashi |
| 2011/0245307 A1 | 10/2011 | Alkon |
| 2011/0250585 A1 | 10/2011 | Ingber et al. |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |

(Continued)

FOREIGN PATENT DOCUMENTS

| | | |
|---|---|---|
| AU | 2015204375 A1 | 8/2015 |
| AU | 2016341880 A1 | 5/2018 |

(Continued)

OTHER PUBLICATIONS

Kim, H., and Lee M., "β-Cell regeneration through the transdifferentiation of pancreatic cells: Pancreatic progenitor cells in the pancreas," Journal of Diabetes Investigation 7(3): 286-296. doi: 10.1111/jdi.12475. (Year: 2016).*

Clayton, Z. E., et al., "Generating induced pluripotent stem cell derived endothelial cells and induced endothelial cells for cardiovascular disease modelling and therapeutic angiogenesis," International Journal of Cardiology 197: 116-122. doi: 10.1016/j.ijcard.2015.06.038. (Year: 2015).*

International Search Report and Written Opinion for PCT/US2018/015318 May 2, 2018, 16 pages.

International Search Report and Written Opinion for PCT/US2018/024198 dated Aug. 13, 2018, 15 pages.

(Continued)

*Primary Examiner* — Tracy Vivlemore
*Assistant Examiner* — Eric J Rogers
(74) *Attorney, Agent, or Firm* — Nixon Peabody LLP

(57) ABSTRACT

Type 2 diabetes (T2D) is a clinical syndrome caused by insufficient insulin secretion for insulin requirements. described herein are compositions and methods for microphysiological MPS models of disease (MODs) for diabetes. These platforms allow one to compare the effect of chronic β-cell stimulation in the presence and absence of patient specific immune cells in IPSC-derived islets from each group. Additionally, one can reproduce the T2D β-cell phenotype, using islets-on-chips will also be exposed to gluco-lipotoxicity. Likewise, skeletal muscle-on-chips are exposed to patient specific activated immune cells, variable motor neuron innervation and lipids characteristic of T2D.

15 Claims, 62 Drawing Sheets

(56) References Cited

U.S. PATENT DOCUMENTS

| | | |
|---|---|---|
| 2012/0211373 A1 | 8/2012 | El-Sayed et al. |
| 2013/0137130 A1 | 5/2013 | Wells et al. |
| 2013/0224857 A1 | 8/2013 | Blak et al. |
| 2013/0280802 A1 | 10/2013 | Schulz et al. |
| 2013/0288969 A1 | 10/2013 | Scadden |
| 2014/0038279 A1 | 2/2014 | Ingber et al. |
| 2014/0065660 A1 | 3/2014 | Kim et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2014/0342445 A1 | 11/2014 | Ingber et al. |
| 2015/0017674 A1 | 1/2015 | Christensen et al. |
| 2015/0023928 A1 | 1/2015 | Hassiotou |
| 2015/0037320 A1 | 2/2015 | Mcgrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0252328 A1 | 9/2015 | Woodruff et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0145642 A1 | 5/2016 | Cui et al. |
| 2016/0152950 A1 | 6/2016 | Zhang et al. |
| 2016/0175401 A1 | 6/2016 | Spiegelman et al. |
| 2017/0107498 A1 | 4/2017 | Sareen et al. |
| 2017/0226478 A1 | 8/2017 | Kerns et al. |
| 2017/0240866 A1 | 8/2017 | Wells et al. |
| 2017/0253856 A1 | 9/2017 | Douvaras et al. |
| 2017/0283772 A1 | 10/2017 | Qian et al. |
| 2017/0292116 A1 | 10/2017 | Erlls et al. |
| 2017/0313976 A1 | 11/2017 | Kuwahara et al. |
| 2018/0021383 A1 | 1/2018 | George et al. |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0000267 A1 | 1/2020 | Zuidervaart et al. |
| 2020/0002671 A1 | 1/2020 | Qu et al. |
| 2020/0032215 A1 | 1/2020 | Svendsen et al. |
| 2020/0071673 A1 | 3/2020 | Sareen et al. |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0024886 A1 | 1/2021 | Laperle et al. |
| 2021/0033628 A1 | 2/2021 | Laperle et al. |
| 2021/0130774 A1 | 5/2021 | Sances et al. |
| 2023/0159896 A1 | 5/2023 | Sharma et al. |
| 2024/0067933 A1 | 2/2024 | Laperle et al. |
| 2024/0076629 A1 | 3/2024 | Laperle et al. |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3008168 A1 | 4/2016 |
| EP | 3031908 A1 | 6/2016 |
| EP | 3365424 | 8/2018 |
| EP | 3411470 A2 | 12/2018 |
| EP | 3411472 A1 | 12/2018 |
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B2 | 7/2021 |
| JP | 2003-511346 | 9/2000 |
| JP | 2014-171434 | 9/2014 |
| JP | 2014-171434 A | 9/2014 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A | 8/2021 |
| JP | 2021-523700 A | 9/2021 |
| JP | 2021-523888 A | 9/2021 |
| KR | 20180069882 A | 6/2018 |
| SG | 11201803143Y A | 5/2018 |
| SG | 11201901621V A | 3/2019 |
| SG | 11201901628X A | 3/2019 |
| SG | 11201908358P A | 10/2019 |
| SG | 11201908359U A | 10/2019 |
| WO | 2000053218 | 9/2000 |
| WO | WO 2005/021720 A2 | 3/2005 |
| WO | WO 2010009307 A2 | 1/2010 |
| WO | WO 2010/108005 A2 | 9/2010 |
| WO | WO 2011109440 A1 | 9/2011 |
| WO | 2012/100084 A1 | 7/2012 |
| WO | WO 2012/118799 A2 | 9/2012 |
| WO | 2013/056216 A1 | 4/2013 |
| WO | 2013/071282 A1 | 5/2013 |
| WO | WO 2013/065763 A1 | 5/2013 |
| WO | 2013/086486 A1 | 6/2013 |
| WO | WO2013106677 A1 | 7/2013 |
| WO | 2013/184193 A1 | 12/2013 |
| WO | WO 2014/172682 A1 | 10/2014 |
| WO | WO 2014/176606 A1 | 10/2014 |
| WO | WO 2014159356 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | WO 2015/138032 A2 | 9/2015 |
| WO | WO 2015/138034 A2 | 9/2015 |
| WO | WO2015143342 A1 | 9/2015 |
| WO | WO 2015/163823 A1 | 10/2015 |
| WO | WO 2015153451 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | WO 2016061464 A1 | 4/2016 |
| WO | WO 2016063985 A1 | 4/2016 |
| WO | WO 2016/086040 A1 | 6/2016 |
| WO | WO 2016/093222 A | 6/2016 |
| WO | 2016/141137 A1 | 9/2016 |
| WO | WO 2016162747 A2 | 10/2016 |

(56) References Cited

FOREIGN PATENT DOCUMENTS

| | | |
|---|---|---|
| WO | WO 2016183252 A1 | 11/2016 |
| WO | WO 2017/035119 A1 | 3/2017 |
| WO | WO 2017/070224 A1 | 4/2017 |
| WO | WO 2017075271 A1 | 5/2017 |
| WO | WO 2017078807 A1 | 5/2017 |
| WO | 2017/112455 A1 | 6/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | 2017200486 A1 | 11/2017 |
| WO | 2017/219000 A1 | 12/2017 |
| WO | 2018/035214 A1 | 2/2018 |
| WO | WO 2018/044885 A1 | 3/2018 |
| WO | WO 2018/044934 A1 | 3/2018 |
| WO | 2018/140647 A1 | 8/2018 |
| WO | 2018/176001 A1 | 9/2018 |
| WO | WO 2018/170139 A1 | 9/2018 |
| WO | WO 2018/170180 A1 | 9/2018 |
| WO | WO 2018/213773 A1 | 11/2018 |
| WO | 2019/122291 A2 | 6/2019 |
| WO | 2019/178550 A1 | 9/2019 |
| WO | 2019183597 A1 | 9/2019 |
| WO | WO-2019169351 A1 * | 9/2019 ............ A61K 35/39 |
| WO | WO 2019/195798 A1 | 10/2019 |
| WO | WO 2019195800 A1 | 10/2019 |
| WO | WO 2019212690 A1 | 11/2019 |
| WO | WO 2019212691 A1 | 11/2019 |
| WO | 2021/081229 A1 | 4/2021 |
| WO | 2021/081237 A1 | 4/2021 |
| WO | 2021222724 A1 | 11/2021 |

OTHER PUBLICATIONS

International Search Report and Written Opinion for PCT/US2020/056896 dated Oct. 22, 2020, 11 pages.
International Search Report and Written Opinion for PCT/US2020/056906 dated Mar. 16, 2021, 13 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLoS One, 2014, 9(1), 14 pages.
Badger et al., Parkinson's disease in a dish – Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrsen et al. Supportive angiogenic and osteogenic differentiation of mesenchymal stromal cells and endothelial cells in monolayer and co-cultures. International Journal of Oral Science (2016) 8, 223-230 (Year: 2016).
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.

Farrelly et al., Extracellular matrix regulates apoptosis in mammary epithelium through a control on insulin signaling, The Journal of Cell Biology, 1999, 144(6):1337-1347.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hiens et al., BMP4 and PTHrP interact to stimulate ductal outgrowth during embryonic mammary development and to inhibit hair follicle induction, Development, 2017, 134:1221-1230.
Ichida et al., Probing disorders of the nervous system using reprogramming approaches, The EMBO Journal / European Molecular Biology Organization, 2015, vol. 34, No. 11, pp. 1456-1477.
Kessler et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. PLoS One 9(3): e92427. p. 1-9 (Year: 2014).
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Levanon, et al., Primary ex vivo cultures of human fallopian tube epithelium as a model for serous ovarian carcinogenesis, Oncogene, 2010, 29(8):1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).
O'Neill et al., Genetic disorders coupled to ROS deficiency, Redox Biology, 6: 135-156. (Year: 2015).
Qu et al., Differentiation of human induced pluripotent stem cells to mammary-like organoids, Stem Cell Reports, 2017, 8(2):205-215.
Rey, et al., Chapter 7, Sexual Differentiation, 2016 [online]. [Retrieved on Sep. 19, 2019]. Retrieved from the Internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCI [alpha] Trans, Cell, Elsevier, 2013, vol. 155, No. 6, pp. 1351-1364.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Simeone et al., The Otx Family, Pattern Formation and Development Mechanisms, 2002, vol. 12, pp. 409-415.
Sun et al., Role of Bone Morphogenetic Protein-2 in Osteogenic Differentiation of MesenChymal Stem Cells, Molecular Medicine Reports, 2015, vol. 12, pp. 4230-4237.
Vogel et al., Co-culture of human induced pluripotent stem cells 9iPSCs) with human fallopian tube epithelium (FTE) Induces Pax8 and CK7 expression: Initial steps in modeling fallopian tube epithelium to study serous carcinogenesis; Gynecologic Oncology, 2015 137(1):206.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
Zhou et al., Rapid and efficient generation of transgene-free iPSC from a small volume of cryopreserved blood, Stem Cell Reviews and Reports 11: 652-665. (Year: 2015).
EP 19771249.0 Partial Supplemental European Search Report dated Nov. 8, 2011, 15 pages.

(56) References Cited

OTHER PUBLICATIONS

EP 18802136.4 Examination Report dated Oct. 14, 2021, 8 pages.
Abbott et al., Structure and function of the blood-brain barrier, Neurobiology of Desease, 2010 27:13-25.
Abbott et al., Structure and function of the blood-brain barrier, Pharm Tox BBB: 1-3, Feb. 2010, Conf. Abstract.
Demers et al., Development-on-Chip: in vitro Neutral Tube Patterning with a Microfluidic Device, Development, 2016, vol. 143(11), pp. 1884-1892.
Kauffman et al., Alternative functional in vitro models of human intestinal epithelia, frontiers in Pharmacology, Jul. 2013, vol. 4, Article 79, 18 pages.
Kelamangalath et al. k-Opioid receptor inhibition of calcium oscillations in spinal cord neurons,, Molecular Pharmacology, 2011, 79:1061-1071.
Kwasny et al., Static biofilm cultures of gram-positive pathogens grown in a microtiter format used for anti-biofilm drug discovery, Current Protocols in Pharmacology, 2010, 13A.8.1-13A.8.23.
Loo et al., An Arduous Journey from Human Pluripotent Stem Cells to Functional Pancreatic Beta Cells, Diabetes Obes Metab., 2018, vol. 20(3), pp. 3-13.
McGaugh et al., Efficient Differentiation of Pluripotent Stem Cells to NKX6-1 + Pancreating Progenitors, Journal of Visualized Experiments, 2017, vol. 121, pp. 1-5.
Naik et al., In vitro blood-brain models: Current and perspective technologies, J. Phar Sci., 2012, 1014(4):1337-1354.
Perry et al., The Neuromuscular junction: Structure and function, downloaded from the internet (Neuromuscular junction: Parts, structure and steps/Kenhub>, pp. 1-6, downloaded Feb. 25, 2021.
Polydimethylsiloxane—Wikipedia, dowloaded on Feb. 24, 21 <Silicon dioxide—Wikipedia>, pp. 1-11.
Ryan et al., Progranulin is expressed within motor neurons and promotes neuronal cell survival, BMC Neuroscience, 2009, 10:130, pp. 1-22.
Sances et al., Modeling ALS with Motor Neurons Derived from Human Induced Pluripotent Stem Cells, Nature Neuroscience , 2016, vol. 19, pp. 542-553.
Santaguida et al., Side by Side Comparison Between Dynamic Versus Static Models of Blood-Brain-Barrier in vitro: A Permeability Study, Brain Research, 2006, vol. 1109(1), pp. 1-13.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocarboxylate Transporter 8 (MCT8) Gene, 2005, AJHG, vol. 77(1), pp. 41-53.
Silicon dioxide—Wikipedia, downloaded on Feb. 24, 2021 <silicon dioxide—Wikipedia> pp. 1-20.
Southam et al., Microfluidic primary culture model of the lower motor neuron-neuromuscular junction circuit, J Neurosc Meth 2013, 218:164-169.
Southam et al., A Novel in vitro Primary Culture Model of the Lower Motor Neuron—Nueromuscular Junction Circuit, Microfludic and Compartmentalized Platforms for Neurobiological Research, Humana Press, 2015, pp. 181-193, abstract only.
Uzei et al., Microfluidic Device for the Formation of Optically Excitable, Three-Dimensional, Compartmentalized Motor Units, Science Advances, 2016, pp. e1501429.
Wang et al., Microfluidics: A new cosset for neurobiology, Lab Chip, 2009, 9:644-652.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Yang et al., From the vascular microenvironment to neurogenesis, Brain Res Bull. Jan. 15, 2011; 84(1):1-7.
Arendt et al., Form and Function: how Estrogen and Progesterone Regulate the Mammary Epithelial Hierarchy, J. Mammary Gland Biol Neoplasia, 2015, 20:9-25.
Qiao et al, AP2y regulates neural and epiderman development downstream of the BMP pathway at early stages of ectodermal patterning, Cell Research, 2012, 22:1546-1561.
Lin et al., Embryoid body formation from human pluripotent stem cells in chemically defined E8 media, StemBook, ed, Jun. 1, 2014.
JP Reasons for Rejection—2020-560893 dated Feb. 6, 2023, 9 pages.
Matsumoto et al., Functional neurons generated from T Cell-derived induced pluripotent stem cells for neurological disease modeling, 2016, 6:422-435.
Moors et al., Therapeutic potential of autophagy-enhancing agents in Parkinson's disease, Molecular Neurodegeneration, 2017, 12:11, p. 1-18.
Okita et al., An efficient nonviral method to generate integration-free human-induced pluripotent stem cells from cord blood and peripheral blood cells, Stem Cells 2013, 31:458-466.
Kondo et al., iPSC-Based compound screening and in vitro trials identify a synergistic anti-amyloid B combination for Alzheimer's Disease, Cell Reports 2017, 21:2304-2312.
Hojo et al., Development of high-throughput screening system for osteogenic drugs using a cell-based sensor, Biochemical and Biophysical Research Communiatins 376(2):375-379, 2008.
Hayes et al., Strategies to generate induced pluripotentstem cells, Methods in Molecular Biology 1029: 77-92. doi: 10.1007/978-1-62703-478-4_6 (Year: 2013).
Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.
ISR and WO for PCT/US2021/030128 mailed Aug. 25, 2021, 10 pages.
Essential 8 medium C037161 Essential8System Brochure (thermofisher.com), downloaded on Aug. 24, 2022, pp. 1-2.
Ionescu et al., Compartmental microfluidic system for studying muscle-neuron communication and neuromuscular junction maintenance, 2016 European Journal.
DMEM F-12 Formulation, pp. 1-5, 2022.
Mehta et al., The actions of retinoids on cellular growth correlate with their actions on gap junctional communication, JCB 108, 1053-1065, 1989.
Munera et al., Differentiation of Human Pluripotent Stem Cells into Colonic Organoids via Transient Activation of BMP Signaling, Cell Stem Cell, 21, 51-64, 2017.
EP 19782199.4 Partial Supplementary Search Report dated Nov. 30, 2021, 15 pages.
EP 19796470.3 European Extended Search Report dated Dec. 10, 2021, 11 pages.
Burkhardt et al., A Cellular Model for Sporadic ALS using Patient-Derived Induced Pluripotent Stem Cells, Molecular and Cellular Neuroscience, 2013, vol. 56, pp. 355-364.
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.
Lenzi et al., Differentiation of Control and ALS Mutant Human iPSCs into Functional Skeletal Muscle Cells, a Tool for the Study of Neuromuscolar Diseases, Stem Cell Research, 2016, vol. 17, pp. 140-147.
Tian et al., Salvianolic Acid B, An Antioxidant from Saliva Miltiorrhiza, prevents 6-hydroxydopamine Induced Apoptosis in SH-SY5Y Cells, The International Science Journal of Biochemistry & Cell Biology, 2008, vol. 40, pp. 409-422.
Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.
International Search Report and Written Opinion of PCT Application No. PCT/US2017/013250, Dated Mar. 31, 2017, 12 Pages.
International Search Report and Written Opinion of PCT Application No. PCT/US2016/057724, Dated Jan. 9, 2017, 17 Pages.
International Search Report and Written Opinion of PCT/US2017/016098, Dated Jun. 22, 2017, 14 Pages.
International Search Report and Written Opinion of PCT/US2017/016079, Dated Jul. 25, 2017, 26 Pages.

(56) References Cited

OTHER PUBLICATIONS

International Search Report and Written Opinion of PCT/US2017/049193, Dated Nov. 6, 2017, 9 Pages.
International Search Report and Written Opinion of PCT/US2017/049115, Dated Nov. 28, 2017, 11 Pages.
International Search Report and Written Opinion of PCT/US2018/022511, Dated Jul. 26, 2018, 11 Pages.
International Search Report and Written Opinion of PCT/US2018/033498, Dated Aug. 9, 2018, 9 Pages.
International Search Report and Written Opinion for PCT/US2018/022455 dated Aug. 23, 2018, 13 pages.
International Preliminary Report on Patentability for PCT/US2016/057724 dated Apr. 24, 2018, 15 pages.
International Preliminary Report on Patentability for PCT/US2017/013250 dated Jul. 17, 2018, 7 pages.
International Preliminary Report on Patentability for PCT/US2017/016098 dated Aug. 7, 2018, 10 pages.
International Preliminary Report on Patentability for PCT/US2017/016079 dated Aug. 7, 2018, 21 pages.
International Preliminary Report on Patentability for PCT/US2018/022511, dated Sep. 17, 2019, 8 pages.
International Preliminary Report on Patentability for PCT/US2018/022455 dated Aug. 23, 2018, 9 pages.
International Preliminary Report on Patentability for PCT/US2018/033498 dated Nov. 19, 2019, 8 pages.
International Preliminary Report on Patentability for PCT/US2017/049193 dated Mar. 5, 2019, 8 pages.
International Preliminary Report on Patentability for PCT/US2017/049115 dated Mar. 5, 2019, 8 pages.
International Search Report and Written Opinion of PCT/US2019/26178, Dated Jun. 11, 2019, 14 Pages.
AU 2016341880 Examination Report dated Jan. 15, 2020, 5 pages.
AU 2017214468 Examination Report dated Dec. 10, 2019, 5 pages.
CA 3034614 Examination Report dated Jul. 5, 2019, 5 pages.
EP 16858141.1 Extended Search Report dated Mar. 15, 2019, 10 pages.
EP 17748100.9 European Partial Supplementary Search Report dated Sep. 18, 2019, 15 pages.
EP 17748100.9 European Extended Search Report dated Dec. 20, 2019, 12 pages.
EP 17748084.5 European Extended Search Report dated Sep. 10, 2019.
EP 17847396.3 European Extended Search Report dated, Jan. 28, 2020, 11 pages.
EP17847365.8 European Extended Search Report dated Jan. 21, 2020, 11 pages.
GB1811716.8 Examination Report dated Feb. 12, 2020, 6 pages.
GB 1903007.1 Search Report dated Apr. 1, 2019, 8 pages.
SG 11201803143Y Search Report dated Jul. 15, 2019, 3 pages.
Action Potential, Wikipedia, pp. 1-29 Downloaded on Apr. 28, 2019, https://en.wikipedia.org/wiki/Action_potential.
Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.
Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.
Barrett et al., Reliable Generation of Induced Pluripotent Stem Cells from Human Pymphoblastoid Cell Lines, 2014, Stem Cells Translational Medicine, vol. 3, pp. 1429-1434.
Ben-Zvi et al., Modeling Human Nutrition Using Human Embryonic Stem Cells, Cell, 2015, vol. 161(1), pp. 12-17.
Bhatia et al., Microfluidic Organs-on-Chips, Nature Biotechnology, 2014, vol. 32(8), pp. 760-772.
Booth, Ross Hunter, A Microfluidic in Vitro Model of the Blood-Brain Barrier, Dissertation, 2014, pp. 1-177.
Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.
Jang et al., JAK-STAT Pathway and Myogenic Differentiation, JAKSTAT, 2013, vol. 2(2), pp. e23282-1 to e-23282-6.
Kilic et al., Brain-on-a-Chip Model Enables Analysis of Human Neuronal Differentiation and Chemotaxis, 2016, Lab on a Chip, vol. 16(21), pp. 4152-4162.
Kim et al., Human Gut-on-a-Chip Inhabited by a Microbial Flora that Experiences Intestinal Peristalsis-Like Motions and Flow, Lab on a Chip, 2012, vol. 12(12). pp. 2165.

(56) References Cited

OTHER PUBLICATIONS

Kim et al., Gut-on-a-Chip Microenvironment Induces Human Intestinal Cells to Undergo Villus Differentiation, Integrative Biology, 2013, vol. 5(9), p. 1130-1140.
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Lenner, J., Fat Cells More Easily Programmed into iPS Cells, 2009, pp. 1-2.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.
Lippmann et al., A Retinoic Acid-Enhanced, Multicellular Human Blood-Brain Barrier Model Derived from Stem Cell Sources, Scientific Reports, vol. 4(1), 2014, pp. 1-10.
Lippmann et al., Chemically Defined Differentiation of Human Pluripotent Stem Cells to Hindbrain and Spinal Cord Neural Stem Cells with Defined Regional Identifies, 2015, Protocol Exchange.
Martin et al., Laparoscopic Colorectal Resection in the Obese Patient, 2011, Clinics in Colon and Rectal Surgery, vol. 24(4), pp. 263-273.
Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.
Medical Dictionary—MYOTUBE, Downloaded on Jul. 8, 2018, https://medical-dictionary.thefreedictionary.com/myotube, p. 1.
Murphy et al., Scaffolds for 3D in vitro Culture of Neural Lineage Cells, Acta Biomaterialia, 2017, vol. 54, pp. 1-20.
Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.
Niego et al., Improved Method for the Preparation of a Human Cell-based, Contact Model of the Blood-Brain Barrier, 2013, J. Vis. Exp., vol. 81(e50934), pp. 1-9.
Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and Adipose Tissue-Derived Mesenchymal Stem Cells under Mechanical Stimulation, PLoOS One, 2012, vol. 7(9), pp. 1-12.
Polini et al., Organs-on-a-Chip: A New Tool for Drug Discovery, Expert Opinion on Drug Discovery, 2014, vol. 9(4), pp. 335-352.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.
Rajesh et al., Human Lymphoblastoid B-Cell Lines Reprogrammed to EBV-FREE Induced Pluripotent Stem Cells, 2011, Blood, vol. 118(7), pp. 1797-1800.
Rhee et al., Patterned Cell Culture Inside Microfluidic Devices, Lab Chip, 2005, vol. 5(1), pp. 102-107.
Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Shimojo et al., Rapid, Efficient and Simple Motor Neuron Differentiation from Human Pluripotent Stem Cells, Molecular Brain, 2015, vol. 8(1), pp. 1-15.
Shimuzu et al., Microfluidic Devices for Construction of Contractile Skeletal Muscle Microtissues, J. Biosci. Bioeng., 2015, vol. 119, pp. 212-216.
Soria-Valles et al., NF-kB Activation Impairs Somatic Cell Reprogramming in Ageing, 2015, Nat. Cell Biol., vol. 17(8), pp. 1004-1013.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.
Uzel et al., New Microfluidic Chip Replicates Muscle-Nerve Connection, 2016, Science Daily, pp. 1-4.
Vatine et al., Human iPSC-Derived Blood-Brain Barrier Chips Enable Disease Modeling and Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Watson et al., Modelling the Endothelial Blood—CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Zilio et al., Universal Hydrophilic Coating of Thermoplastic Polymers Currently Used in Microfluidics, 2014, Biomed. Microdevices, vol. 16(1), pp. 107-114.
Fridley et al., Hydrodynamic modulation of pluripotent stem cells, Stem cell research & therapy,2012, vol. 45.
Zhang et al., Patient-specific 3D microfluidic tissue model for multiple myeloma, Tissue Engineering Part C: Methods, 2014, pp. 663-670.
Jenke et al., DNA Methylation Analysis in the Intestinal Epithelium—Effect of Cell Separation on Gene Expression an Methylation Profile, PLoS One, 2013, vol. 8(2), pp. 1-8.
Brittan et al., The gastrointestial stem cell, Cell Prolif., 2004, vol. 37, pp. 35-53.
Yamamoto et al., The Stabilization Effect of Mesenchymal Stem Cells on the Formation of Microvascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.

(56) References Cited

OTHER PUBLICATIONS

Yu et al., A Microfluidic-Based Multi-Shear Device for Investigating the Effects of Low Fluid-Induced Stresses on Osteoblasts, PLoS One, 2014, vol. 9(2), pp. 1-7.
GB 1903007.1 Search Report dated Jun. 24, 2020, 3 pages.
Extended European Search Report for EP 18802136.4 dated Jan. 22, 2021, 12 pages.
Kuratnik et al., Intestinal organoids at tissue surrogates for toxicological and pharmacological studies, biochemical Pharmacology, Apr. 25, 2013, vol. 85:12, pp. 1721-1726.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.
Lee et al. Microfluidic 3D bone tissue model for high-throughput evaluation of would healing and infection-preventing biomaterials, Biomaterials 33.4 2012 999-1006.
Amoroso M. W. et al., Accelerated High-Yield Generation of Limb-Innervating Motor Neurons from Human Stem Cells. J Neurosci, Jan. 9, 2013, vol. 33, No. 2, pp. 574-586 pp. 575 and 578, Fig. 1 and 2.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.
Written Opinion 11201901628X dated Mar. 10, 2021, 9 pages.
ISR-WO—for PCT/US2019/026195 Jun. 12, 2019, 10 pages.
Kondo, T. et al., Ipsc-based Coound screening and in vitro trials identify a synergistic anti-amyloid b combination for Alzheimer's Disease, Cell Reports, 2017, vol. 21, pp. 2304-2312.
McKinney, C.E. et al., Using induced pluripotent stem cells derived neurons to model brain diseases, Neural Regeneration Research, 2017, 12:7 pp. 1-11.
Li, Y. et al., Protein kinase C controls lysosome biogenesis independently of mTORC1, Nature Cell Biology, 2016, 10:10, pp. 1-26.
Kilpatrick, K. et al., Genetic and chemical activation of TFEB mediates clearance of aggregated a-synuclein, PLoS One, 2015, 10:3, pp. 1-21.
Chou, B.K. et al., Efficient human iPS cell derivation by a non-integrating plasmid from blood cells with unique epigenetic and gene eIDS filed Oct. 3, 2020pression signatures, Cell Research, 2011, 21:3, pp. 518-529.
Sundberg, m. et al., Improved cell therapy protocol for Parkinson's Disease based on differentiation efficiency and safety of Hesc-, Hipsc and non-human primate Ipsc-derived DA neurons, Stem Cells, 2013, 31:8, pp. 1-25.
International Search Report and Written Opinion of PCT/US2019/26183, Dated Jun. 12, 2019, 10 Pages.
ISR-WO—for PCT/US2019/026193 Jul. 1, 2019, 8 pages.
Notice of Reasons for Rejection for JP 2018-540028 dated Mar. 1, 2021.
International Search Report and Written Opinion of PCT/US2019/023749, Dated Jun. 25, 2019, 12 Pages.
Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.
Nostro et al., Efficient Generation of NKX6-1+ Pancreatic Progenitors from Multiple Human Pluripotent Stem Cell Lines, Stem Cell Reports, 2015 4(4), pp. 591-604.
Stepniewski et al., Induced Pluripotent Stem Cells as a Model for Diabetes Investigation, Scientific Reports, 2015, 5:8597, 14 pages.

* cited by examiner

Figure 8.
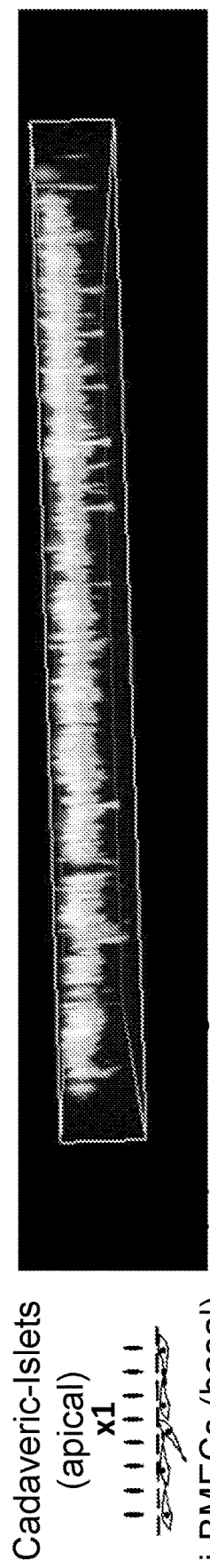
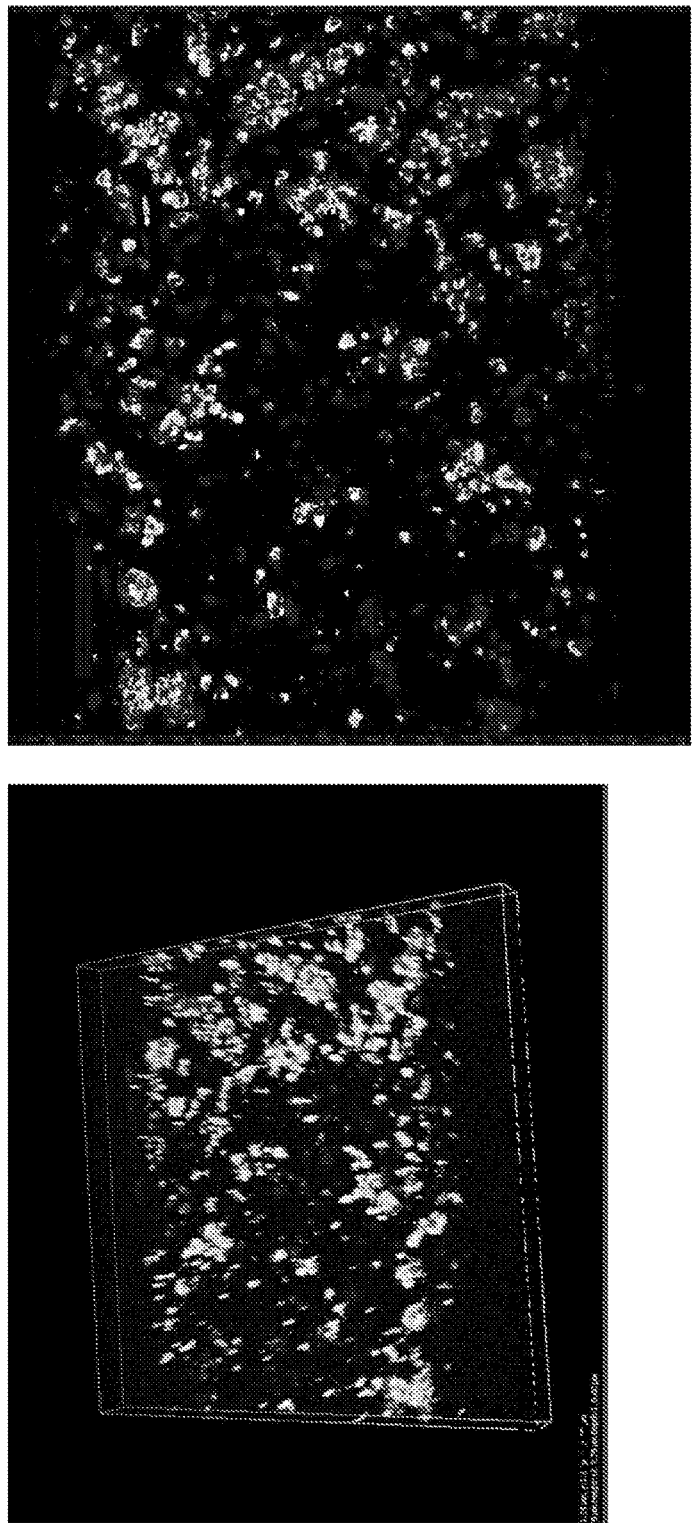
Cadaveric-Islets (apical)
i-BMECs (basal)
(transverse section of chip; imaging only apical channel and pores)

Figure 10.
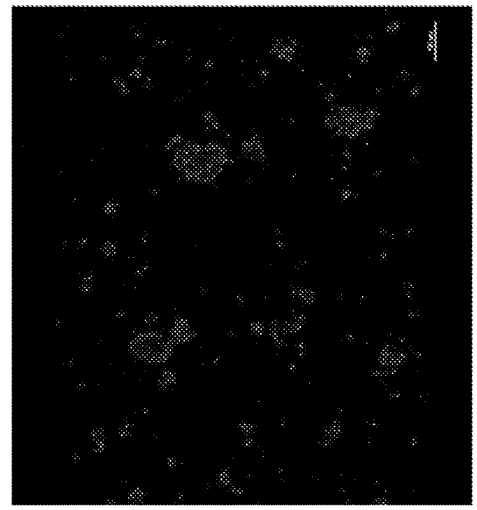
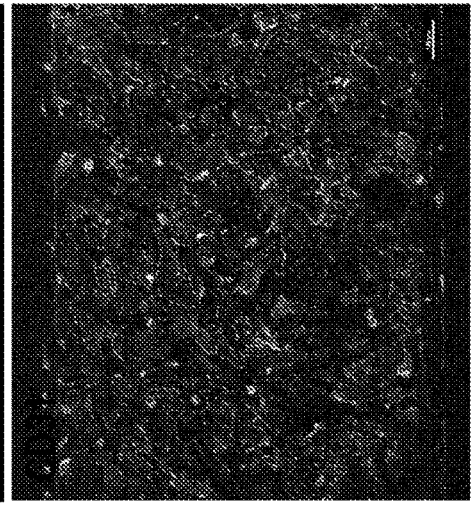
Best focus projection from top
Cadaveric-Islets (apical)
HUVECS cell line (basal)

Figure 18.
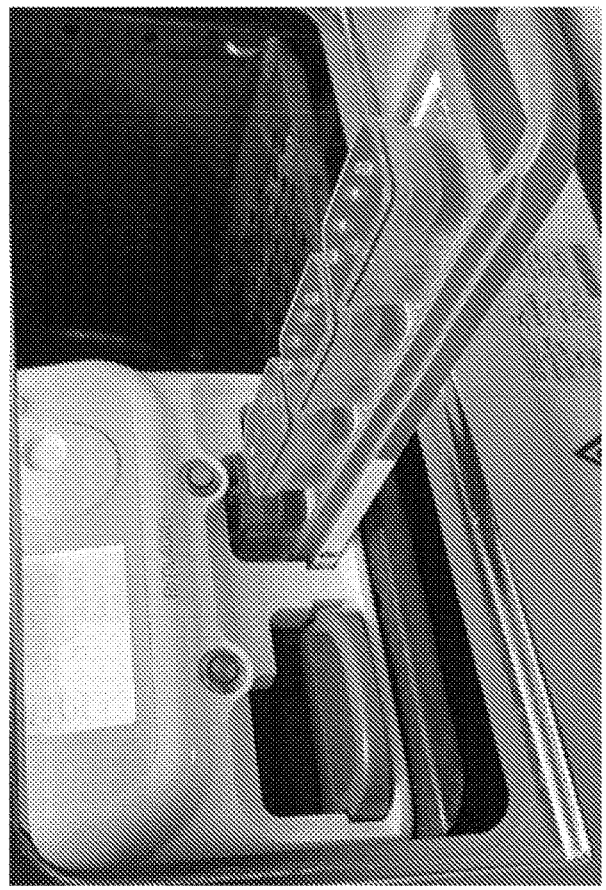
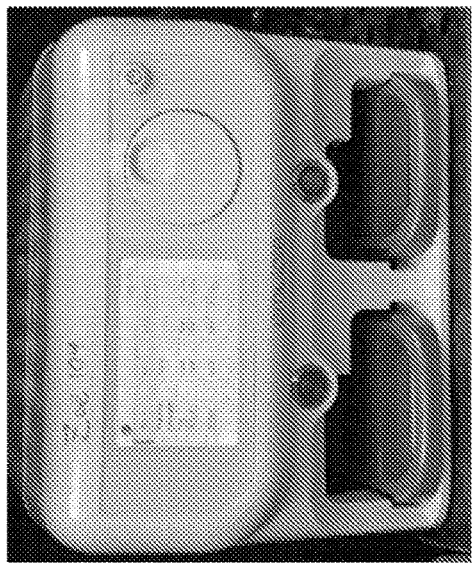
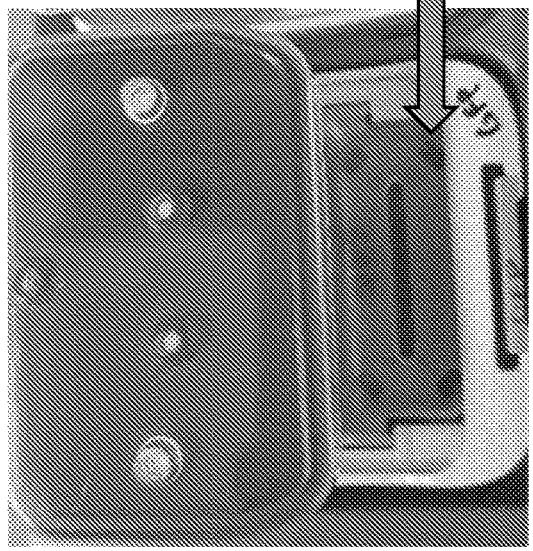

Figure 21.
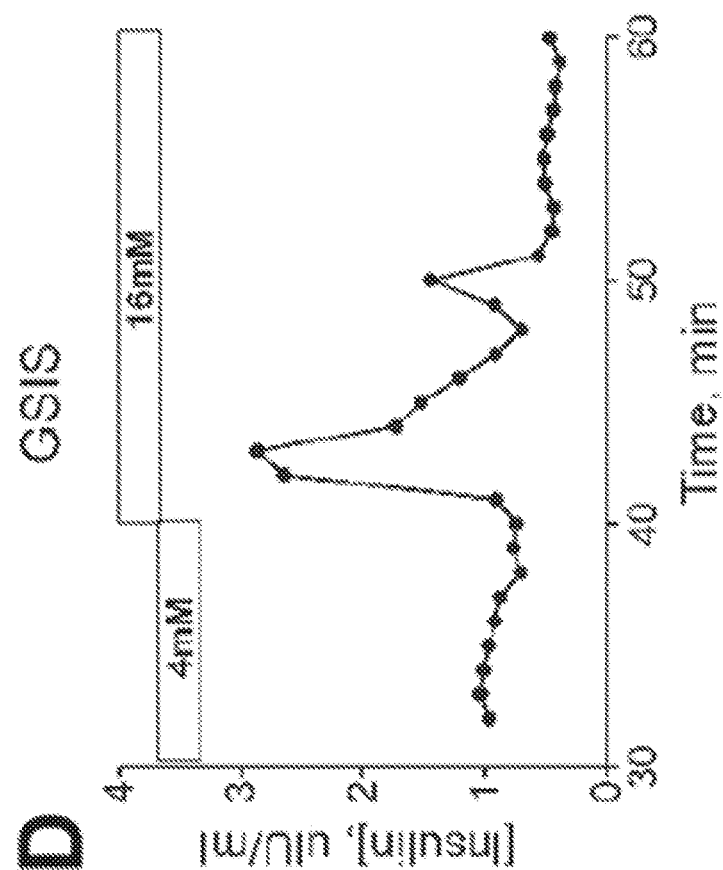
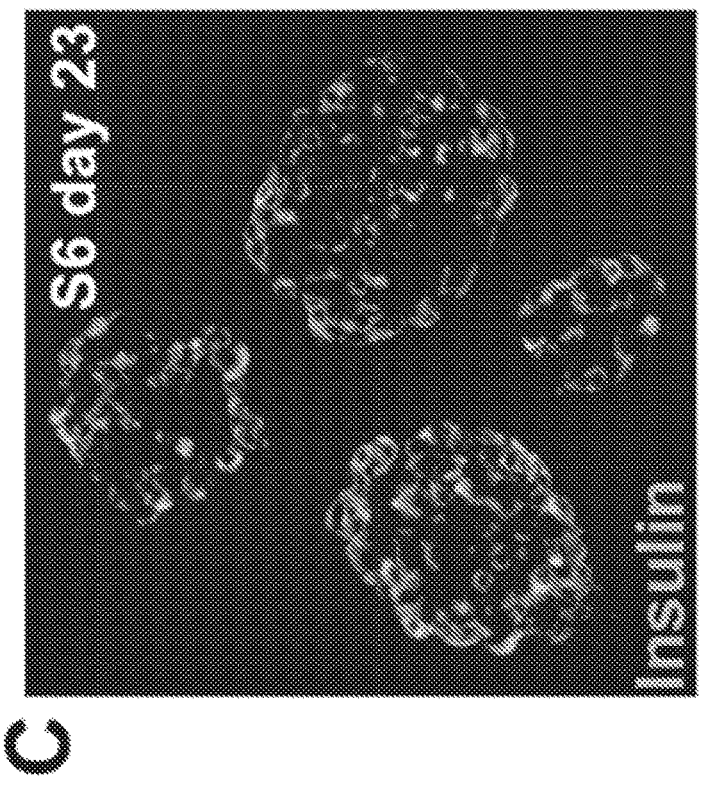

Figure 26.
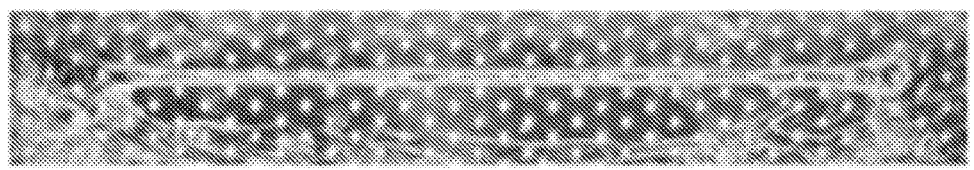
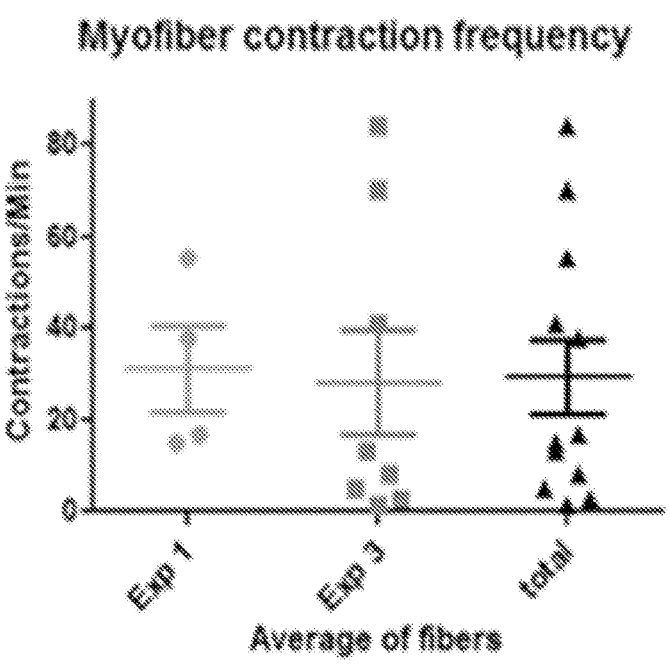
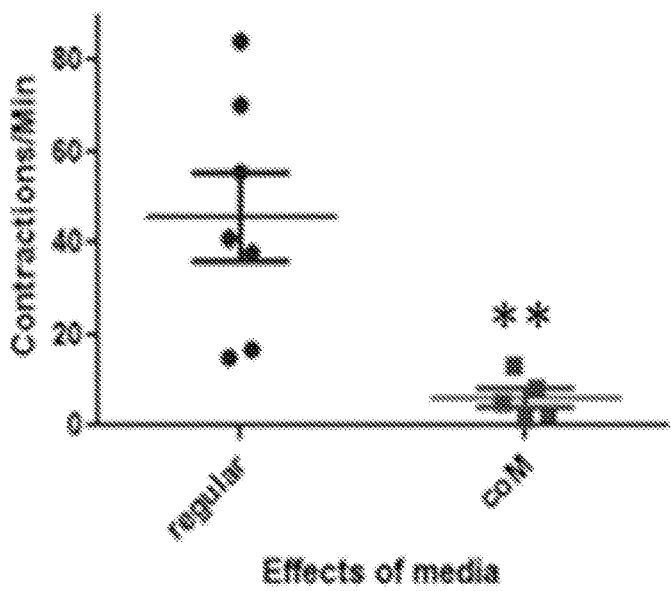

Day 23 ICC: Alk5i, T3

DAPI C-Peptide Glucagon NKX6.1

Alk5i, T3, XXI

Alk5i, T3, NOGGIN

Alk5i, T3, XXI, NOGGIN

Figure 39.
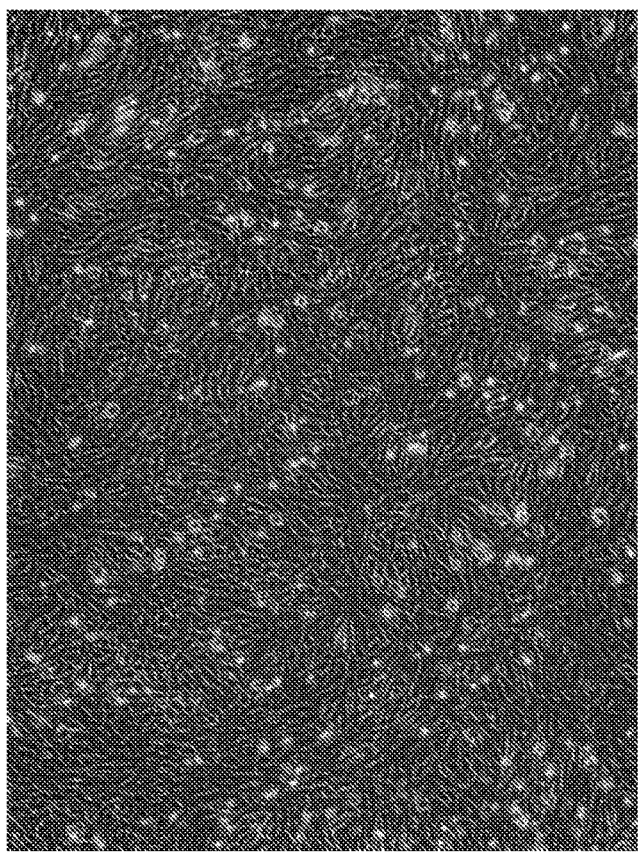
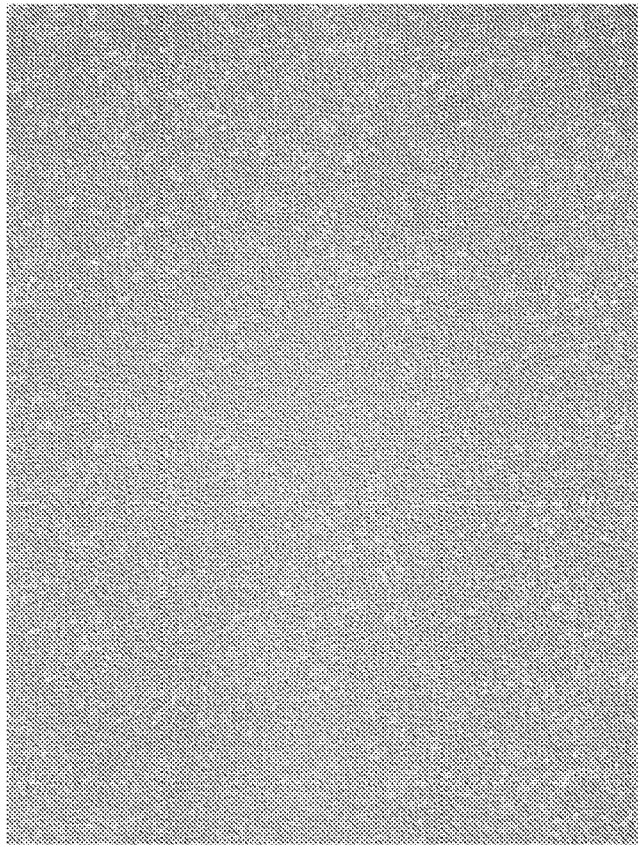

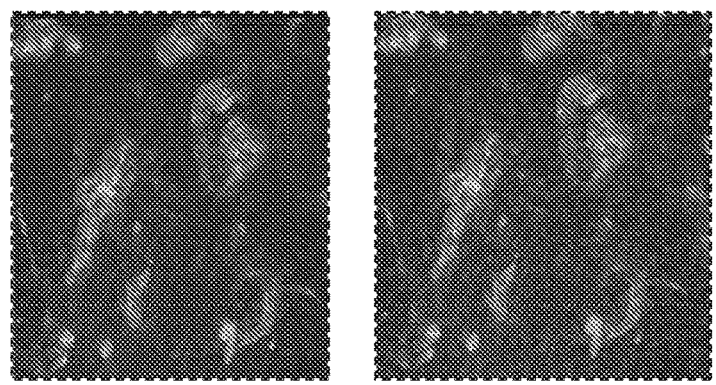
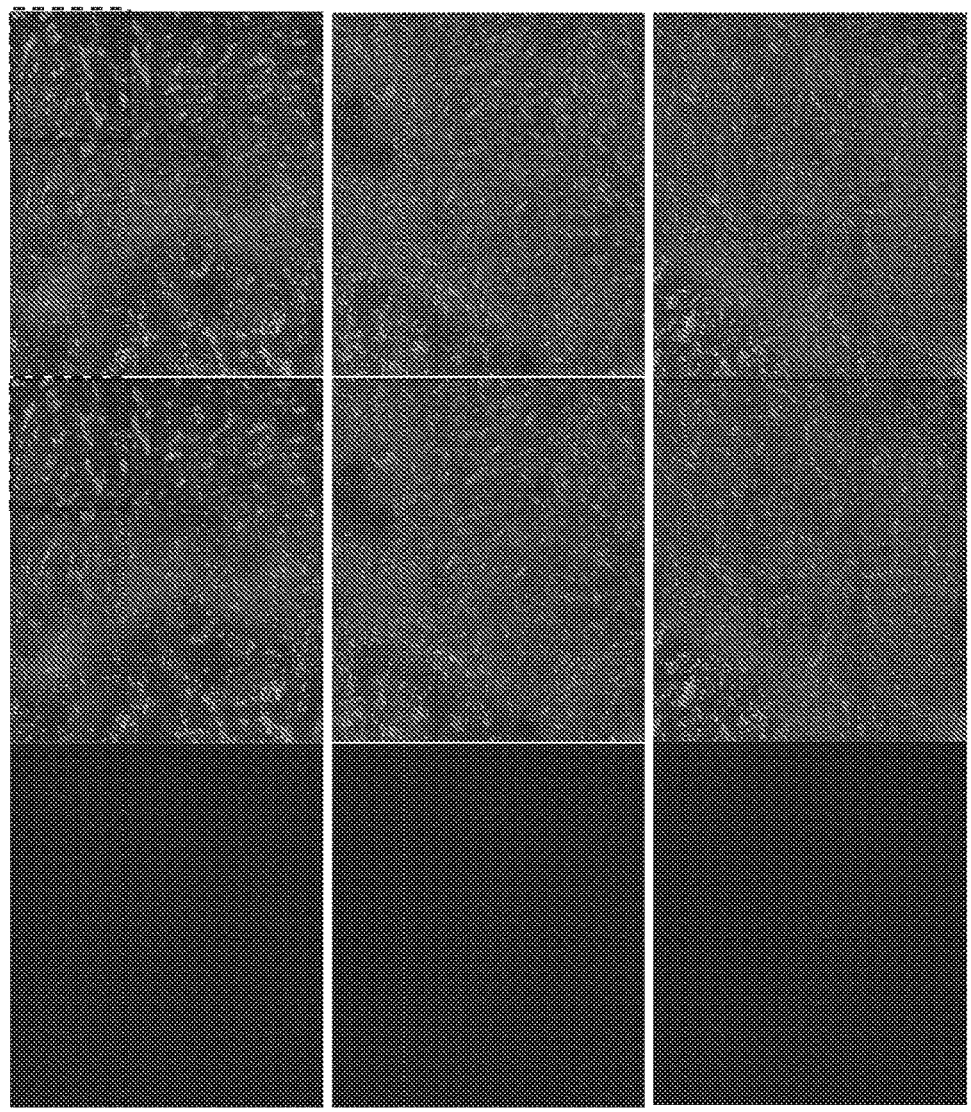
Figure 40.
ICC for CD31 (10 days of differentiation):

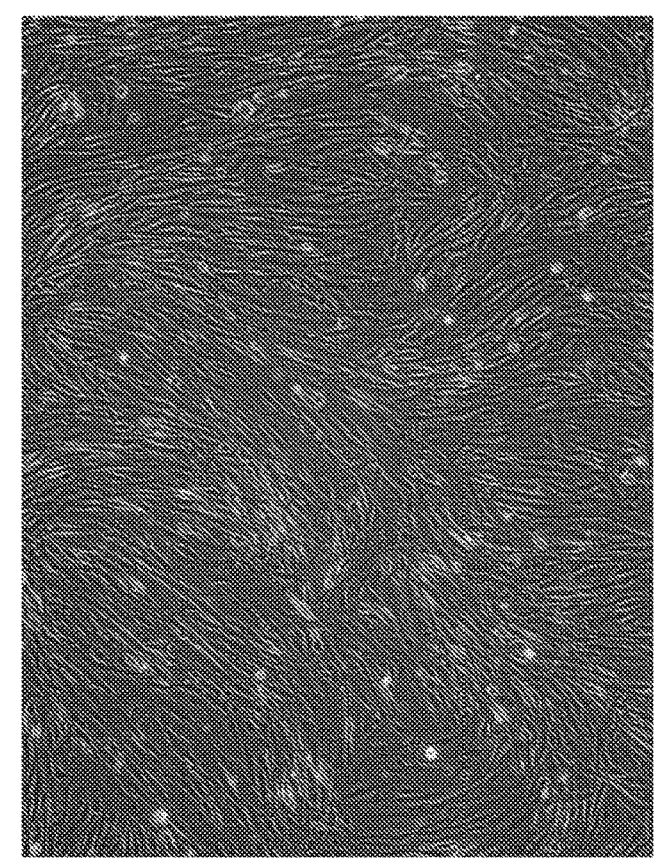
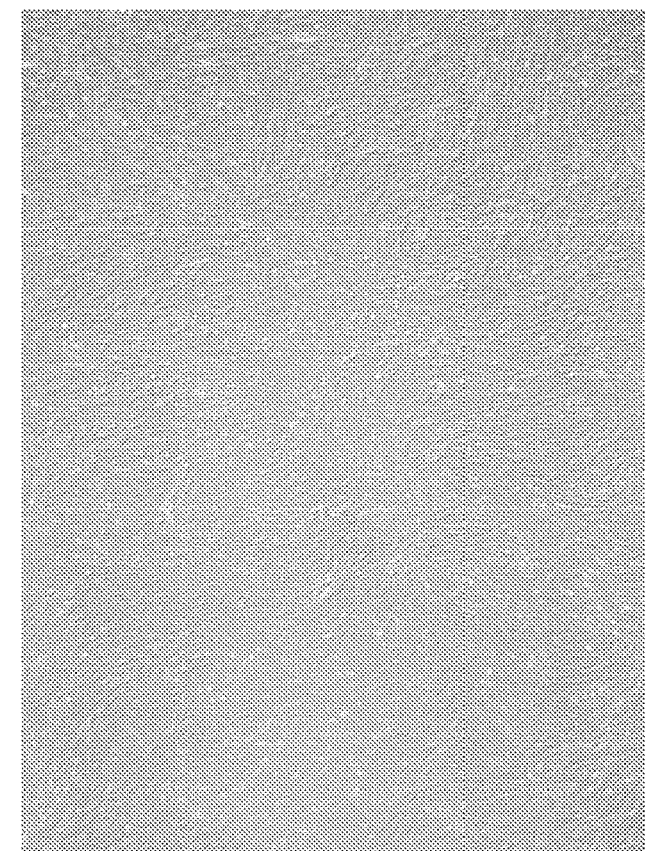
Figure 41.

Figure 46.
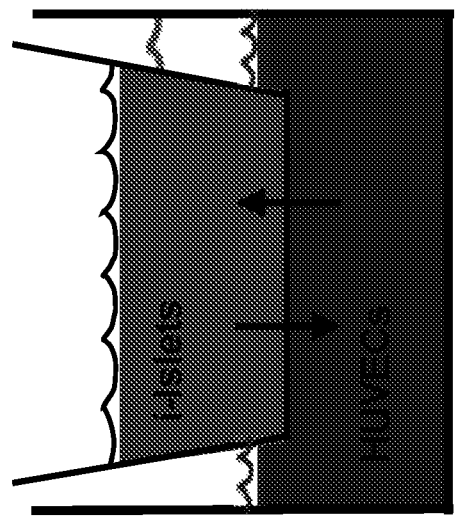
TRANS-WELL

Figure 49.
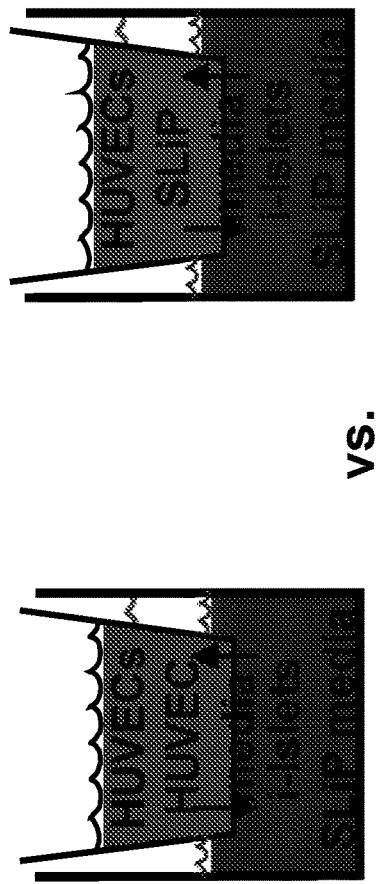
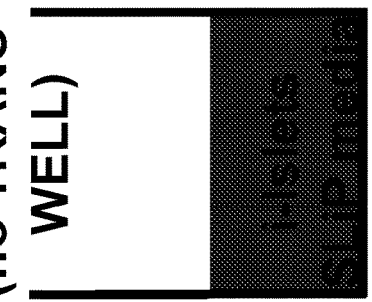
*SLiP: <u>S</u>areen <u>L</u>ab <u>i</u>PSC-derived <u>P</u>ancreatic endoderm differentiation media Huvecs (Slip media)
i-Islets (Slip media)

METHODS OF USE OF ISLET CELLS

CROSS-REFERENCE TO RELATED APPLICATIONS

This application is a National Phase of International Application No. PCT/US2019/023749, filed Mar. 22, 2019, which designated the U.S. and that International Application was published under PCT Article 21(2) in English, which claims the benefit under 35 U.S.C. § 119(e) to U.S. provisional patent application No. 62/647,548, filed Mar. 23, 2018, the contents of which are incorporated herein by reference in their entirety.

FIELD OF THE INVENTION

The present invention relates to the field of culturing cells, and in particular, culturing islet cells together with other cell types in a fluidic device, including but not limited to a microfluidic device or chip.

BACKGROUND

Type 2 diabetes (T2D) is a clinical syndrome caused by insufficient insulin secretion for insulin requirements. This can be due to a marked β-cell defect with moderate insulin resistance ((3-T2D) or marked insulin resistance with a modest β-cell defect (IR-T2D). β-T2D are typically lean requiring early β-cell directed therapy, while IR-T2D are typically obese requiring early muscle insulin sensitizer therapy. Because of inaccessibility to relevant human organs, drug discovery and mechanistic studies of β-cell dysfunction and insulin resistance in T2D have relied largely on rodent models such as those with defective leptin signaling. These models have been poorly predictive of disease mechanisms or drug efficacy in humans, contributing to the high cost of drug development. Moreover, inbred rodent models fail to reproduce the wide range of relative defects in insulin secretion and insulin sensitivity in humans with T2D that predictably require different therapeutic approaches targeted predominantly to β-cell preservation and function versus insulin action. Therefore, development of human Organ-chip models representative of the range of T2D types would overcome a major obstacle in evaluating disease mechanisms and provide a more relevant drug screening tool. There is a great need in the art for such models.

SUMMARY OF THE INVENTION

Described herein is a method of generating pancreatic progenitor cells, including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1. In other embodiments, the method includes culturing immature endocrine cells in the presence of T3, Alk5i, R428 and NAC for about 7 days to generate mature endocrine cells. In other embodiments, the mature endocrine cells express one or more of: C-peptide, glucagon and MafA. In various embodiments, the immature endocrine cells are islet cells. In various embodiments, the islet cells are beta islet cells. In other embodiments, the islet cells are capable of producing insulin. In other embodiments, the islet cells secrete insulin C-peptide. In other embodiments, the islet cells are glucose responsive. In other embodiments, the iPSCs derived from a diabetic subject.

Described herein is a quantity of pancreatic progenitor cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both.

Described herein is a quantity of endocrine progenitor cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells.

Described herein is a quantity of immature endocrine cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1.

Described herein is a quantity of mature endocrine cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells.

In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1. In other embodiments, the method includes culturing immature endocrine cells in the presence of T3, Alk5i, R428 and NAC for about 7 days to generate mature endocrine cells. In other embodiments, the mature endocrine cells express one or more of: C-peptide, glucagon and MafA. In other embodiments, the immature endocrine cells are islet cells. In other embodiments, the mature endocrine cells are islet cells. In other embodiments, the islet cells are beta islet cells. In other embodiments, the islet cells are capable of producing insulin. In other embodiments, the islet cells secrete insulin C-peptide. In other embodiments, the islet cells are glucose responsive.

Described herein is a method of generating endothelial cells, including culturing (iPSCs) in the presence of CHIR99012 for about 2 days to generate mesoderm, culturing mesoderm in the presence of BMP4, VEGF, and FGF2 for about 2 days to generate vascular progenitor cells, culturing vascular progenitors in the presence of EGM-MV2 and VEGF for about 4-6 days to generate endothelial progenitor cells, and culturing endothelial progenitor cells in the presence of EGM-MV2 and VEGF to generate endothelial cells. In other embodiments, the vascular progenitor cells express one or more of: CD31+, CD34+, VEGF+, and VEGFA+ at day 20.

Also described herein is a quantity of endothelial cells made by a method of generating endothelial cells, including culturing (iPSCs) in the presence of CHIR99012 for about 2 days to generate mesoderm, culturing mesoderm in the presence of BMP4, VEGF, and FGF2 for about 2 days to generate vascular progenitor cells, culturing vascular progenitors in the presence of EGM-MV2 and VEGF for about 4-6 days to generate endothelial progenitor cells, and culturing endothelial progenitor cells in the presence of EGM-MV2 and VEGF to generate endothelial cells. In other embodiments, the vascular progenitor cells express one or more of: CD31+, CD34+, VEGF+, and VEGFA+ at day 20.

Described herein is a method of culturing cells, including: a) providing i) islet cells and ii) a microfluidic device including one or more surfaces; b) seeding islet cells on said one or more surfaces so as to create seeded cells; and c) exposing said seeded cells to a flow of culture media for a period of time so as to create perfused cells. In various embodiments, the islet cells are induced islet cells. In various embodiments, the islet cells are human cadaveric islet cells. In various embodiments, the microfluidic device includes a channel including one or more surfaces and said seeding of step b) results in seeding islet cells on at least one surface of said channel. In various embodiments, the microfluidic device includes a membrane, said membrane including a top surface and a bottom surface, and said seeding of step b) results in seeding islet cells on the top or bottom surface of the membrane. In various embodiments, the islet cells are seeded on said top surface of the membrane. In various embodiments, the method further includes seeding a different type of cell on the bottom surface of the membrane. In various embodiments, the endothelial cells are seeded on the bottom surface of the membrane. In various embodiments, the endothelial cells are iPSC derived brain microvascular endothelial cells (iBMECs). In various embodiments, the endothelial cells are human umbilical vein endothelial cells (HUVECs). In various embodiments, the skeletal muscle cells are seeded on said bottom surface of the membrane. In various embodiments, the method includes the step of stimulating said cells with glucose so as to create stimulated cells. In various embodiments, the method includes the step of detecting insulin secretion by said stimulated cells. In various embodiments, measuring insulin secretion by said stimulated cells, wherein the amount of insulin secretion is higher in the presence of said endothelial cells as compared to the absence of said endothelial cells.

In various embodiments, the method includes measuring insulin secretion by said stimulated cells, wherein the amount of insulin secretion is higher in the presence of said flow as compared to the absence of said flow.

BRIEF DESCRIPTION OF THE FIGURES

FIG. 8. Cadaveric islets in apical channel and iBMECs in basal channel. Multiple views including transverse section, 3D projection view, best focus projection via, each including Hoescht, c-peptide, glucagon, glut-1 stain. Best focus projection from top.

FIG. 10. Cadaveric islets in apical channel and HUVECs in basal channel. Top view. Hoescht, c-peptide, glucagon, CD31 and merge stain. Best focus projection from top.

FIG. 18. (A) A front view image of the Zoe flow machine, (B) Top view image of a chip (blue arrow) placed inside a pod, (C) Zoe showing a fully assembled system, with chips in pods placed in a tray ready to begin media flow through the chips. Each Zoe contains two trays which can accommodate up to 6 chips with pods each and hence come with a capacity of 12 chip-pods. A pod is the device which aids in connecting the chip to the Zoe. Upon insertion of chips to the pods, the ports (inlet and outlet) of the chip align with the via ports in the pods thereby completing a circuit. The inlet and outlet reservoirs contain the feeding medium and the effluent medium respectively. When this Chip-pod unit is placed inside a Zoe, the medium is able to flow through the channels at a desired flow rate.

(A) Immunohistological staining of the i-MNs co-cultured with iBMECs. (B) GFP-labeled neurons or iBMECs co-cultured on chips were harvested and sorted for mRNA-seq. Principle component analysis plots of first two principle components (PC) (top) and PCs 2, and 3 (bottom). Arrows indicate weighting along the axis of each respective PC. Top 200 ranked genes from each PC displayed as Z-score calculated across all conditions for each row and indicated by colorimetric scale. Each PC analyzed by DAVID pathway analysis and top 7 categories listed for each PC. The number of genes (count) in each category are displayed with corrected significance values from DAVID analysis.

Figure 25:
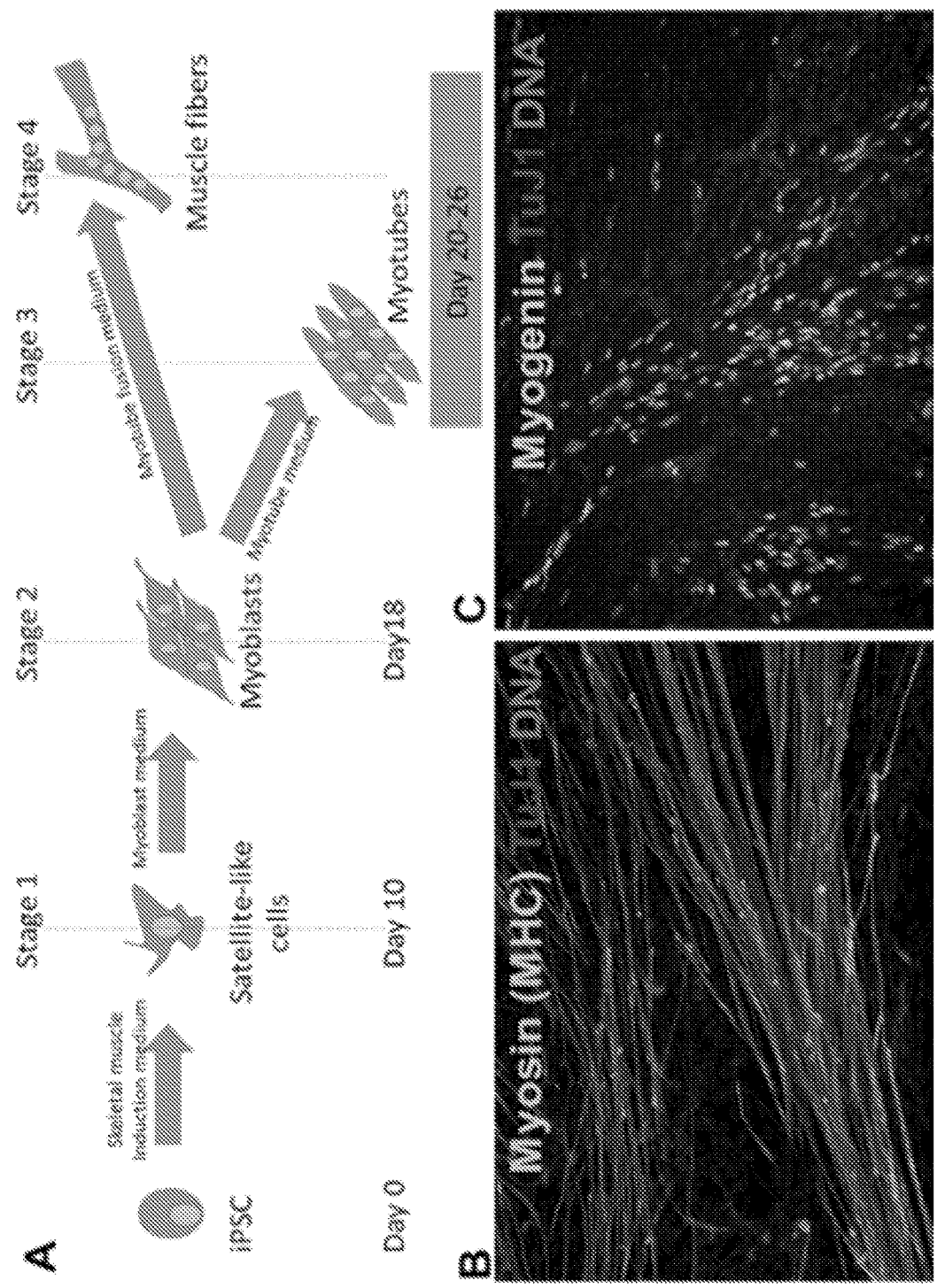
Figure 25:
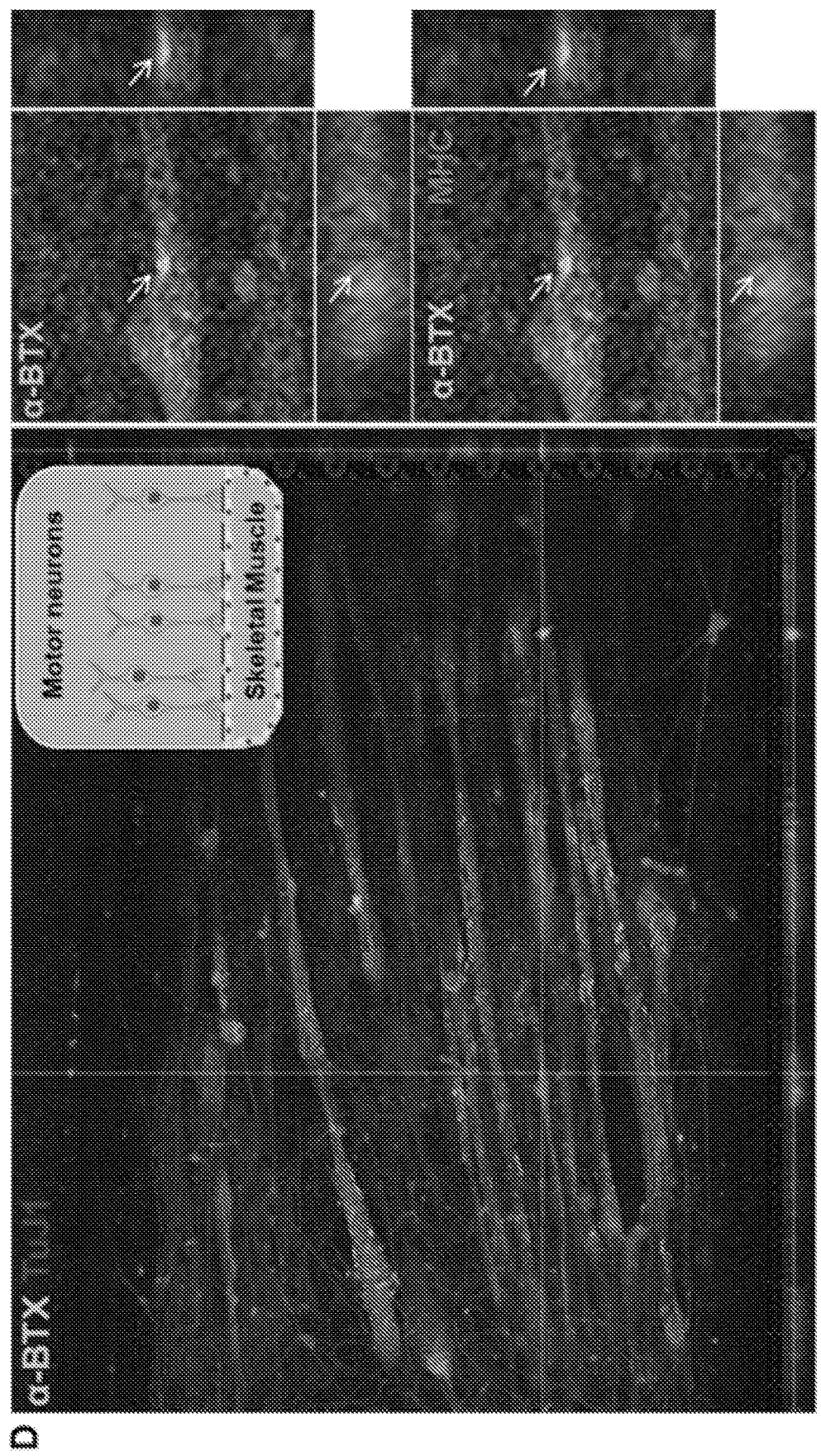
Figure 26:
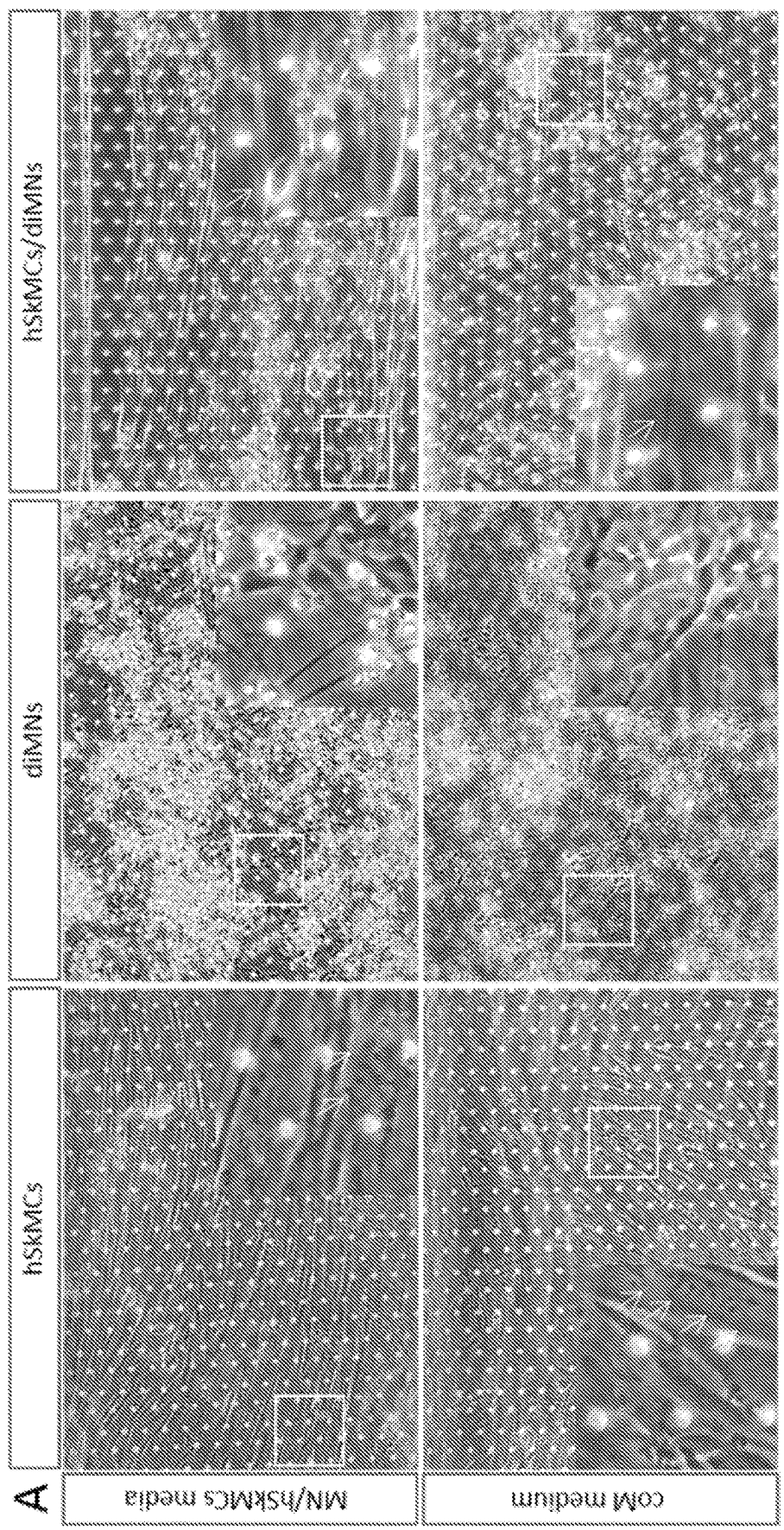
Figure 26:
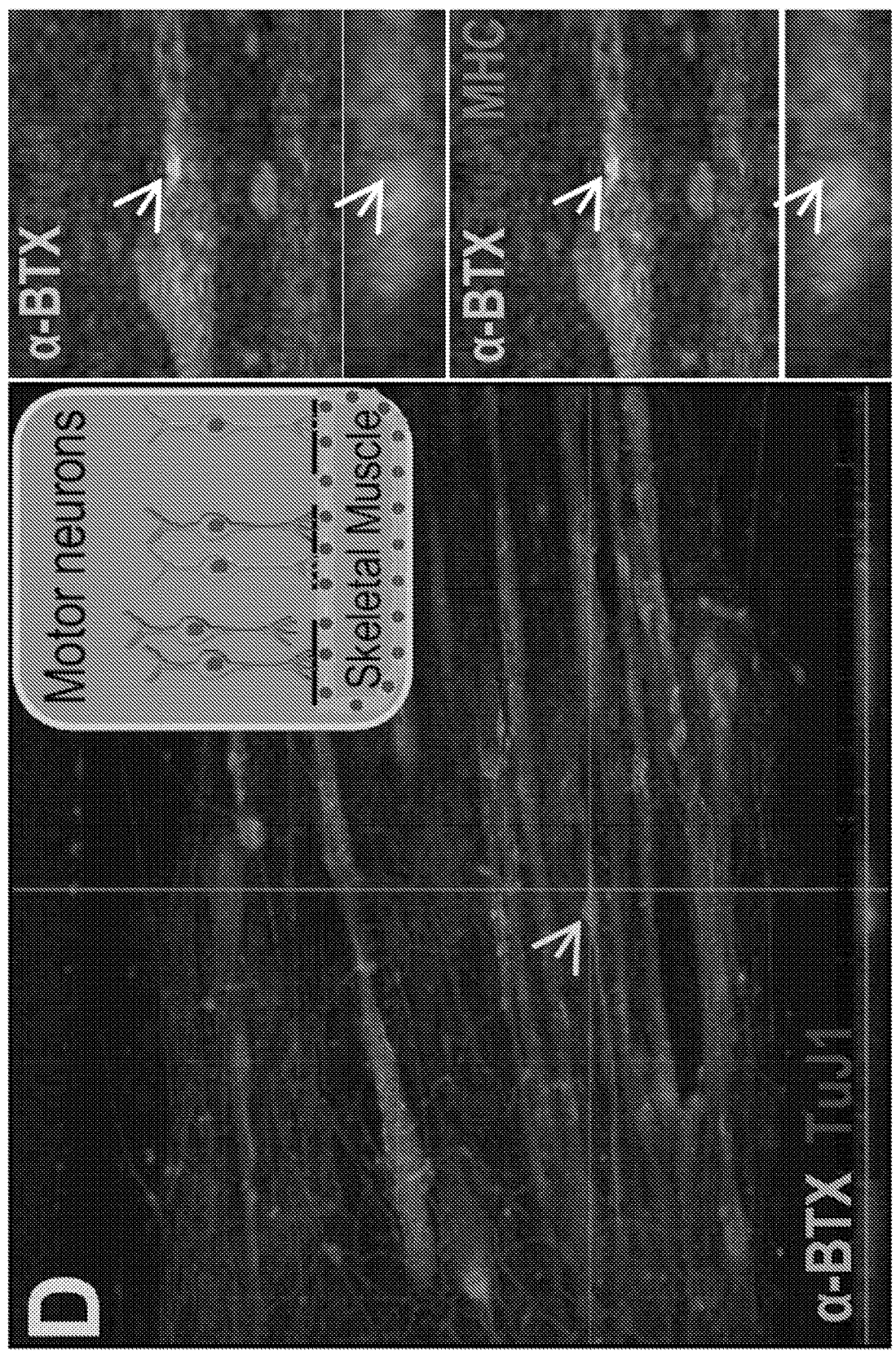

FIG. 25. iPSC-derived and primary Skeletal Muscle on chips: (A) Schematic of iPSC-derived myoblasts and skeletal muscle differentiation. (B) and (C) Representative images from the Inventors' 25-day differentiation protocol for co-developing motor neurons (TuII/βIII-tubulin) and skeletal muscle (MHC and Myogenin) from hiPSCs. (D) Primary human skeletal muscle and iPSC-derived motor neurons seeded on organ-chips showing formation of innervated SkM with neuromuscular junctions as observed by co-localization of bungarotoxin stained AChR clusters FIG. 26. SkM-on-Chip: (A) primary human skeletal muscle cells (hSkMC) were cultured on basal side of chip with or without iPSC-derived motor neurons (iMNs) on apical side; arrows point to the muscle fibers. (B) image of the spontaneously contracting myofiber on chip. (C) muscle fibers contract when co-cultured with iMNs. (D) hSkMC and iMN form neuromuscular junctions as observed by colocalization of stains for bungarotoxin (a-BTX, green), myosin heavy chain (MEW, blue) and neuronal βIII tubulin.

Figure 27:
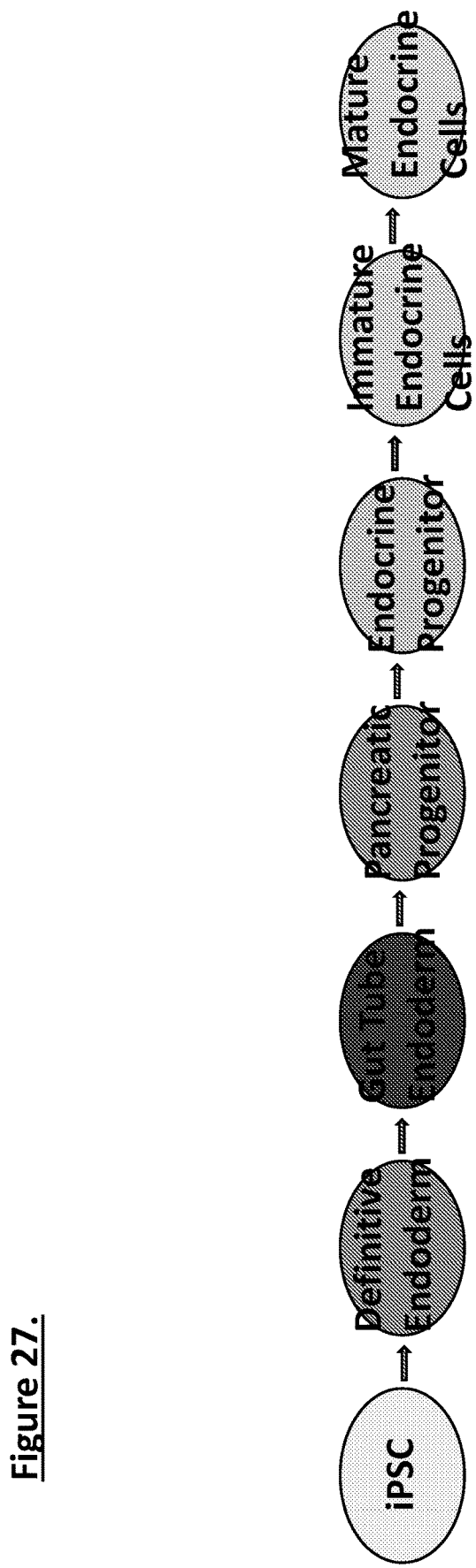

FIG. 27. Stages of differentiation towards endocrine lineage.

Figure 28:
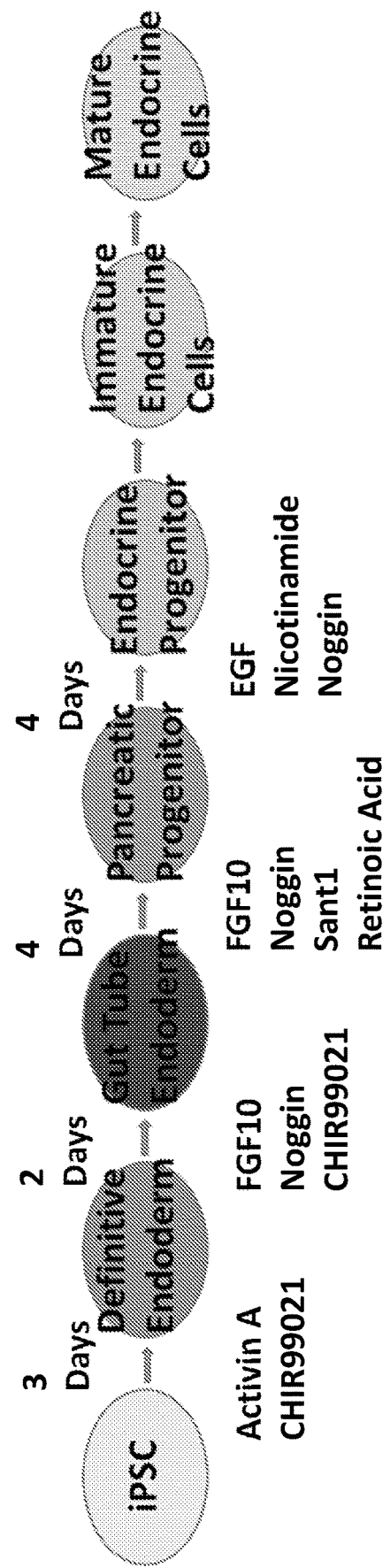

FIG. 28. Early stages of differentiation towards endocrine progenitors using compound combinations.

Figure 29:
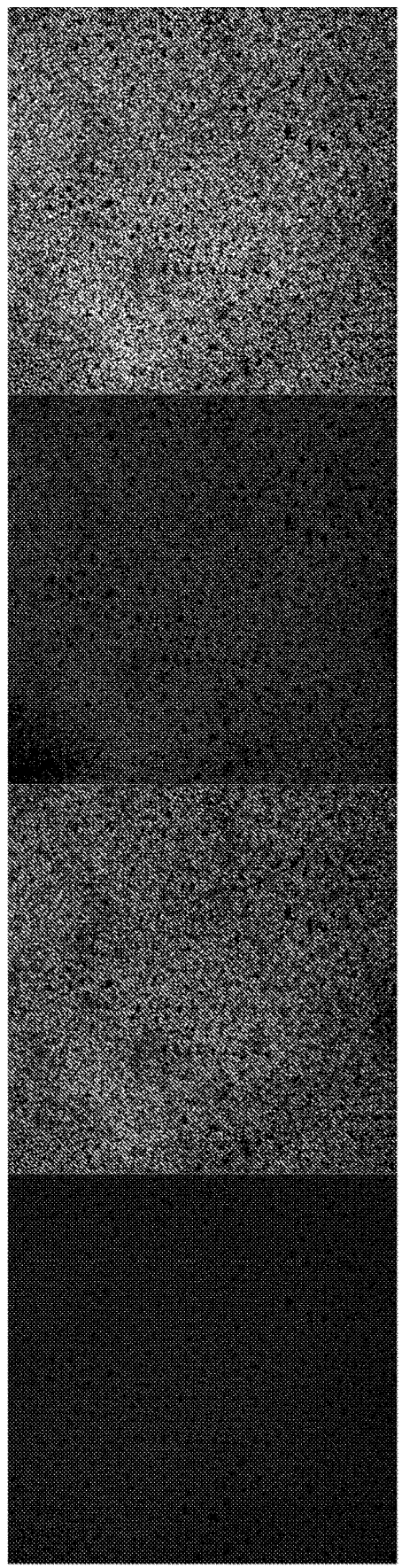

FIG. 29. Expression of DAPI, PDX1, NKX6.1 in differentiated cells.

Figure 30:
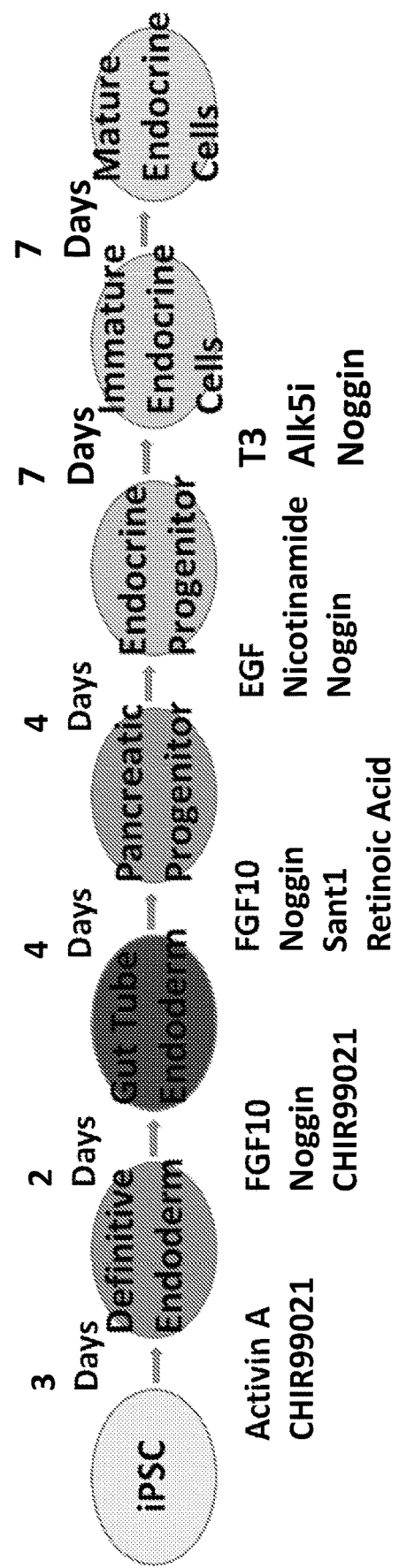

FIG. 30. Later stages of endocrine differentiation using compound combinations.

Figure 31:
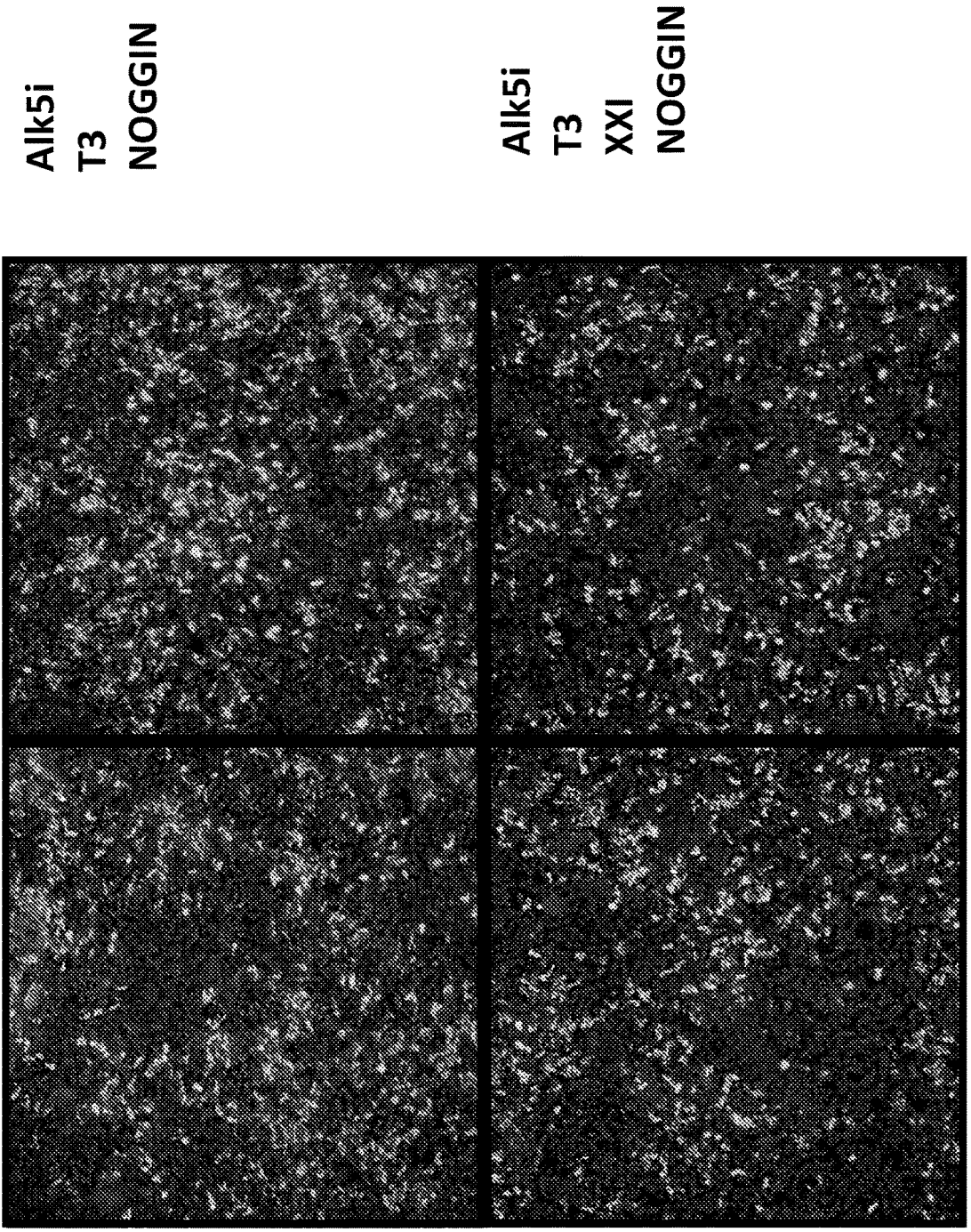

FIG. 31. Expression of DAPI, C-Peptide, Glucagon and NKX6.1 when testing various compounds at day 23.

Figure 32:
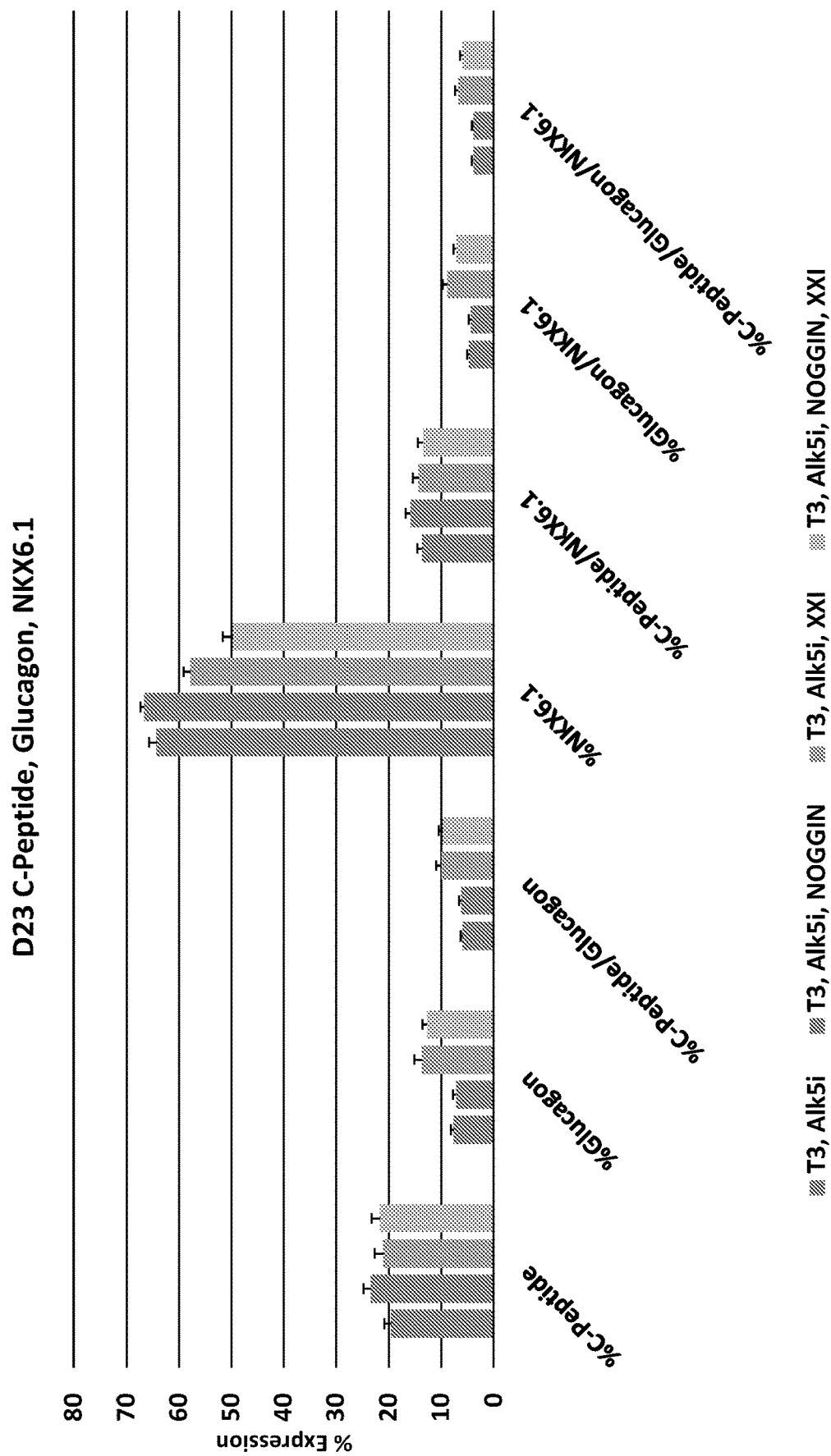

FIG. 32. Measurement of DAPI, C-Peptide, Glucagon and NKX6.1 expression across tested compound combinations.

Figure 33:
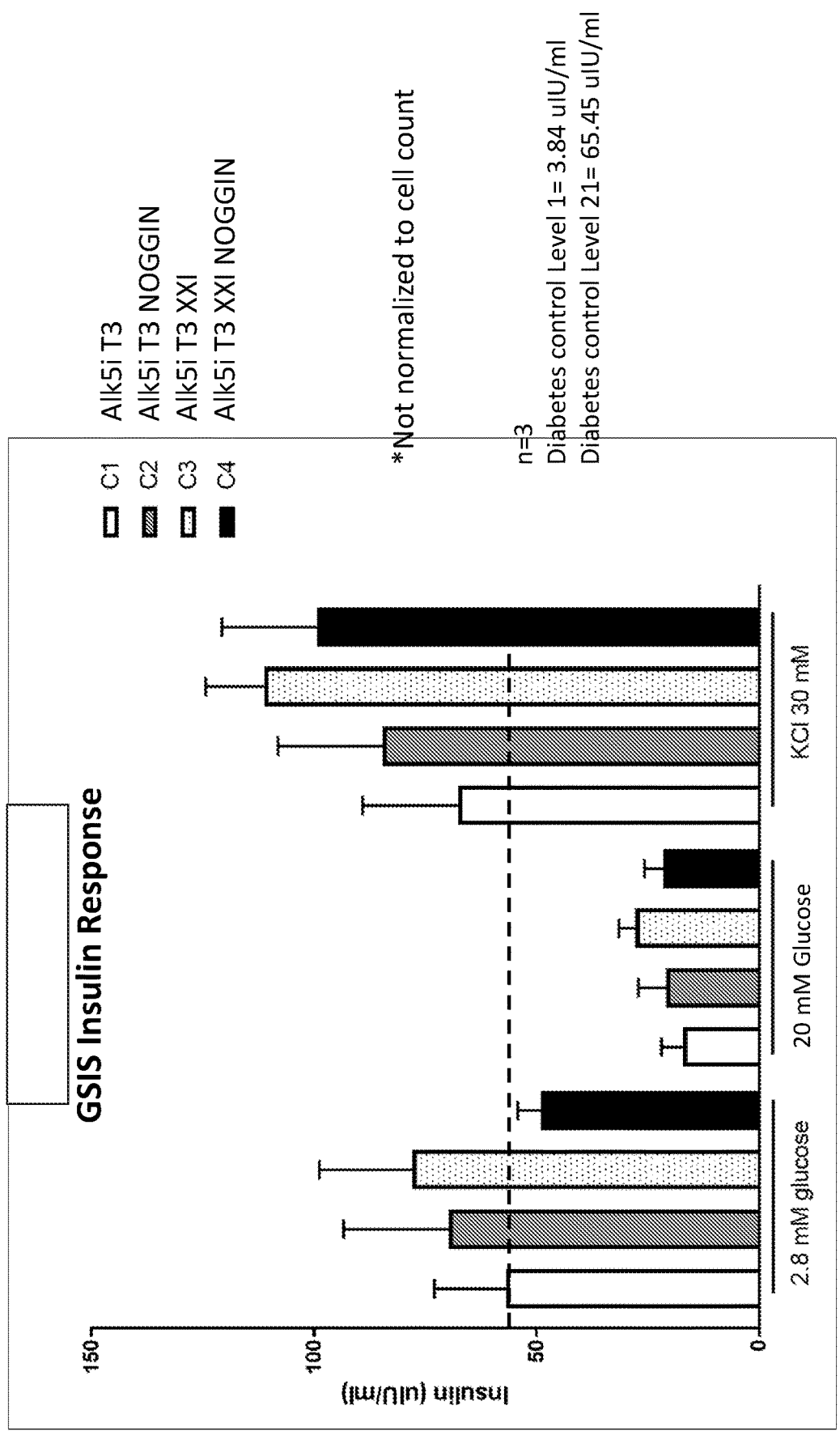

FIG. 33. Glucose stimulated insulin secretion insulin response across tested compound combinations.

Figure 34:
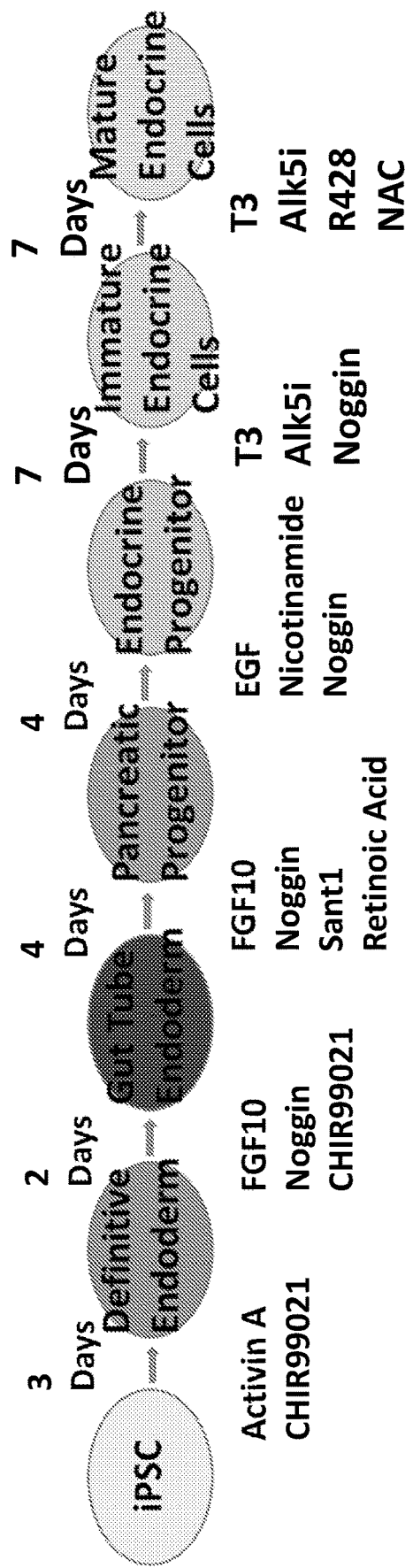

FIG. 34. Late stage endocrine differentiation and maturation.

Figure 35:
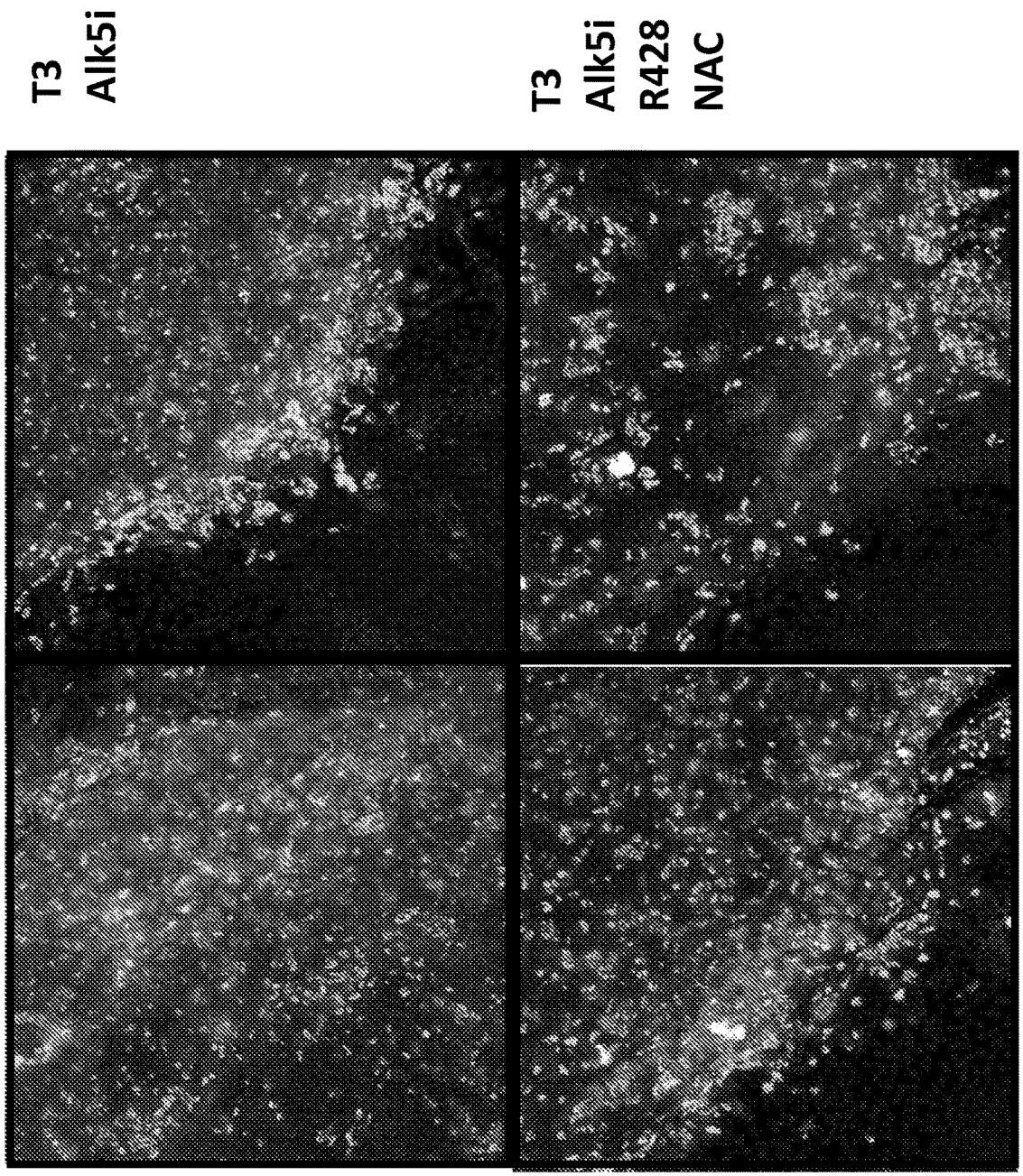

FIG. 35. Expression of DAPI, C-Peptide, Glucagon and MafA when testing various compounds at day 28.

Figure 36:
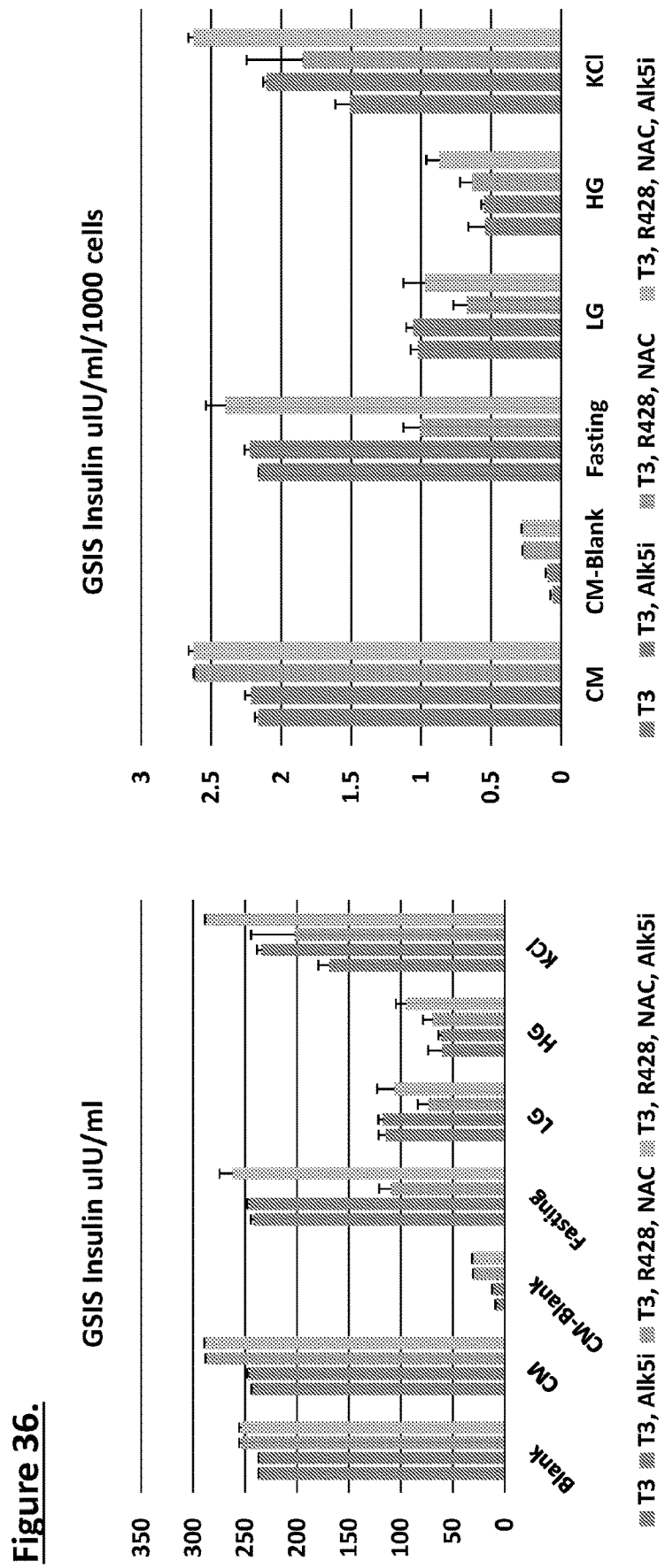

FIG. 36. Measurement of Glucose stimulated insulin secretion insulin response across tested compound combinations.

Figure 37:
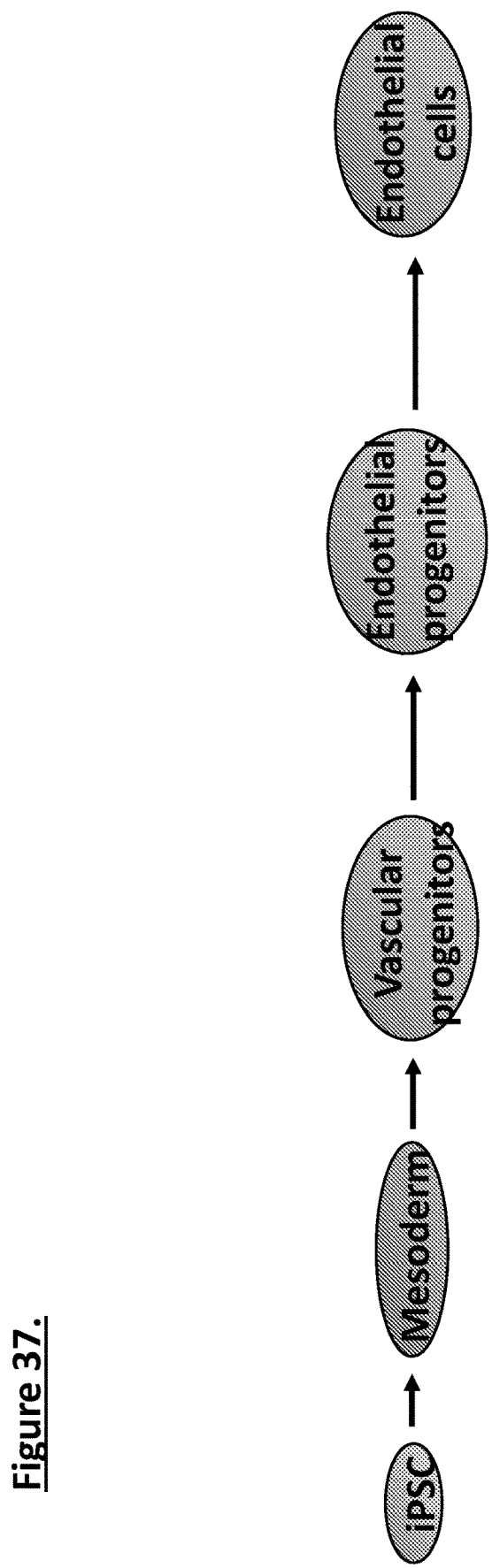

FIG. 37. Stages of iPSC-derived endothelial cells differentiation.

Figure 38:
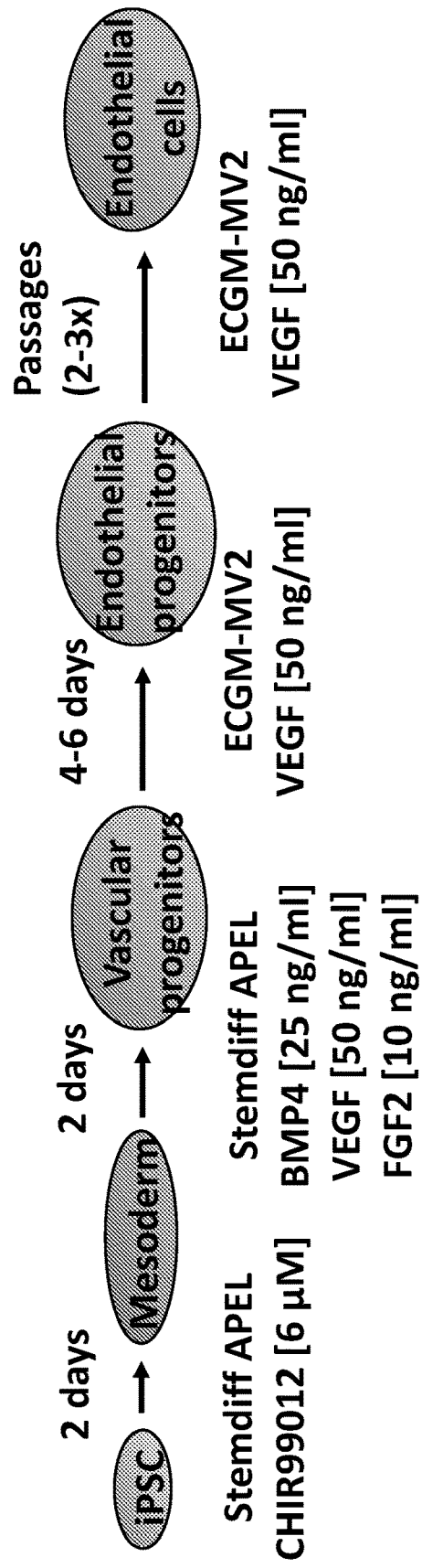

FIG. 38. Phases of iPSC-derived endothelial cells differentiation using compound combinations.

FIG. 39. Brightfield images (10 days of differentiation) at 4× and 10×.

FIG. 40. Images of 10 days differentiation. DAPI and ICC for CD31 (10 days of differentiation).

FIG. 41. Brightfield images (20 days of differentiation) at 4× and 10×.

Figure 42:
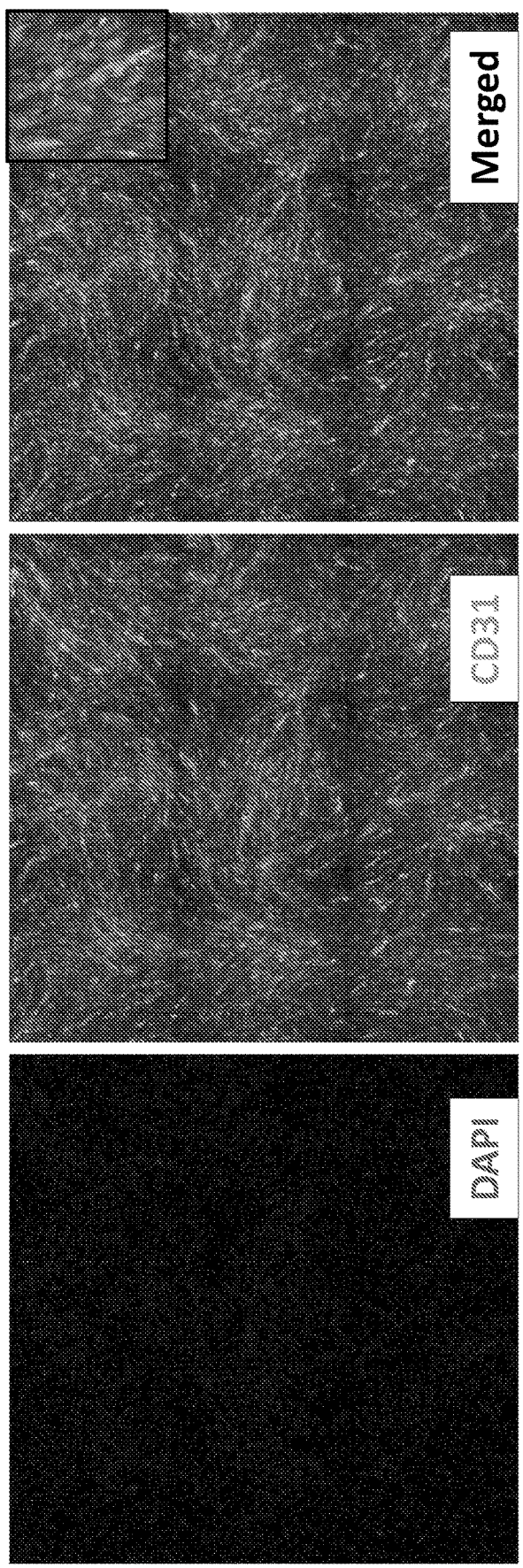

FIG. 42. Images of 20 days differentiation. DAPI and ICC for CD31 (20 days of differentiation).

Figure 43:
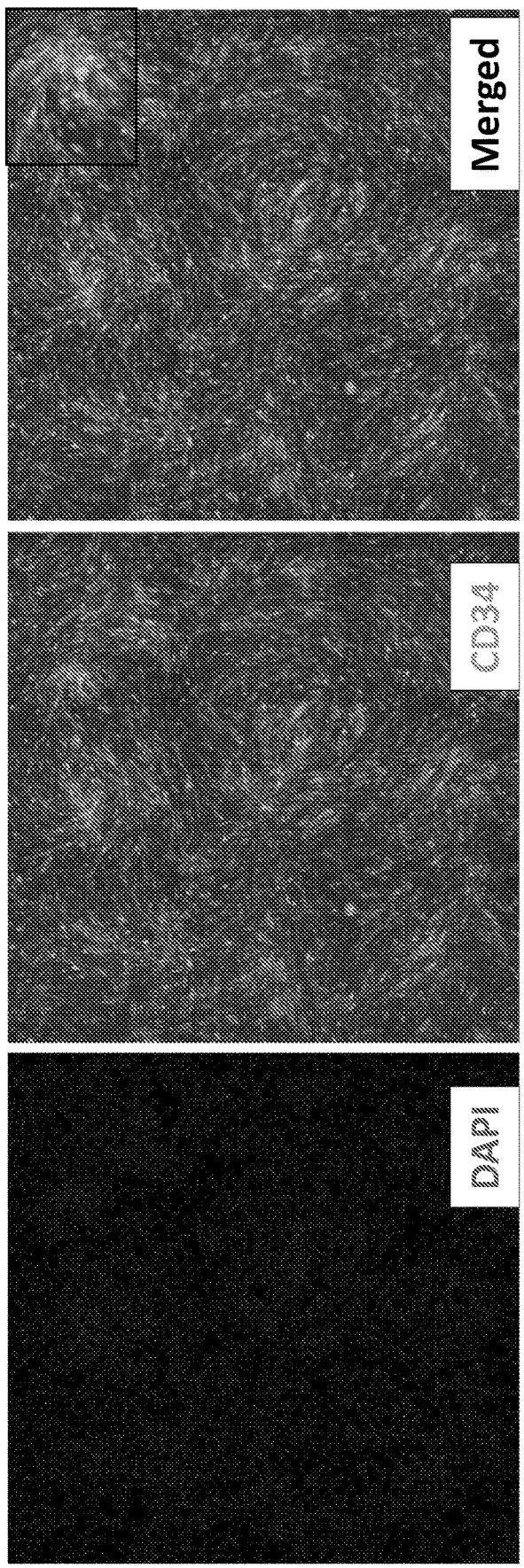

FIG. 43. Images of 20 days differentiation. DAPI and ICC for CD34 (20 days of differentiation).

Figure 44:
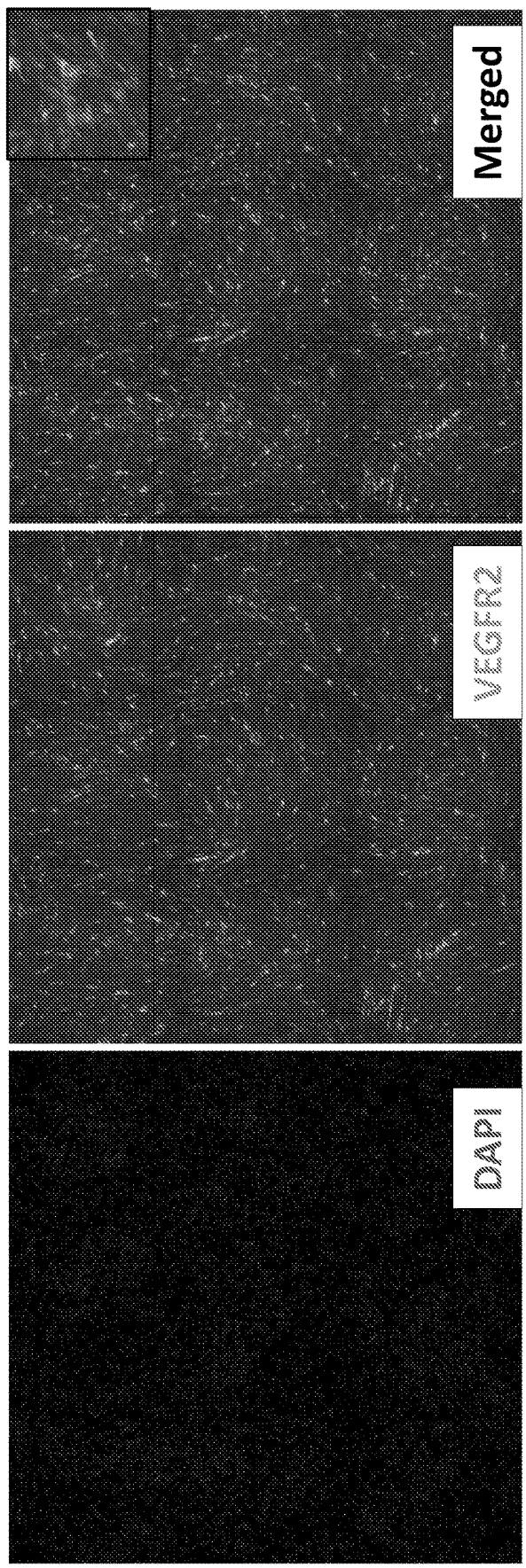

FIG. 44. Images of 20 days differentiation. DAPI and ICC for VEGFR2 (20 days of differentiation).

Figure 45:
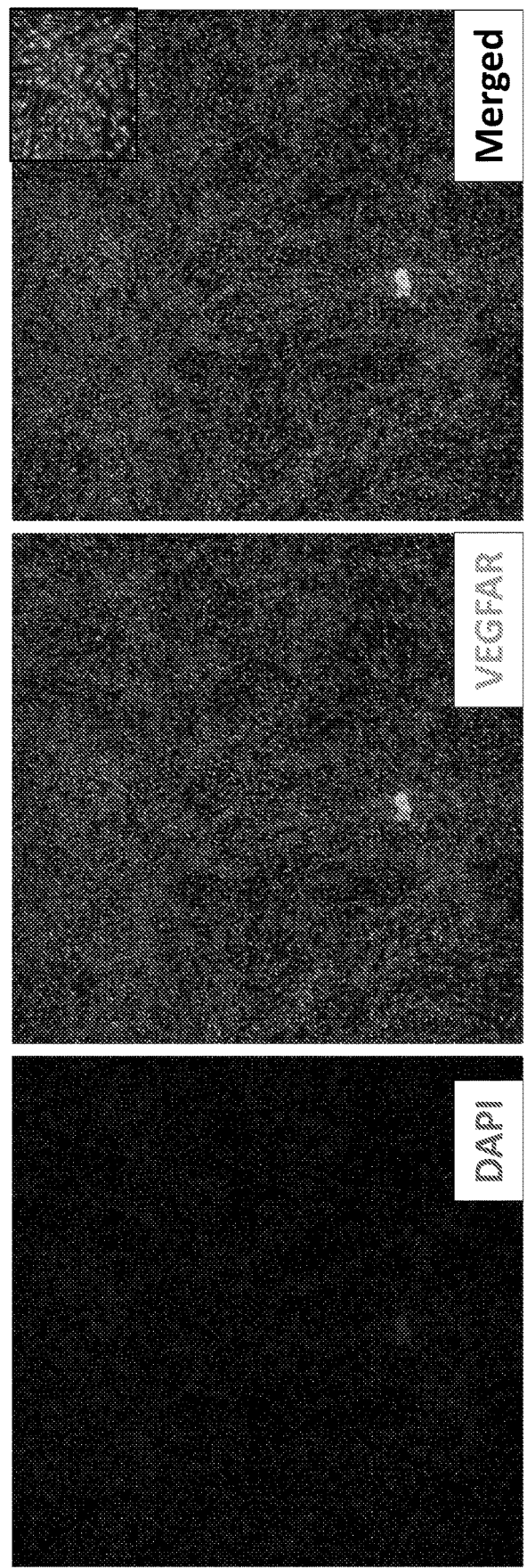

FIG. 45. Images of 20 days differentiation. DAPI and ICC for VEGFAR (20 days of differentiation).

FIG. 46. Co-culture of i-Islets with i-Endo cells in transwell plates. Introduce i-Endo cells during Pancreatic Progenitors and maturation of i-Islets phases.

Figure 47:
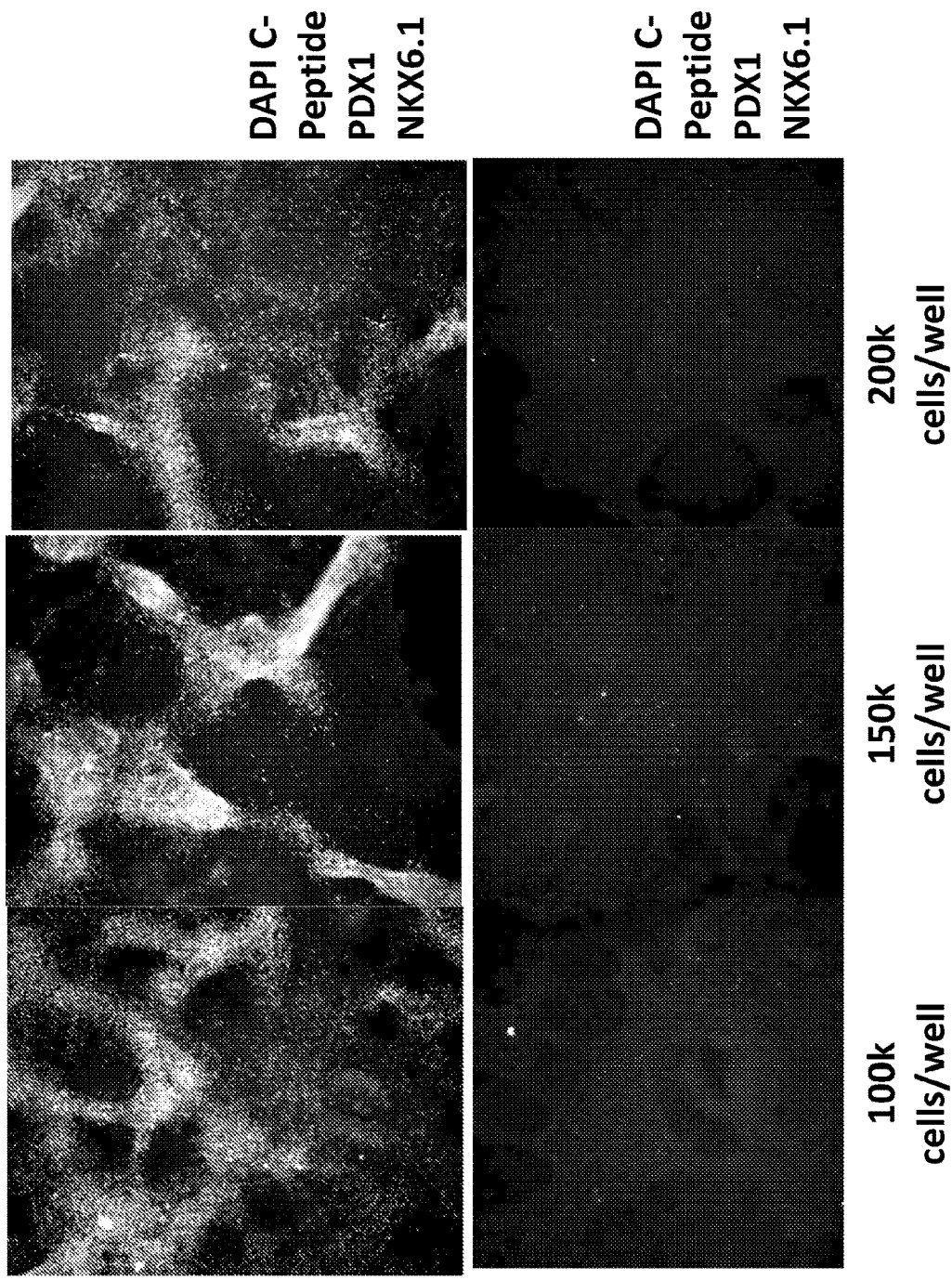

FIG. 47. Expression of DAPI, C-Peptide, PDX1 and NKX6.1 in co-culture of islet cells with HUVECs at different seeding densities.

Figure 48:
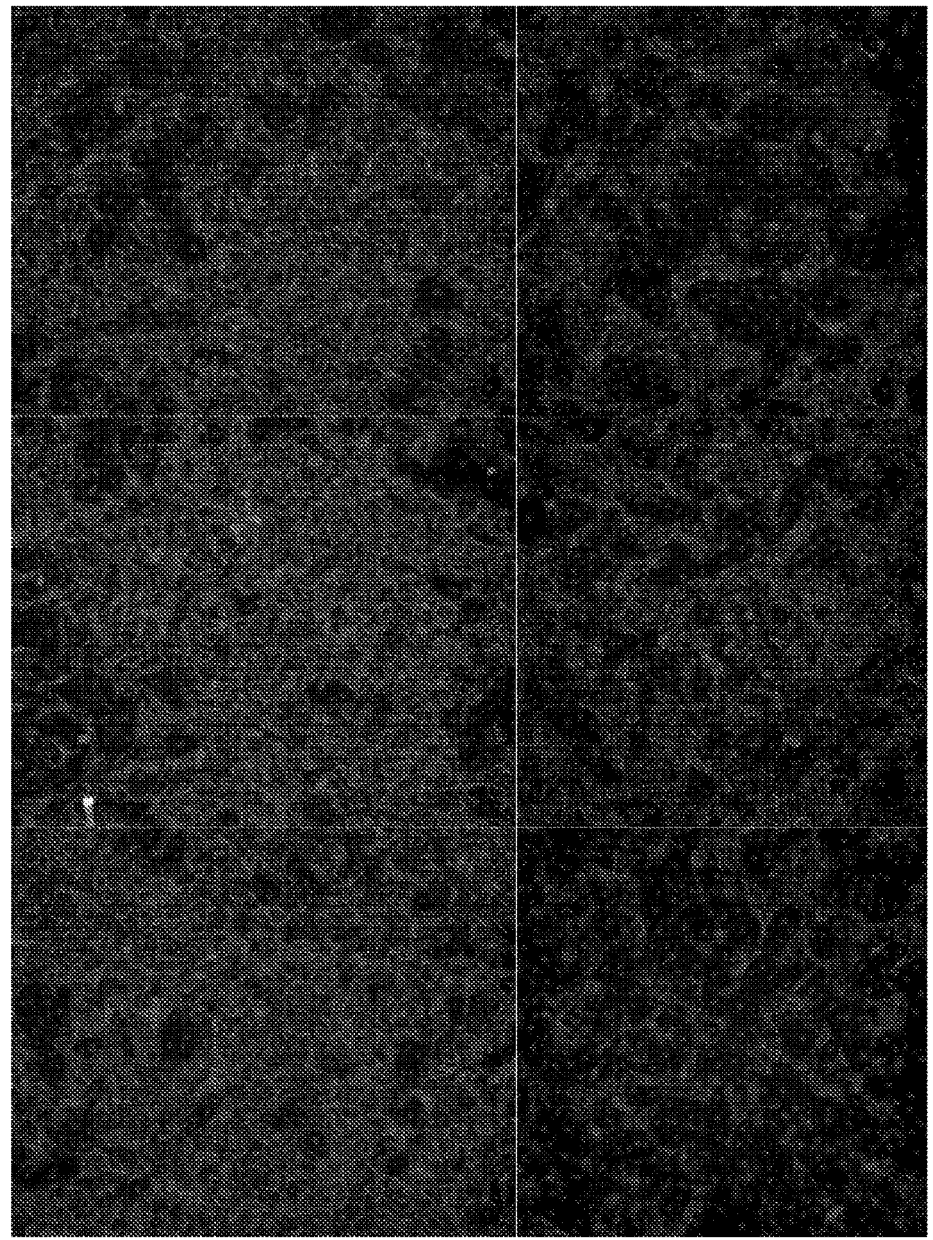

FIG. 48. Expression of DAPI and CD31 in co-culture of islet cells with HUVECs at different seeding densities.

FIG. 49. HUVECs on PET inserts. i-Islets on bottom (SLiP media). HUVECs introduced on Stage 6 of i-Islets differentiation (maturation of islets).

Figure 50:
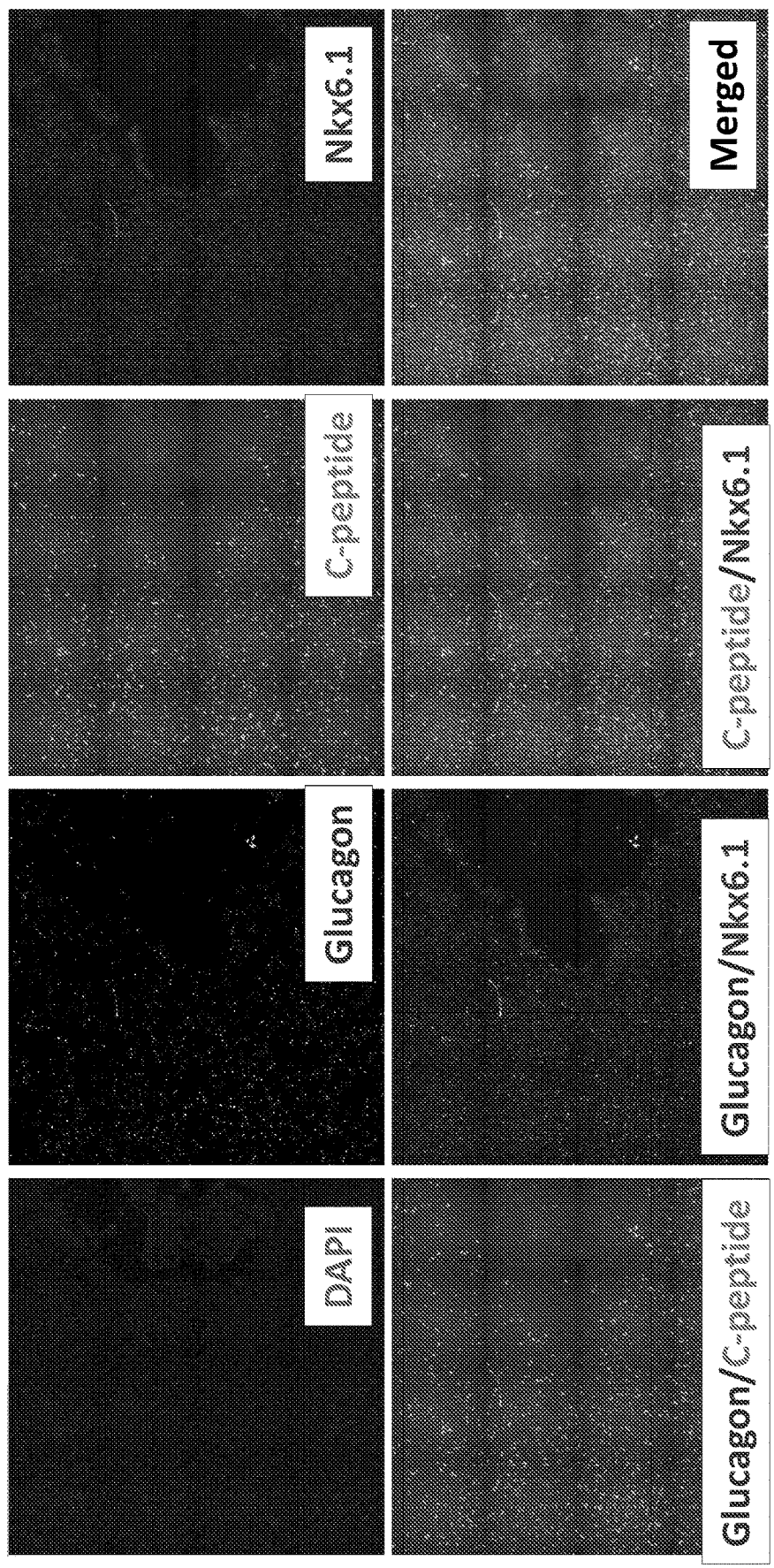

FIG. 50. Expression of DAPI, Glucagon, C-Peptide, PDX1 and NKX6.1 in islet only culture.

Figure 51:
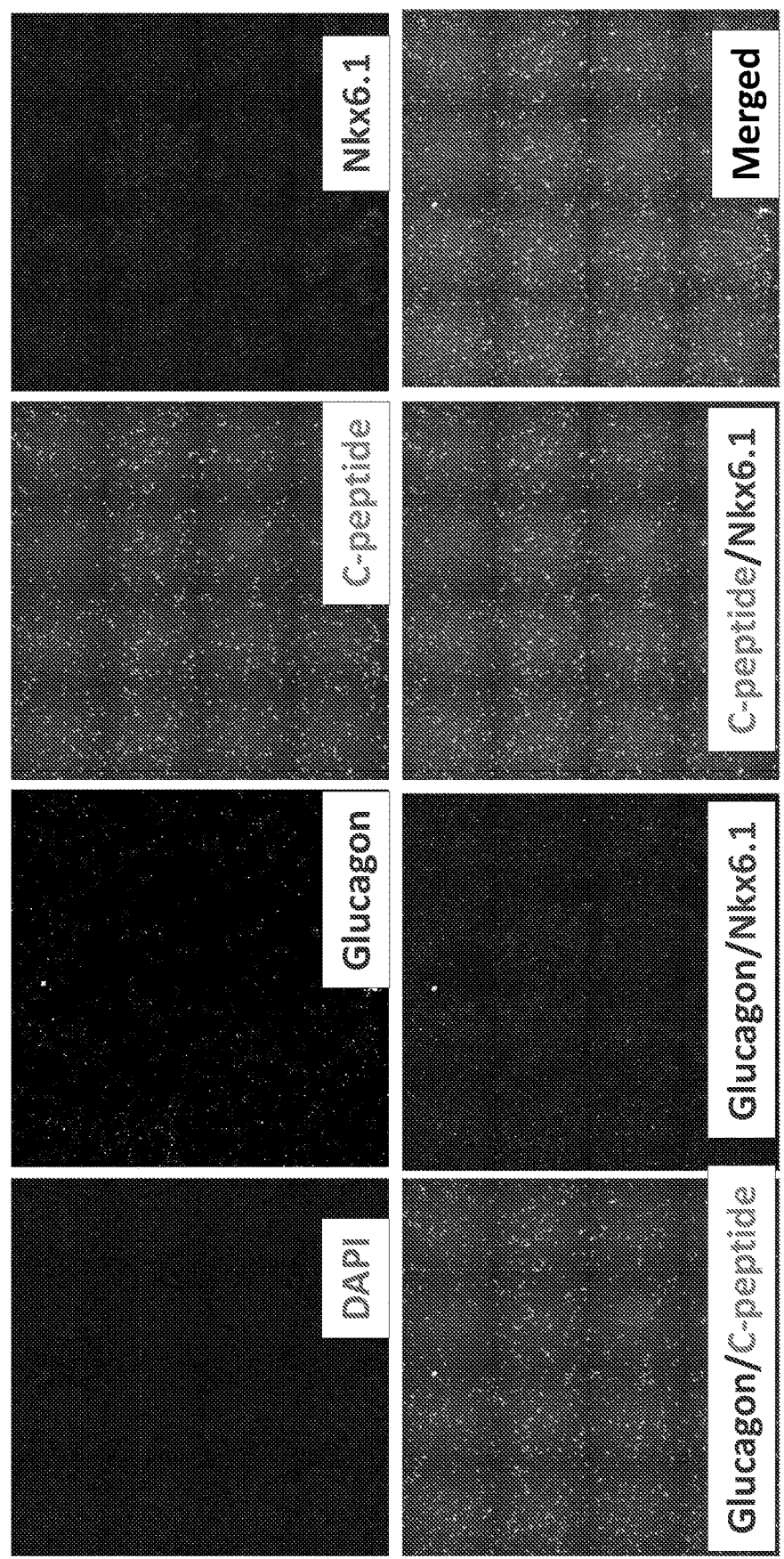

FIG. 51. Expression of DAPI, Glucagon, C-Peptide, PDX1 and NKX6.1 in islet and HUVEC co-culture.

Figure 52:
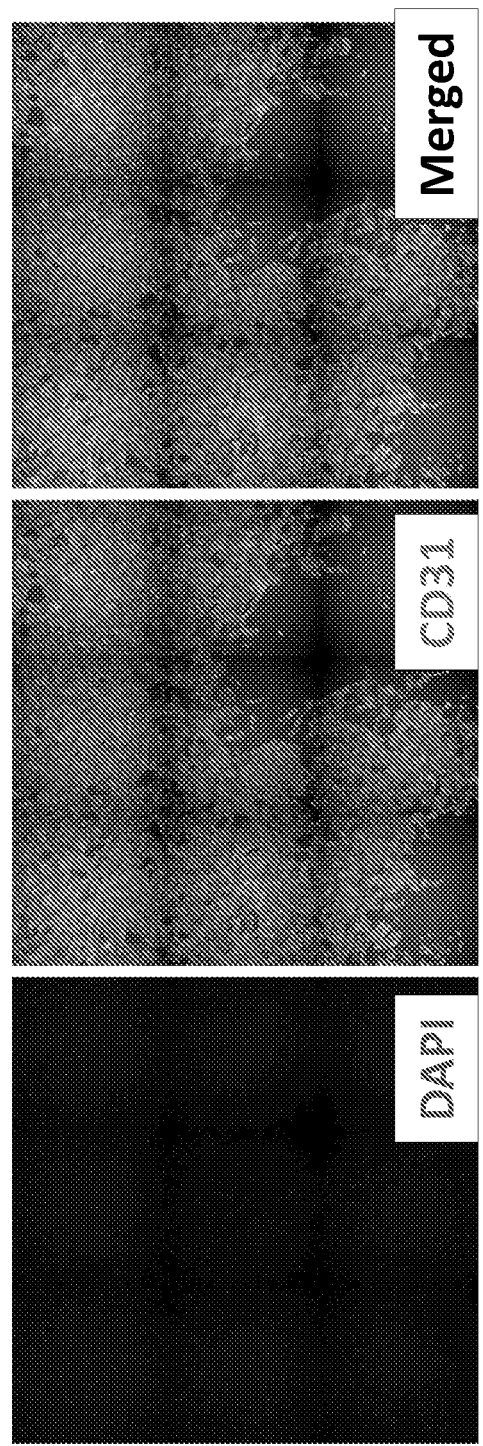

FIG. 52. Expression of DAPI and CD31 in islet and HUVEC co-culture.

Figure 53:
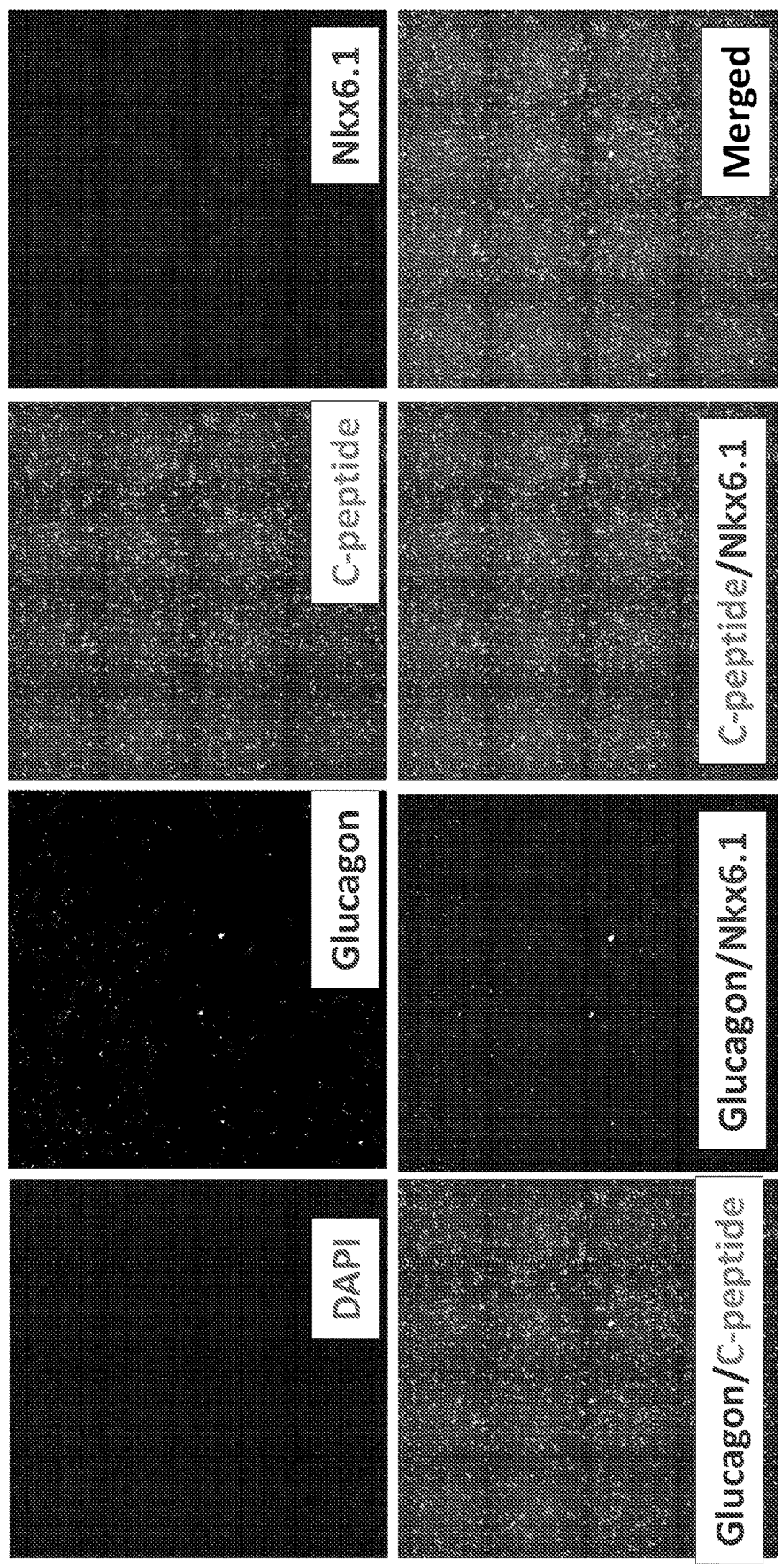

FIG. 53. Expression of DAPI, Glucagon, C-Peptide, PDX1 and NKX6.1 in islet and HUVEC co-culture.

Figure 54:
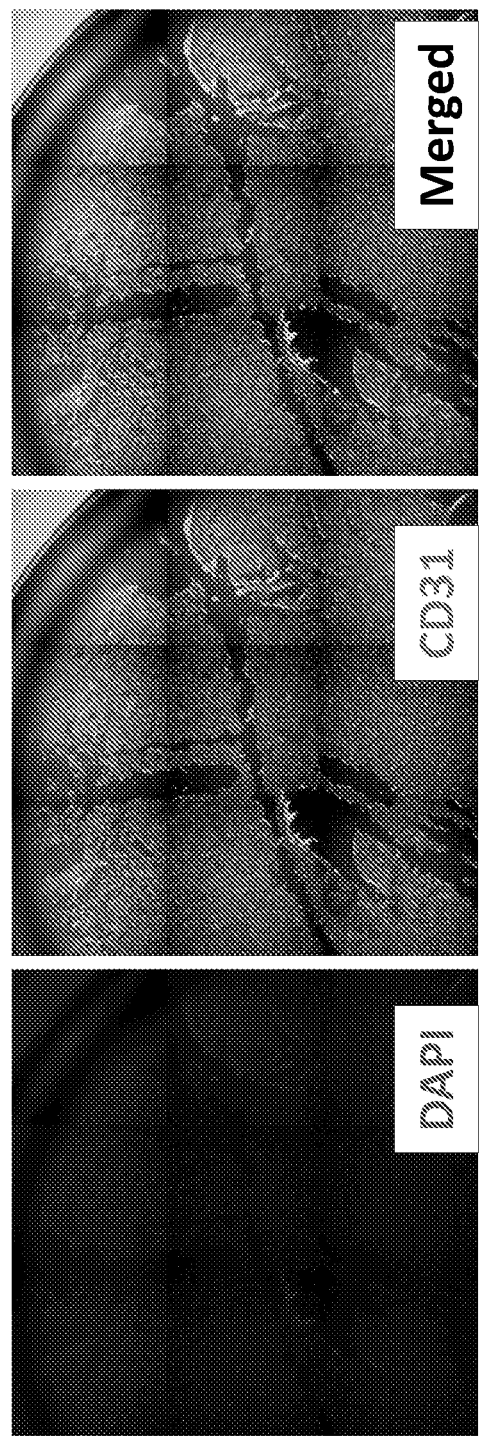

FIG. 54. Expression of DAPI and CD31 in islet and HUVEC co-culture.

DEFINITIONS

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, NY 2006); and Sambrook and Russel, *Molecular Cloning: A Laboratory Manual* 4$^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Some abbreviations are used herein.

The term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel. Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the organ-chip is intended for therapeutic application. Examples of applications that may make advantage of larger fluidic devices include the use of the device for the generation of highly differentiated cells (e.g. the device can used to drive cell differentiation and/or maturation, whereupon the cells are extracted for downstream use, which may include implantation, use in an extracorporeal device, or research use), or use of the device for implantation or extracorporeal use, for example, islet on chip, endothelial vascular cell on chip, skeletal muscle chip, or combination of the aforementioned cells (e.g., islet-vascular cells in channels on the chip, islet-muscle cells in channels on the chip). Unlike conventional static cultures, the present invention contemplates microfluidic devices where the cells are exposed to a constant flow of media providing nutrients and removing waste.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

DETAILED DESCRIPTION

Figure 1:
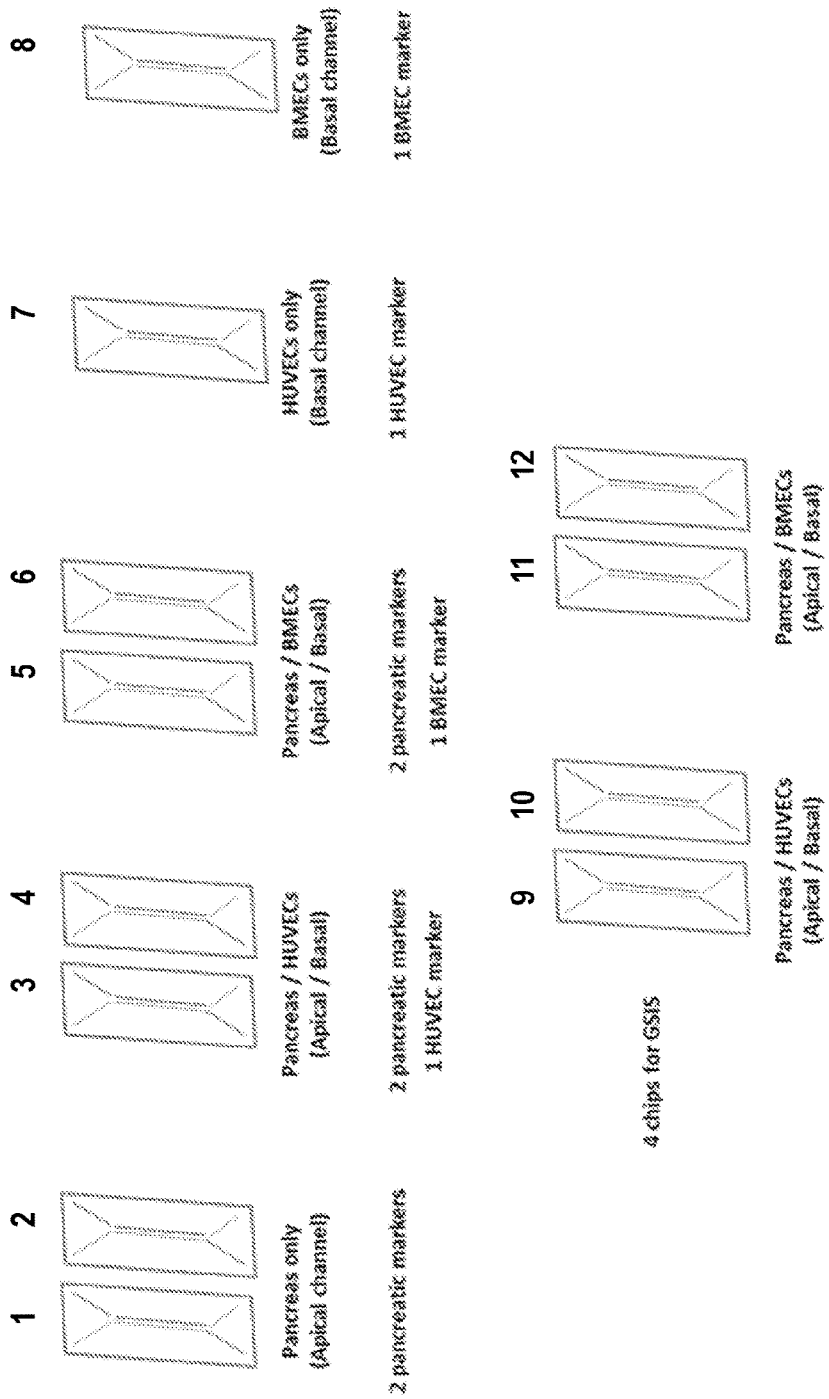
FIG. 1. Experimental design.
Figure 2:
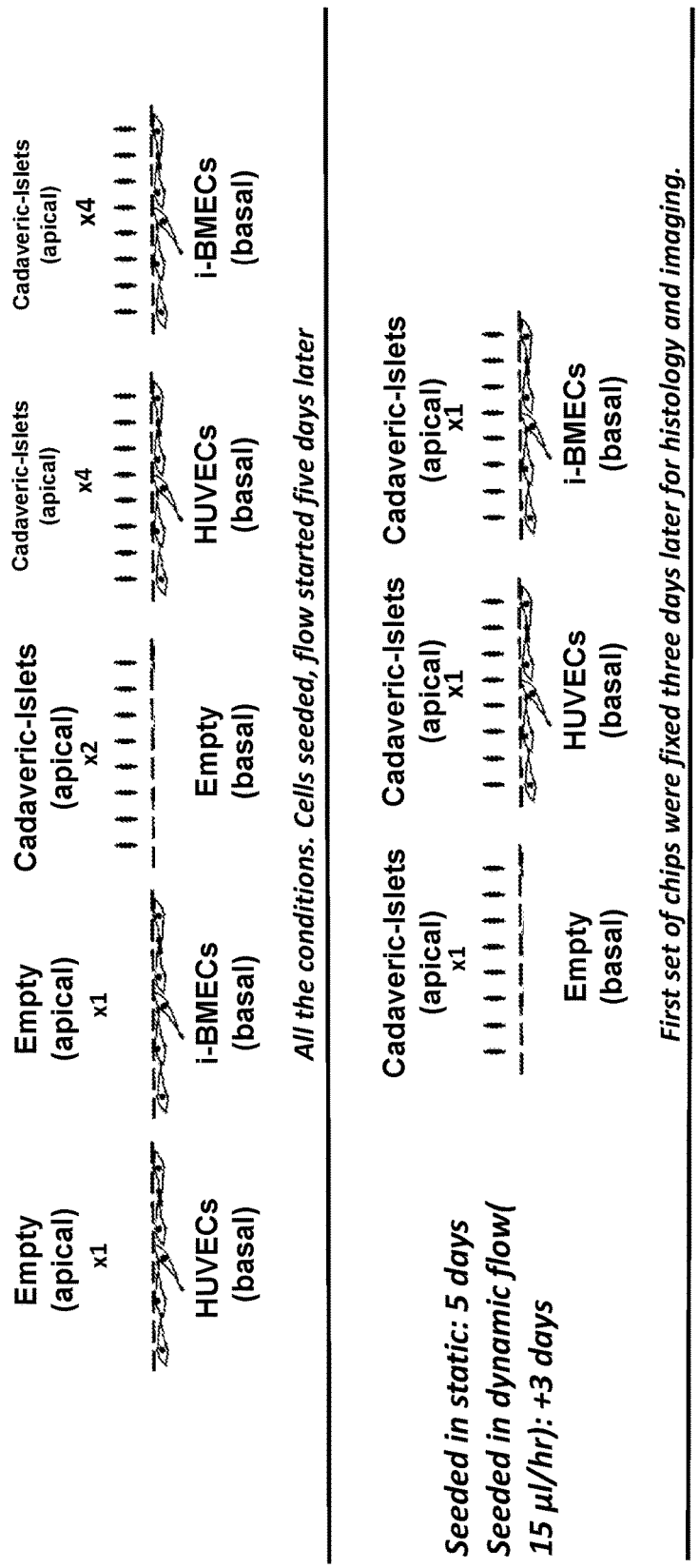
FIG. 2. Experimental design. All the conditions. Cells seeded, flow started five days later First set of chips were fixed three days later for histology and imaging. Second set of co-culture chips were fixed four days later for histology and imaging. Remaining chips are being processed for GSIS assay.

T2D is a common clinical syndrome defined by hyperglycemia due to insufficient insulin secretion in the setting of relative insulin resistance. Insulin sensitivity varies widely in non-diabetic individuals with accumulation of mesenteric fat being a major determinant of insulin resistance in skeletal muscle, fat and the liver. Hypotheses that link obesity with insulin resistance include cytokines released from activated macrophages, altered alterations in lipid composition and, with aging, decreased density of motor neuron innervation. Hypotheses that link obesity with insulin resistance include cytokines released from activated macrophages, altered lipid composition and, with aging, decreased density of motor neuron innervation. Hypotheses that link β-cell dysfunction in T2D include protein misfolding, glucolipotoxicity, dedifferentiation and immune cell released cytokines. In health, variance in insulin sensitivity is offset by adaptive changes in glucose stimulated insulin secretion, both of which can be evaluated under conditions of daily living by the mixed meal minimal model test. T2D may occur because of a modest defect in insulin secretion in the context of marked insulin resistance (IR-T2D) or a marked defect in insulin secretion in the setting of a modest defect in insulin sensitivity (β-T2D) (FIG. 1). Because of inaccessibility to relevant human organs, drug discovery and mechanistic studies of β-cell dysfunction and insulin resistance in T2D have relied largely on rodent models such as those with defective leptin signaling. These models have been poorly predictive of disease mechanisms or drug efficacy in humans, contributing to the high cost of drug development. Moreover, inbred rodent models fail to reproduce the wide range of relative defects in insulin secretion and insulin sensitivity in humans with T2D that predictably require different therapeutic approaches targeted predominantly to β-cell preservation and function versus insulin action. Therefore, development of human Organ-chip models representative of the range of T2D types would overcome a major obstacle in evaluating disease mechanisms and provide a more relevant drug screening tool.

As such, described herein are compositions and methods for microphysiological MPS models of disease (MODs) for β-T2D and IR-T2D. These platforms allow one to compare the effect of chronic β-cell stimulation (best characterized risk factor for β-cell failure in T2D) in the presence and absence of patient specific immune cells in IPSC-derived islets from each group. This approach will recapitulate protein misfolding and stress metabolic changes that are the hall mark of β-cell dysfunction in T2D. If necessary to reproduce the T2D β-cell phenotype, the islets-on-chips will also be exposed to gluco-lipotoxicity. Likewise, skeletal muscle-on-chips will be exposed to patient specific activated immune cells, variable motor neuron innervation and lipids characteristic of T2D.

Using the systems, the Inventors have uncovered cross talk between islets and vascular endothelium. That is to say, the presence of vascular endothelial cells in the microfluidic device improves the islet cell functionality, as measured by (for example) insulin secretion. The Inventors have selected skeletal muscle as the second organ-chip since iPSC-derived skeletal muscle is better developed than liver or fat, and the Inventors have considerable experience with this tissue.

Described herein is a method of generating pancreatic progenitor cells, including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the definitive endoderm express one or more of CXCR, SOX17, or both. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1. In other embodiments, the method includes culturing immature endocrine cells in the presence of T3, Alk5i, R428 and NAC for about 7 days to generate mature endocrine cells. In other embodiments, the mature endocrine cells express one or more of: C-peptide, glucagon and MafA. In various embodiments, the immature endocrine cells are islet cells. In various embodiments, the islet cells are beta islet cells. In other embodiments, the islet cells are capable of producing insulin. In other embodiments, the islet cells secrete insulin C-peptide. In other embodiments, the islet cells are glucose responsive. In other embodiments, the islet cells express one or more of: proinsulin, insulin, glucagon, somatostatin and PDX-1, and Nkx6.1. In other embodiments, the cell capable of producing insulin expresses one or more markers selected from the group including proinsulin, insulin, glucagon, somatostatin and PDX-1, and Nkx6.1. In other embodiments, the iPSCs derived from a diabetic subject. In various embodiments, small molecules such as CHIR990021, R428, etc. are added at a concentration of about 0.05-0.1 µM, 0.1-1 µM, 1-5 µM, 5-10 µM, 10-25 µM, 25-50 µM, 50-100 µM or 100 µM or more. In various embodiments, growth factors such as Activin A, FGF 10, EGF, etc. are added at a concentration of about 0.05-0.1 ng/ml, 0.1-1 ng/ml, 1-5 ng/ml, 5-10 ng/ml, 10-25 ng/ml, 25-50 ng/ml, 50-100 ng/ml, 100-250 ng/ml or 250 ng/ml or more.

Described herein is a quantity of pancreatic progenitor cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both.

Described herein is a quantity of endocrine progenitor cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells.

Described herein is a quantity of immature endocrine cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1.

Described herein is a quantity of mature endocrine cells made by a method including culturing induced pluripotent stem cells (iPSCs) in the presence of Activin A and CHIR99021 for about 3 days to generate definitive endoderm, culturing definitive endoderm in the presence of FGF10, Noggin, and CHIR 99021 for about 2 days to generate gut tube endothelium, culturing gut tube endothelium in the presence of FGF10, Noggin, Sant1 and retinoic acid for about 4 days to generate pancreatic progenitor cells. In other embodiments, the pancreatic progenitor cells express PDX1+, NKX6.1+, or both. In other embodiments, the method includes culturing pancreatic progenitor cells in the presence of EGF, nicotinamide, and Noggin for about 4 days to generate endocrine progenitor cells. In other embodiments, the method includes culturing endocrine progenitor cells in the presence of T3, Alk5i, and Noggin for about 7 days to generate immature endocrine cells. In other embodiments, the immature endocrine cells express one or more of: C-peptide, glucagon and NKX6.1. In other embodiments, the method includes culturing immature endocrine cells in the presence of T3, Alk5i, R428 and NAC for about 7 days to generate mature endocrine cells. In other embodiments, the mature endocrine cells express one or more of: C-peptide, glucagon and MafA. In other embodiments, the immature endocrine cells are islet cells. In other embodiments, the mature endocrine cells are islet cells. In other embodiments, the islet cells are beta islet cells. In other embodiments, the islet cells are capable of producing insulin. In other embodiments, the islet cells secrete insulin C-peptide. In other embodiments, the islet cells are glucose responsive.

Described herein is a method of generating endothelial cells, including culturing (iPSCs) in the presence of CHIR99012 for about 2 days to generate mesoderm, culturing mesoderm in the presence of BMP4, VEGF, and FGF2 for about 2 days to generate vascular progenitor cells, culturing vascular progenitors in the presence of EGM-MV2 and VEGF for about 4-6 days to generate endothelial progenitor cells, and culturing endothelial progenitor cells in the presence of EGM-MV2 and VEGF to generate endothelial cells. In various embodiments, the vascular progenitors are cultured in the presence of EGM-MV3 and VEGF, and passages 2, 3, 4 or more times to generate endothelial cells. In other embodiments, the vascular progenitor cells express one or more of: CD31+, CD34+, VEGF+, and VEGFA+ at day 20.

Also described herein is a quantity of endothelial cells made by a method of generating endothelial cells, including culturing (iPSCs) in the presence of CHIR99012 for about 2 days to generate mesoderm, culturing mesoderm in the presence of BMP4, VEGF, and FGF2 for about 2 days to generate vascular progenitor cells, culturing vascular progenitors in the presence of EGM-MV2 and VEGF for about 4-6 days to generate endothelial progenitor cells, and culturing endothelial progenitor cells in the presence of EGM-MV2 and VEGF to generate endothelial cells. In other embodiments, the vascular progenitor cells express one or more of: CD31+, CD34+, VEGF+, and VEGFA+ at day 20.

Described herein is a method of co-culturing islet cells with endothelial cells. In various embodiments, the method includes a) providing i) islet cells and endothelial cells, and ii) a microfluidic device including a membrane, said membrane including first and second surfaces; b) seeding islet cells on said first surface of said membrane so as to create seeded islet cells; c) seeding endothelial cells on said second surface of said membrane so as to create seeded endothelial cells; and d) exposing said seeded cells to a flow of culture media for a period of time so as to create perfused cells. In various embodiments, the method includes the step of e) culturing said perfused cells. In various embodiments, steps b) and c) are performed in any order or together. In various embodiments, step c) is performed before step b). In various embodiments, culturing of said perfused cells under conditions of flow results in increased islet cell functionality. In various embodiments, the islet cells are induced islet cells. In various embodiments, the islet cells are human cadaveric islet cells. In various embodiments, the islet cells are beta islet cells. In various embodiments, the method includes the step of stimulating said perfused cells with glucose so as to create stimulated cells. In various embodiments, the method includes the step of detecting insulin secretion by said stimulated cells. In various embodiments, the method includes measuring insulin secretion by said stimulated cells, wherein the amount of insulin secretion is higher in the presence of said endothelial cells as compared to the absence of said endothelial cells. In various embodiments, measuring insulin secretion by said stimulated cells, wherein the amount of insulin secretion is higher in the presence of said flow as compared to the absence of said flow. In various embodiments, the islet cells are derived from a subject with a disorder or disease. In various embodiments, the islet cells are derived from a diabetic subject. In various embodiments, the diabetic subject is a neonate. In various embodiments, culturing results in a more mature islet cell phenotype. Described herein are methods and compositions for culturing cells in a fluidic device.

In various embodiments, the cells are islet cells (i.e., islet-on-chip). In various embodiments, the cells are endothelial cells such as brain microvascular endothelial cells (BMECs-on-chip). In various embodiments, the cells are muscle cells (i.e., muscle cells-on-chip). Further information is on organ chip is found in Sances, et al. Human iPSC-derived endothelial cells and microengineered Organ-Chip enhance neuronal development. Stem Cell Reports In press, (2018), which is incorporated by reference herein.

In one embodiment, the present invention contemplates a islet-on-chip where at least one population of cells is derived from a patient diagnosed with a metabolic disorder, including diabetes and insulin resistance. In one embodiment, the islet cells are cells obtained from a subject diagnosed with diabetes. In various embodiments, diabetes includes lean and obese diabetic subjects. In one embodiment, the present invention contemplates generating induced pluripotent stem cells (iPSCs). In various embodiments, the iPSCs are differentiated into islet cells. In one embodiment, the iPSCs are from subjects with diabetes and differentiating them into islet cells. In various embodiments, the iPSCs are differentiated into muscle cells. In various embodiments, the iPSCs are differentiated into endothelial cells, such as iBMECs.

It is contemplated that iPSC technology can be used together with microfluidic chips to mimic patient-specific phenotypes in disease states. Thus, in one embodiment, iPSCs derived islet cells such as beta cells, are derived from a patient diagnosed with or at risk for a disease. In one embodiment, the patient has a metabolic disease such as diabetes. In one embodiment, the patient has a mutation. This includes for example, mutant KCNJ11. Further information on iPSC reprogramming is found in Barrett, R. et al. Reliable Generation of Induced Pluripotent Stem Cells From Human Lymphoblastoid Cell Lines. Stem Cells Transl. Med. (2014), which is incorporated by reference herein.

In various embodiments, is a method of differentiating a human pluripotent stem cell into an endodermal lineage cell, including for example, a cell capable of producing insulin, such as beta cells. The method includes providing a quantity of human iPSCs, culturing the pSCs in the presence of at least one differentiation agent, optionally including at least one extracellular matrix (ECM) component, wherein the at least one differentiation agent is capable of producing insulin. In another embodiment, the at least one first differentiation agent includes activin A and wingless-related MMTV integration site 3A (WNT3A). In another embodiment, the method includes culturing the pSCs in the presence of at least one second differentiation agent, such as all-trans retinoic acid (RA) and keratinocyte growth factor (KGF). In another embodiment, further culturing of the pSCs is in the presence of at least one third differentiation agent, and optionally at least one fourth differentiation agent. Examples of additional differentiation agents include insulin growth factor, epidermal growth factor (EGF), hepatocyte growth factor (HGF), insulin-like growth factor (IGF1), exendin-4 and nicotinamide. In various embodiments, the differentiation agents include molecules capable of modulating the BMP, WNT, and Activin-signaling pathways. This includes, for example, BMP-2, and BMP-4. In other embodiments, the at least one differentiation agent is provided an endothelial cell culture in fluidic communication with the differentiating and differentiated iPSCs.

In another embodiment, the cell capable of producing insulin is a definitive endoderm (DE) lineage cell. In another embodiment, the DE cell expresses CXCR, SOX17, or both. In another embodiment, the cell capable of producing insulin expresses one or more markers selected from the group including: proinsulin, insulin, glucagon, and somatostatin. Other markers include, for example, PDX-1, Ngn3, GLUT2, GKS, SUR1, Nkx6.1 and Kir6.2. In another embodiment, the cell capable of producing insulin is responsive to glucose. In another embodiment, the cell capable of producing insulin secretes C-peptide. In another embodiment, the cell capable of producing insulin can be expanded in vitro. In another embodiment, the cell capable of producing insulin is a beta-cell.

More specifically, the embodiments described herein show that functional islet-on-chip, are responsive to when cultured with an additional cell, such as endothelial cells including iBMECs. In various embodiments, this includes glucagon response, c-peptide expression, and insulin secretion as examples.

In various embodiments, islet-on-chip, in one embodiment, includes islet cells, e.g. patient iPSC-derived islets combined with a human skeletal muscle-on-chip. In various embodiments, islet-on-chip, in one embodiment, includes a islet cells, e.g. patient iPSC-derived islets combined with a endothelial cells-on-chip. For example, islet cells can be seeded into an upper channel, with muscle cells or endothelial cells seeded into the lower channel of a 2-channel microfluidic chip. Alternatively, in other embodiments, one can combine the 2 chips, i.e. islet cells-on-chip and skeletal muscle cell-on-chip.

In various embodiments, the iPSC-derived cells, including two cell types in a single chip or two cell types in multiple chips in fluidic communication, include combinations of both cell types derived from a single subject, including a diseased subject, or one of the cell types each derived from a disease and healthy subject.

Described herein is culturing islet cells together with other cell types in a fluidic device. In one embodiment, the present invention contemplates a method of culturing cells, including: a) providing a microfluidic device including a membrane, said membrane including a top surface and a bottom surface; b) seeding induced islet cells on said top surface and skeletal muscle cells on said bottom surface so as to create seeded cells; c) exposing said seeded cells to a flow of culture media for a period of time; and d) culturing said seeded cells.

It is not intended that the present invention be limited to situations where both islet and skeletal muscle cells are seeded together. In one embodiment, the present invention contemplates a method of culturing cells, including: a) providing a microfluidic device including a channel; b) seeding skeletal muscle cells into said channel; c) inducing said skeletal muscle cells to differentiate; and d) detecting myo-fiber formation. Islet cells can be (optionally) added before or after the muscle cells (or not at all).

The present invention also contemplates seeding on both patterned surfaces and/or gels. In one embodiment, the present invention contemplates a method of culturing cells, including: a) providing a microfluidic device including a patterned surface and a gel, b) seeding induced motor neuron cells on said patterned surface and skeletal muscle cells on said gel. In one embodiment, said skeletal muscle cells and/or said islet cells are exposed to a flow of culture media for a period of time.

For example, iPSC-derived islet cells are generated are seeded in the apical channel ($3 \times 10^3$ cells/µL; 28 µl resident, 8 µl dead volume) and iPSC-derived endothelial cells in the basal channel ($3 \times 10^4$ cells/µL; 5.5 µl resident, 10 µl dead volume) of plasma-activated fibronectin/laminin coated PET and PDMS-based organ-chip devices. One-day post-cell attachment, media flow is initiated and varied between a rate 150-100 µL/hour in the apical channel and 30 µL/hour in basal channel. The cells can be analyzed via GSIS assay and/or IHC. Insulin secretion are evaluated 2 days and then again 5 days after iPSC were seeded on chips measuring glucose concentrations at 4 and 12 mM glucose. Glucose activation of β-cells mean cellular Ca' will also be evaluated in real time at 4 and 12 mM glucose by in-chip calcium imaging using the fluo-4 and fura-2 AM indicator dye.

The present invention also contemplates microfluidic devices with cells. In one embodiment, the present invention contemplates a microfluidic device including a) a membrane, said membrane including a top surface and a bottom surface; and b) iPSC-derived cells. In various embodiments, iPSC-derived islet cells such as beta cells are on said top surface and skeletal muscle cells on said bottom surface. In one embodiment, said induced motor islet cells are derived from induced pluripotent stem cells from a human. In one embodiment, said human is diagnosed with a metabolic disease including diabetes. In various embodiments, diabetes includes lean and obese diabetic subjects. In one embodiment, said membrane includes covalently attached ECM protein(s).

The present invention also contemplates systems including microfluidic devices with cells under flow conditions. In one embodiment, the present invention contemplates a system including a microfluidic device, said microfluidic device including a) a membrane, said membrane including a top surface and a bottom surface; and b) one cell type on said top surface and a different cell type on said bottom surface, wherein either one of said cell types or both are exposed to culture media at a flow rate. In various embodiments, this includes b) induced islet cells such as beta cells on said top surface and skeletal muscle cells on said bottom surface, In one embodiment, said islet cells are derived from induced pluripotent stem cells from a human. In one embodiment, said human is diagnosed with a metabolic disease, including diabetes. In one embodiment, said membrane includes covalently attached ECM protein(s). In one embodiment, the membrane is in a channel, said channel is in fluidic communication with a reservoir including culture media.

Described herein is a method of compound screening using the aforementioned microfluidic devices. For example, a system including a microfluidic device, said microfluidic device including a) a membrane, said membrane including a top surface and a bottom surface; and b) one cell type on said top surface and a different cell type on said bottom surface, wherein either one of said cell types or both are exposed to culture media at a flow rate. Addition of a compound of interest to culture media can alter one or more properties of one or more cell types in the microfluidic device.

In various embodiments, this includes b) induced islet cells such as beta cells on said top surface and skeletal muscle cells on said bottom surface, In one embodiment, said islet cells are derived from induced pluripotent stem cells from a human. In one embodiment, said human is diagnosed with a metabolic disease, including diabetes. In one embodiment, said membrane includes covalently attached ECM protein(s). In one embodiment, the membrane is in a channel, said channel is in fluidic communication with a reservoir including culture media. For example, one can conduct dose response experiments for selection of 3 phenotype reversing drug candidates.

Additionally, the compound of interest can be added to evaluate compounds of interest added into endothelial side of channel, thereby identifying candidates capable of penetrating the endothelial cell layer of the chips, and into islet and/or muscle cell compartment.

Further described herein is a quantity of iPSC cells derived from a subject with a metabolic disease, such as diabetes. In various embodiments, the iPSC cells are reprogrammed according the aforementioned methods, including those described in Sareen et al. Further described herein is a quantity of iPSC-derived cells, including differentiated cells such as endoderm lineage cells, including definitive endoderm, pancreatic lineage, islet cells and beta cells. Other differentiated cells include muscle and endothelial cells, such as skeletal muscle, brain microvascular endothelial cells and vascular endothelial cells.

Further information is found in U.S. application Ser. Nos. 15/458,185, 15/352,289, PCT App. No. PCT App. No. PCT/US2017/49115, PCT App. No. PCT/US2017/49193, PCT App. No. PCT/US2017/16079, PCT App. No. PCT/US2017/16098, PCT App. No. PCT/US2017/16079, PCT App. No. PCT/US2017/16098, PCT App. No. PCT/US2017/016098, PCT App. No. PCT/US2017/16079, PCT App. No. PCT/US2018-022511, PCT App. No. PCT/US2016/57724, and PCT App. No. PCT/US2017/49115, each of which is incorporated by reference herein.

EXAMPLES

Below are non-limiting examples.

Example 1

Patient Recruitment and Characterization

The Inventors have already established iPSCs from 7 non obese (BMI<27 kg/m$^2$) patients with T2D who require insulin therapy (β-T2D) and have been characterized by the mixed meal minimal model to measure both β-cell function and insulin sensitivity. Additional studies can involve recruitment of 10 obese patients (BMI>30 kg/m$^2$) with T2D (auto-antibodies negative) with fasting C-peptide greater than 3 ng/mL that despite insulin sensitizer therapy require more than 1.5 units insulin/kg/day (IR-T2D). Age and BMI matched non diabetic controls are utilized for both T2D groups. The Inventors will perform the mixed meal minimal model test for IR-T2D and both control groups to measure insulin sensitivity and (3-cell function and obtain blood for iPSC derivation from white blood cells as already accomplished for the β-T2D group. Blood will also be obtained to generate iPSCs from the 8 patients with well characterized monogenic neonatal diabetes due to KCNJ11 and IR mutations. Additional blood samples will be obtained from the study volunteers on an as needed basis to obtain circulating immune cells to apply to the organ-chips.

Example 2 iPSC Derivation: Human iPSC Lines from Healthy Controls and Diabetic Donors

The Inventors utilize non-integrating oriP/EBNA1-based episomal plasmid vectors to generate integration-free iPSC lines from PBMCs[1-6]. They do not suffer from the "footprint" problem from exogenous reprogramming factor DNA experienced with other techniques and have remarkable cytogenetic stability compared to other reprogramming approaches. The Inventors' PBMC-based episomal reprogramming approach results <5% of karyotypically abnormal iPSC lines during early passage (<p10), and under <2% upon repeat karyotyping at higher passages (>p10).

All iPSC lines are characterized with rigorous certificate of analysis; iPSCs with typical pluripotent stem cell morphology, high nuclear-to-cytoplasmic ratio, expression of pluripotency markers, a normal karyotype, PluriTest assay, and no detectable exogenous reprogramming factor expression of. This includes multiple PBMC-derived iPSC lines from healthy volunteers and diabetic patients some of which have already been fully-characterized. All iPSC lines are maintained on defined mTeSR/E8 media on either of human recombinant L521 substrate or BD Matrigel™ Matrix.

Example 3

Organ-Chips System

Organ-chips model human biology by reconstructing microenvironments more closely resembling in vivo than conventional culture. For example, the Inventors have shown that human iPSC-derived endothelial cells and micro engineered organ-chip enhance neuronal development. Given that endothelium is a key component, results using a new diabetes organ-chip program incorporating endothelial cells and demonstrate the influence vascular endothelium on islet maturation and function.

The microfluidic channels are lined with living human cells. organ-chips are made from transparent polymers. The organ-chips are designed to represent the smallest functional unit of the corresponding organ. The chip's fluid channels mimic blood flow while its transparency allows study of organ function in real time. The chips include two channels—an apical and a basal channel. The apical channel is 1 mm tall and 1 mm wide, while the basal channel is 200 μm tall and 1 mm wide. These two channels are separated by a polymer membrane, composed of polyethylene terephthalate (PET) or poly(dimethylsiloxane) (PDMS), that are 10 μm thick and patterned with 7 μm pores. The apical channel, the membrane and the basal channel are plasma bonded to form a complete chip. Each channel can be populated with different cell types to investigate cellular interactions. Medium can flow through both channels to deliver drug screens or immune cells.

Example 4

Primary Human Islets and iPSC Development of Pancreatic Islets

The Inventors procure primary human islets from brain dead organ donors through the NIH human islets consortium. For i-Islets, the Inventors have established the Melton differentiation protocol and successfully generated functional i-Islets based on cellular composition, glucose induced insulin secretion by periperfusion and after transplant into mice. Briefly, suspension-adapted T2D patient and control iPSCs (Oct4 >90%) will be directed to definitive endoderm using a high concentration Activin A (100 ng/mL) alongside GSK313 inhibitor, CHIR99021. Next, KGF (FGF7) is added over 3 days to induce foregut formation and Pdx1 expression. To direct the clusters towards pancreatic endocrine progenitors, the suspension clusters will be cultured in KGF, LDN193189 (BMP signaling inhibitor, retinoic acid (caudalizing agent), SANT1 (Shh signaling inhibitor), PDBU (activator of protein kinase C). In the next stage, Activin A is added back to the cocktail. The final stages (Stage 4-6) of differentiation include β-cellulin (member of the EGFR family), γ-secretase inhibitor (XXI), ALK5 inhibitor (Alk5i) and thyroid hormone T3. At the end of Stage 5 of differentiation the floating clusters are dissociate and reaggregated to enrich for chromogranin A (CHGA)$^+$, Nkx6.1+, C-peptide$^+$ i-Islet clusters. Floating clusters from reaggregated i-Islets will be harvested and seeded in organ-chips. The cell health status of all clusters will be determined by counting viable cells upon dissociation and LDH assay. All stage-specific markers will be quantified by flow cytometry.

Example 5 i-Islets and Primary Human Islets on Chip

The vascular circulatory system is a fundamental architecture that supplies oxygen and nutrients to all cells and helps in maintaining homeostasis of various tissues and organs. The Inventors seeded partially dissociated non-diabetic human islets on the apical channel and endothelial cells from two sources (iPSC derived brain microvascular endothelial cells (iBMECs) or human umbilical vein endothelial cells (HUVECs)) on the basal channel of microfluidic chips. Endothelial cells were seeded 10-24 hours prior to the seeding of the islets. Media flow was initiated on day 5 post islet seeding and chips were maintained under flow for 48 hours and before fixing for immunocytochemistry or glucose stimulated insulin secretion (GSIS) on the chip.

All channels with human islets-on-chip showed at least ~7-fold increase in insulin secretion in response to an increment of glucose 20 mM underscoring the highly functional state of human islets cultured in this organ-chips MPS with flow compared to islets in conventional static culture that typically achieve ~1.5 fold increases in insulin secretion. Moreover, the importance of vascular endothelium on beta β-cell function and survival, islets seeded with iBMECs were more than twice as responsive to glucose as those without vascular endothelium, consistent with the higher percentage survival of β-cells detected in the presence of vascular (iBMECs) than non-vascular endothelium (HUVECS).

Moreover, in a study with i-Islets the Inventors observed a ~200 fold increase in insulin secretion when they were seeded with vascular endothelium. Taken together, these pilot studies (1) reveal that primary β-cells are more functional on the chip than in than in conventional culture, (2) that vascular endothelium on chip enhances primary β-cell function and survival, (3) that i-Islets-on-chip with vascular endothelium have markedly enhanced β-cell function, likely due to accelerated maturation, previously observed with neurons. The aforementioned results demonstrate that an islet-on-chip MPS that generates findings of immediate relevance in developing therapeutics for diabetes.

Example 6

Statistical Rigor and Experimental Design

At least n=10 independent experiments (n=12 chips/experiment) are performed for any given experimental design. In each experiment, the Inventors use key positive and negative controls for clearly interpreting the data and deriving conclusions. Using the statistical software (GraphPad Prism) and biostatistics core available at Cedars-Sinai the Inventors will perform appropriate power calculations using one-way ANOVA, two-way ANOVA, or two-tailed t-test analysis with ample biological/technical replicates as stated in the Research Design section of each aim.

Example 7

Functional iPSC Derived Islets on the Organ-Chip Device that Detects β-Cell Dysfunction in the Presence of a Known KCNJ11 Genetic Mutation as a Positive Control i-Islets in contact with vascular endothelium in the opposite chamber of a chip have increased maturity (proportion of β-cells that express allowed and not disallowed metabolic genes, mitochondrial density) and function (glucose mediated insulin secretion). In addition, it is suggested that exposure of vascular endothelium to islets on a chip confers specificity in vascular endothelium signaling that in turn benefits β-cell survival and functional development. Finally, i-Islets from patients with neonatal diabetes due to mutations in the KCNJ11 gene do not secrete insulin in a glucose responsive manner unless a sulfonylurea is present or following gene-correction of mutant KCNJ11 with functional KCNJ11 by CRISPR technology.

To evaluate the above, i-Islets are generated as described, and after confirmation of passing differentiation criteria will be seeded in the apical channel ($3 \times 10^3$ cells/µL; 28 µl resident, 8 µl dead volume) and iPSC-derived endothelial cells in the basal channel ($3 \times 10^4$ cells/µL; 5.5 µl resident, 10 µl dead volume) of plasma-activated fibronectin/laminin coated PET and PDMS-based organ-chip devices. One-day post-cell attachment, media flow is initiated and varied between a rate 150-100 µL/hour in the apical channel and 30 µL/hour in basal channel. The stability of the cells on the chips are assessed for up to 30 days. Per experiment 12 chips can be run on the Zoe; 6 chips per group are allocated for GSIS assay and 6 chips for IHC. Insulin secretion are evaluated 2 days and then again 5 days after iPSC were seeded on chips measuring glucose concentrations at 4 and 12 mM glucose. As a direct measure of glucose activation of β-cells mean cellular Ca' will also be evaluated in real time at 4 and 12 mM glucose by in-Chip calcium imaging using the fluo-4 and fura-2 AM indicator dye as published before. Chips assigned for cellular composition are fixed by perfusion of paraformaldehyde (PFA) and subsequently immunostained for insulin, glucagon, somatostatin, pancreatic polypeptide and ghrelin. Images of cells on chips are acquired by confocal imaging using Nikon A1R confocal and Molecular Devices high-content imaging Image Express Micro system and subsequently evaluated for cellular composition by MetaMorph and MetaExpress software for cell segmentation and morphometry analysis.

To evaluate the maturation of β-cells, islet cells are retrieved from the chips and β-cells retrieved by harvesting with TrypLE and subject to RT-PCR to profile for key allowed (GK versus disallowed HK, LDH genes) that characterize mature β-cells. Mitochondrial density is evaluated by mitotracker red.

Figure 3:
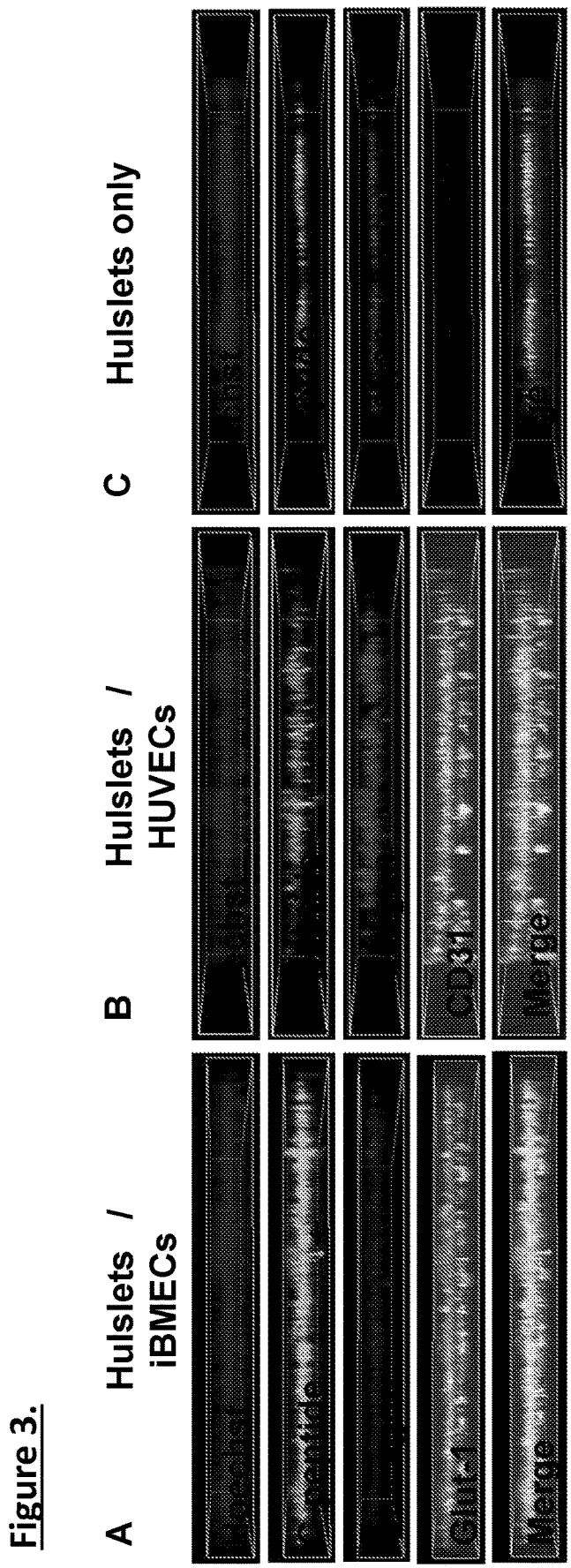
FIG. 3. Human cadaveric islets on chips: Panel showing cross-sectional view of islet staining on microphysiological (MPS) chips seeded with (A) Human Islets (HuIslets) in apical channel and iBMECs in basal channel, Red arrow indicates a C-peptide positive cell moving through the 7 μm pore to make contact with the iBMECs in the basal channel, (B) HuIslets in apical channel and HUVECs in the basal channel and (C) HuIslets alone in the apical channel. Nuclei are stained in blue with DAPI, C-peptide is shown in green and glucagon in red while the endothelial cells are shown in white. Islets showed higher C-peptide levels and negligible glucagon when co-seeded with iBMECs. However they showed higher levels of glucagon and lower levels of C-peptide when co-seeded with HUVECs. Islets by themselves did not seem to have enrichment of either of the populations specifically. Magnification 10×.
Figure 4:
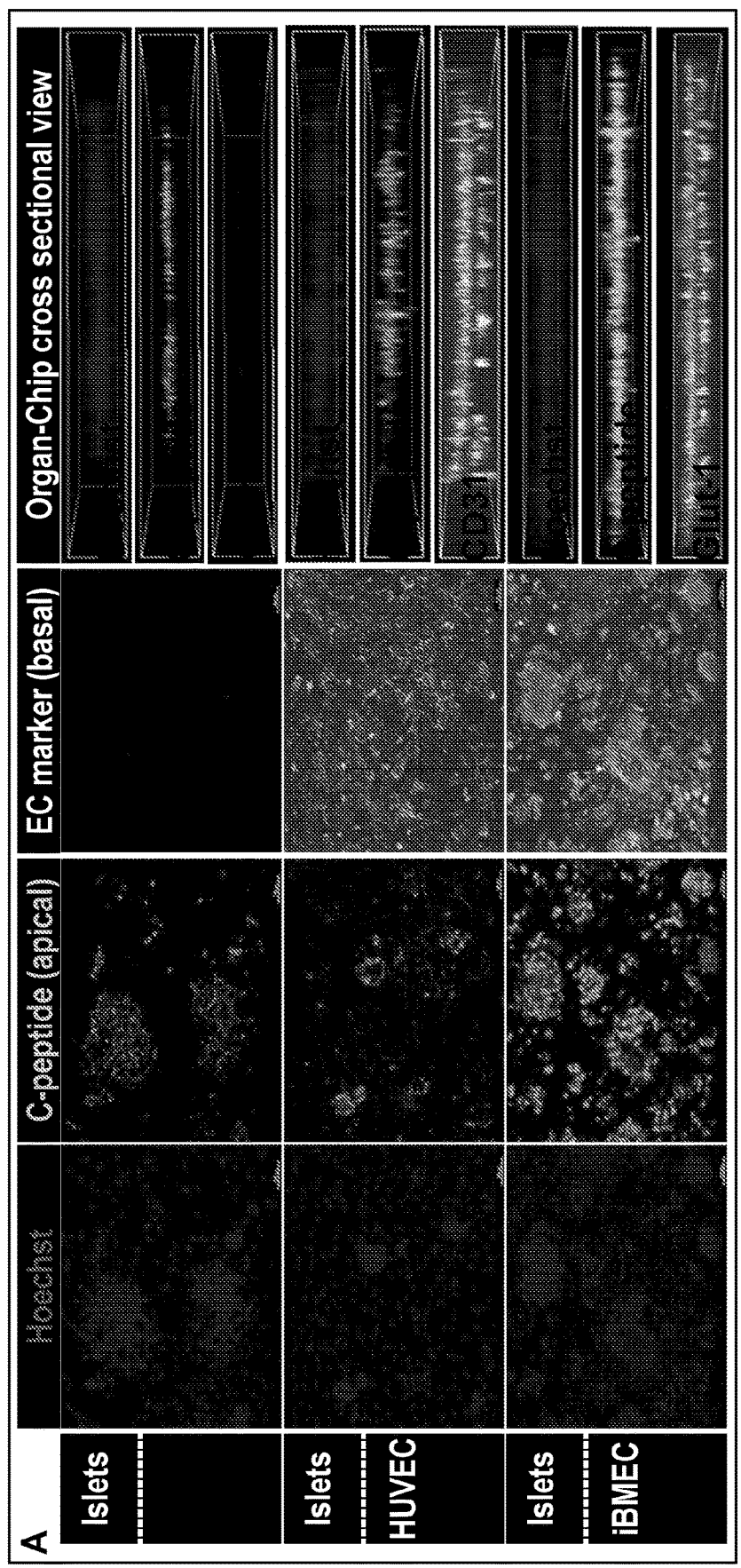
FIG. 4. Organ-chip: islets were cultured on the apical side of the chip with or without endothelial cells (HUVEC or iBMEC) on the basal side. Cells on chip were either (A) fixed and stained for insulin and endothelial cells marker (CD31 for HUVEC and Glut1 for iBMEC); left panels: projection view of membrane from top, right panels: cross sectional view of chip, or (B) subjected to glucose stimulated insulin secretion assay by passing through the chip medium containing 4 mM glucose, 20 mM glucose, and then 20 mM KCl to reveal insulin content. Co-culture with of islets with iBMEC resulted in an increase in C-peptide content and glucose stimulated insulin secretion.
Figure 4:
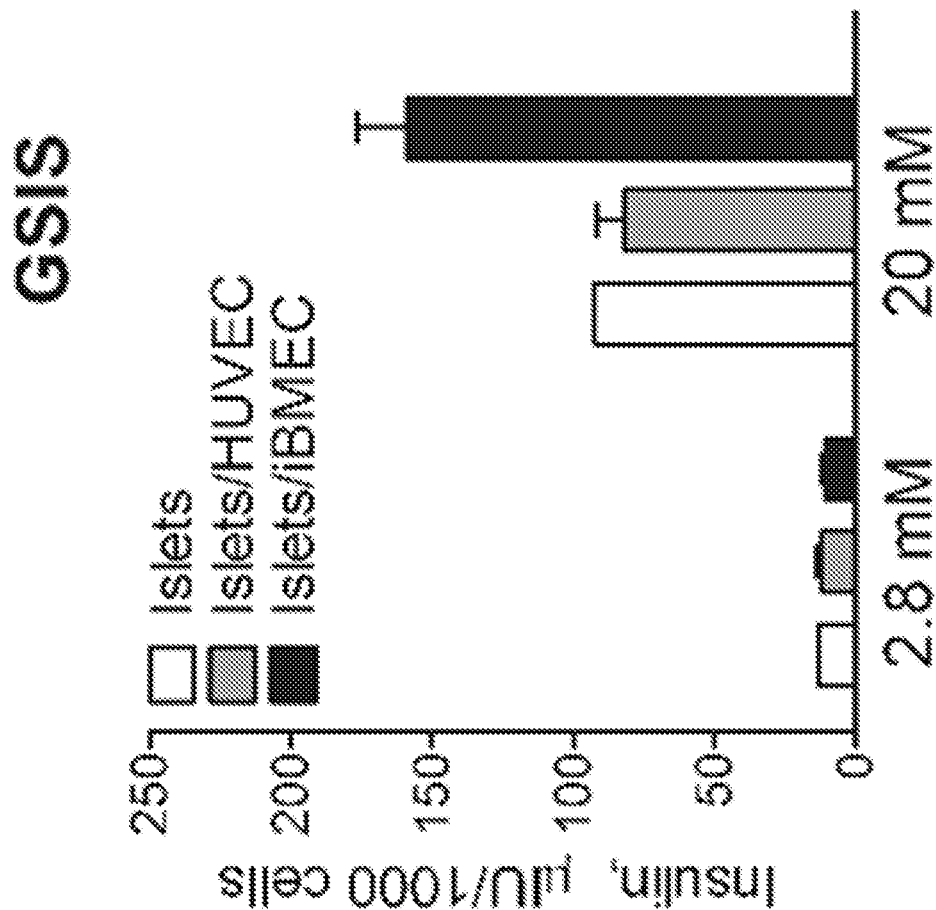
Figure 5:
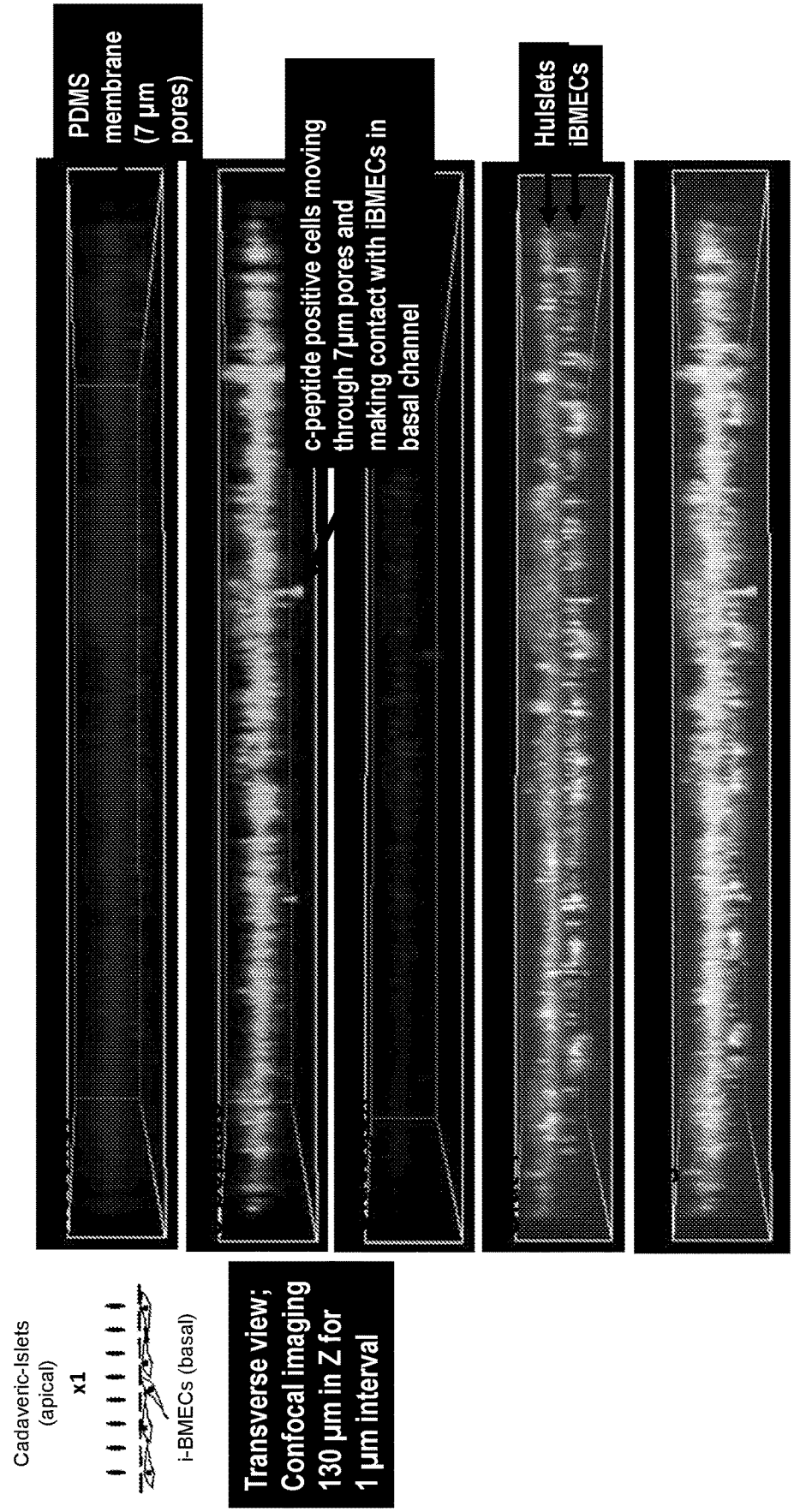
FIG. 5. Cadaveric islets in apical channel and iBMECs in basal channel. Transverse view confocal imaging 130 μm in Z for 1 μm interval. Hoescht, c-peptide, glucagon, glut-1 and merge stain.
Figure 6:
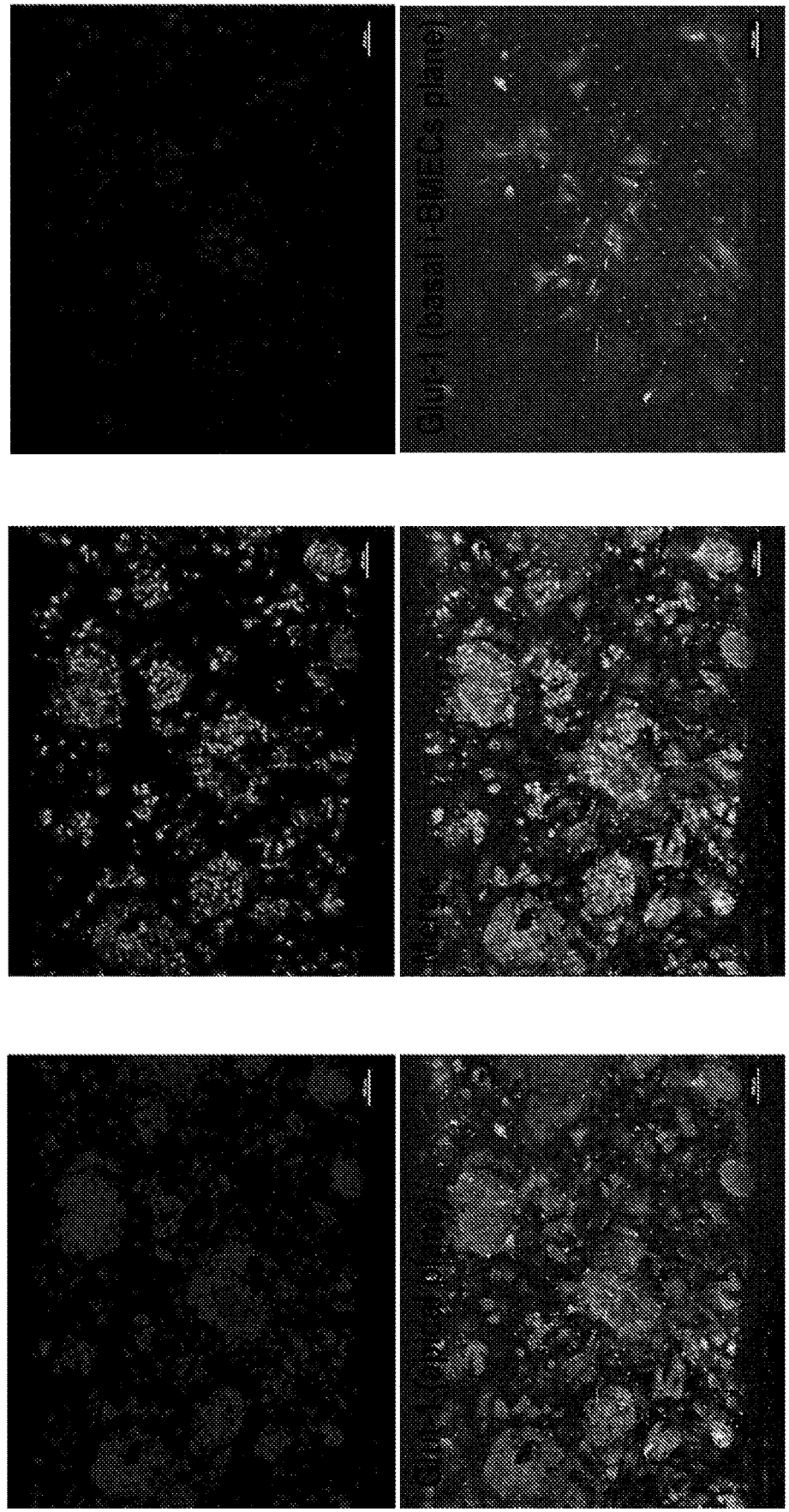
FIG. 6. Cadaveric islets in apical channel and iBMECs in basal channel. Top view. Hoescht, c-peptide, glucagon, glut-1 (apical plane), merge, and glut-1 (basal) stain. Best focus projection from top.
Figure 7:
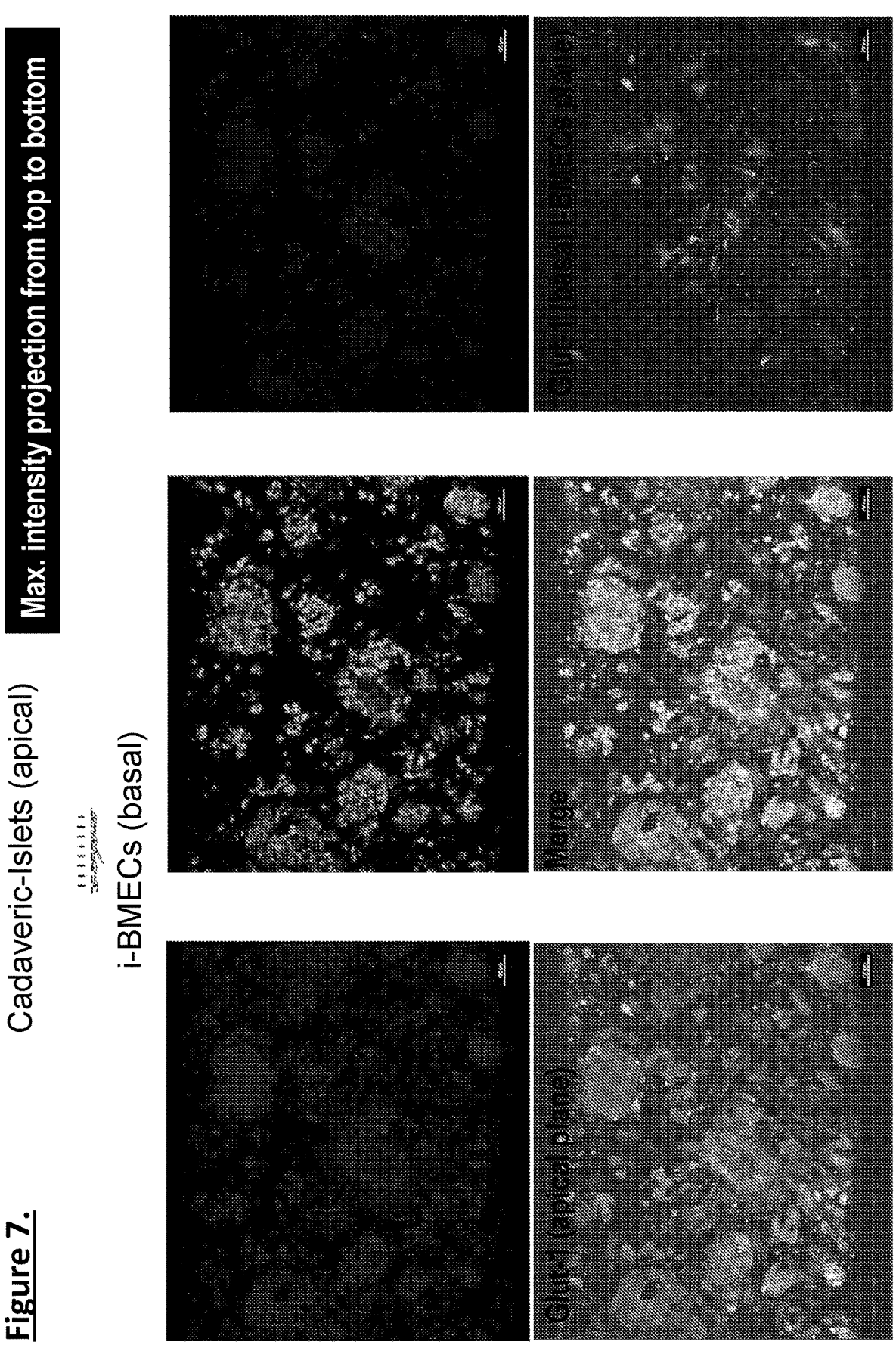
FIG. 7. Cadaveric islets in apical channel and iBMECs in basal channel. Maximum intensity projection. Hoescht, c-peptide, glucagon, glut-1 (apical plane) merge, and glut-1 (basal) stain. Best focus projection from top.
Figure 9:
FIG. 9. Cadaveric islets in apical channel and HUVECs in basal channel. As shown, fewer c-peptide positive cells in HUVECs vs. iBMECs co-culture. Transverse view confocal imaging 130 µm in Z for 1 µm interval. Hoescht, c-peptide, glucagon, CD31 and merge stain.
Figure 11:
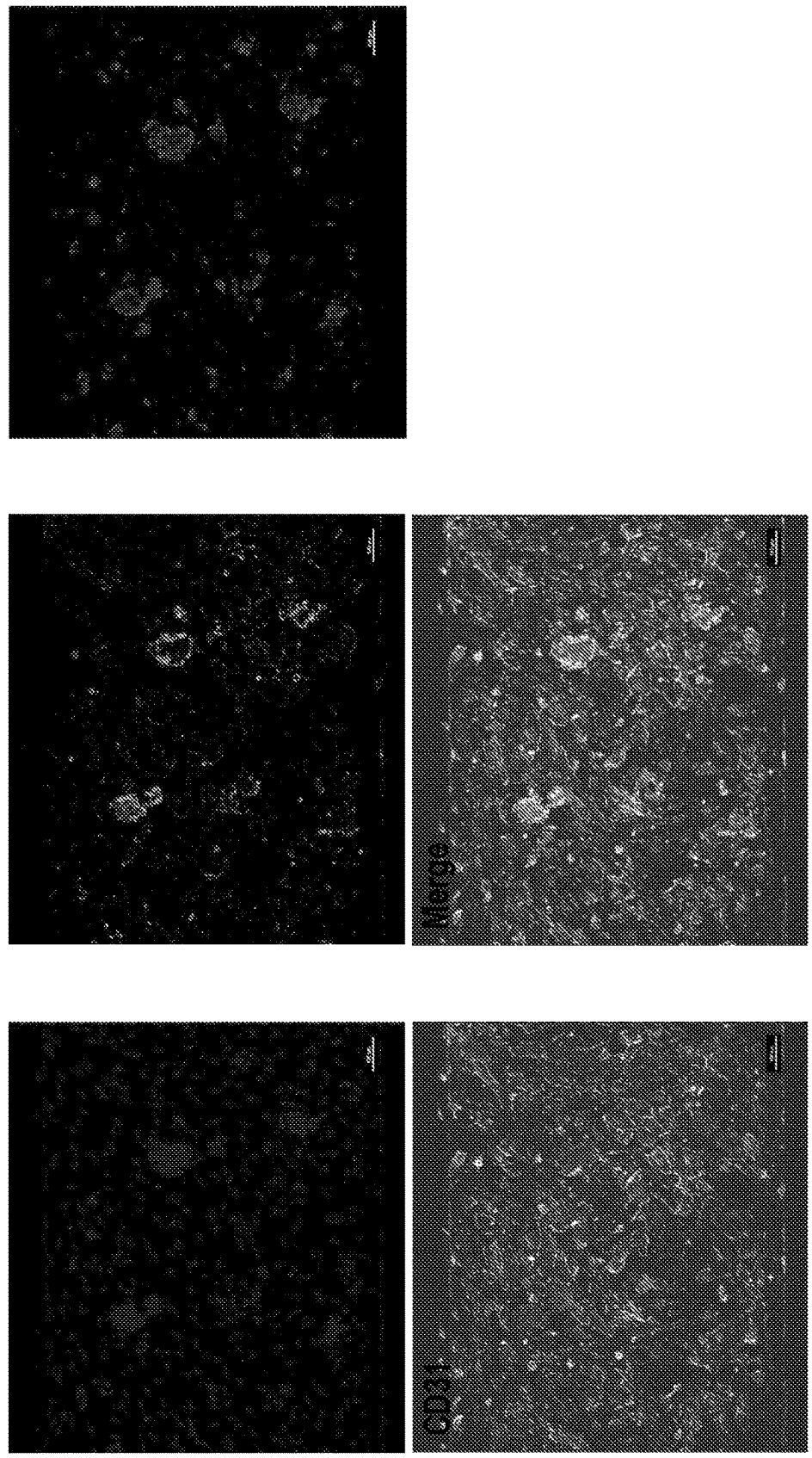
FIG. 11. Cadaveric islets in apical channel and HUVECs in basal channel. Maximum intensity projection. Hoescht, c-peptide, glucagon, CD31 and merge stain. Best focus projection from top.
Figure 12:
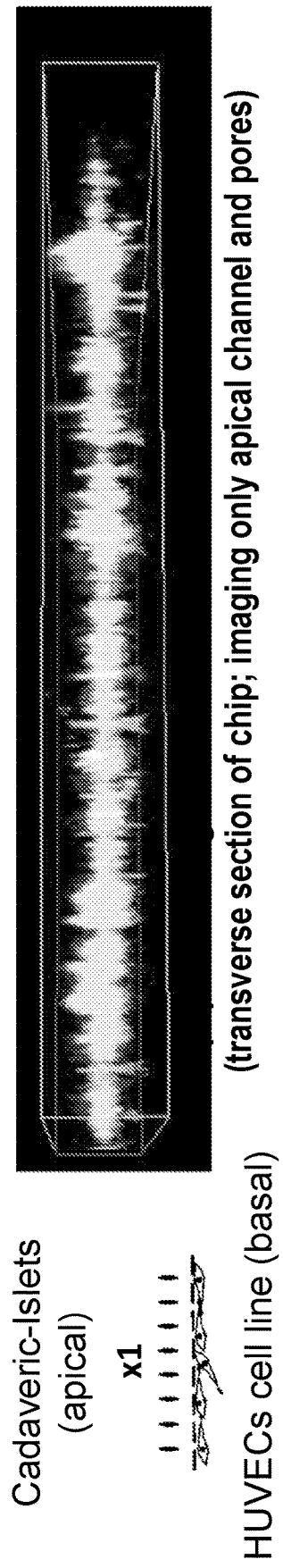
FIG. 12. Cadaveric islets in apical channel and HUVECs in basal channel. Multiple views including transverse section, 3D projection view, best focus projection via, each including Hoescht, c-peptide, glucagon, CD31 stain. Best focus projection from top.
Figure 13:
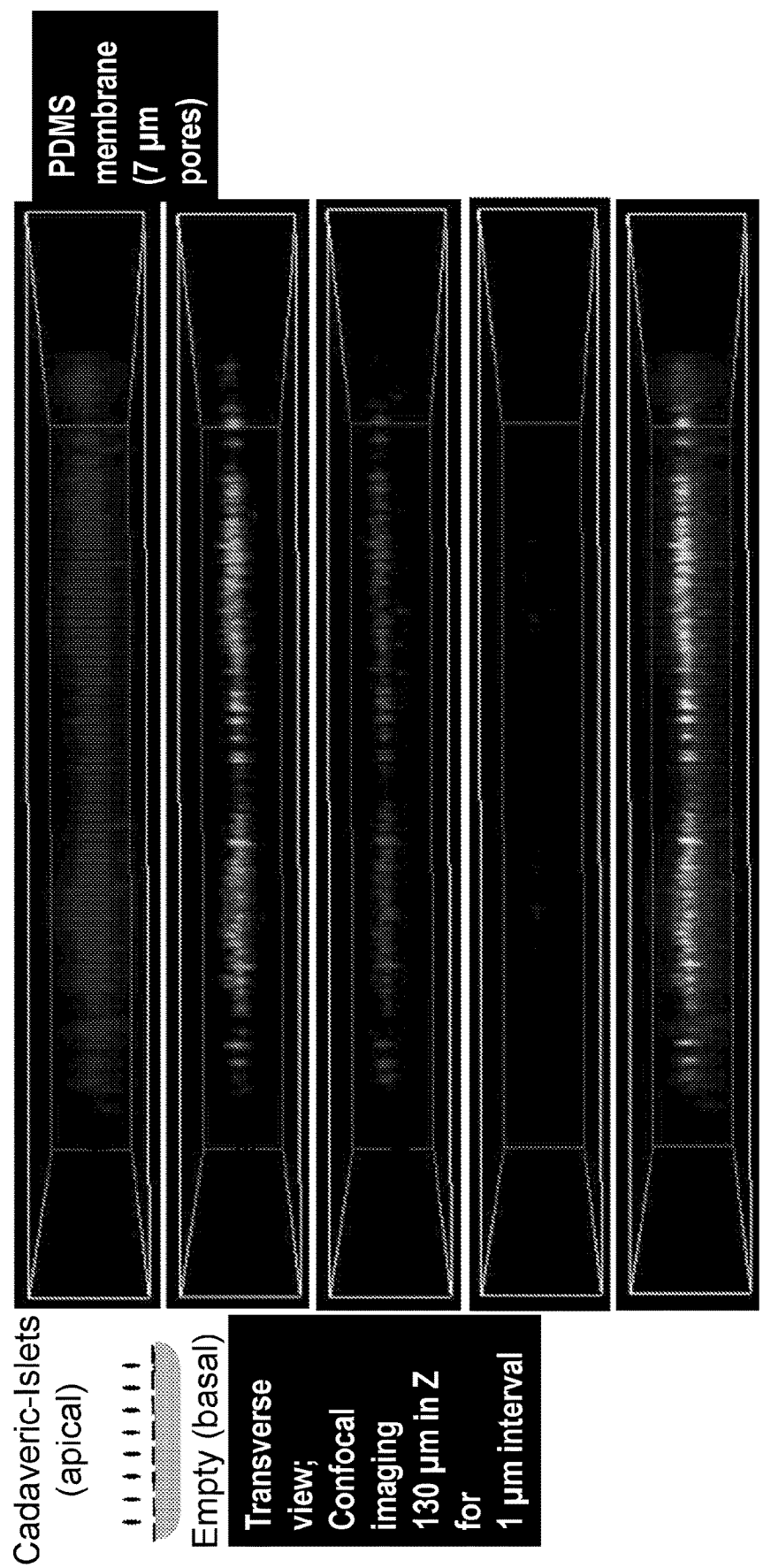
FIG. 13. Cadaveric islets in apical channel. As shown, fewer c-peptide positive cells in HUVECs vs. iBMECs co-culture. Transverse view confocal imaging 130 µm in Z for 1 µm interval. Hoescht, c-peptide, glucagon, CD31 and merge stain.
Figure 14:
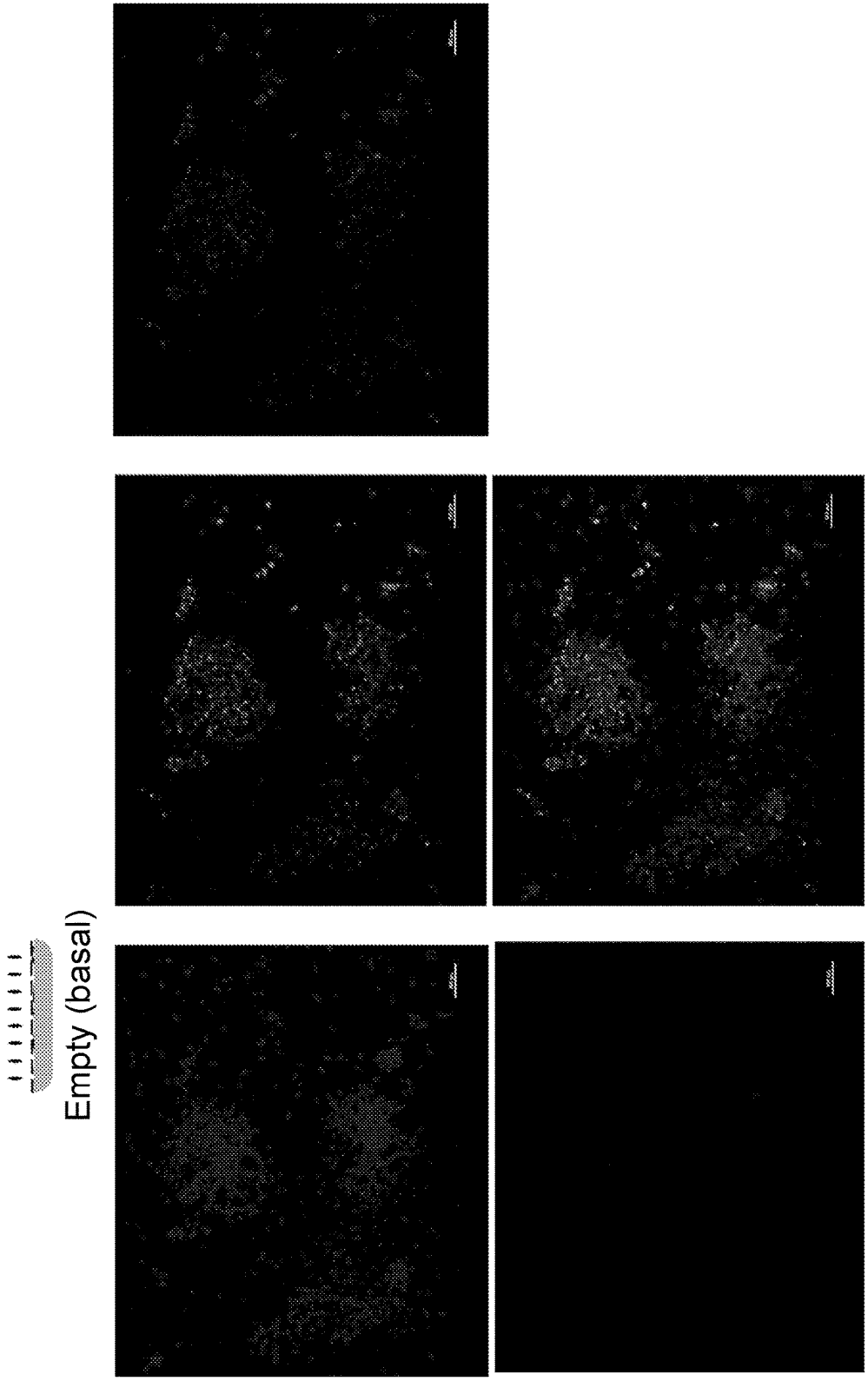
FIG. 14. Cadaveric islets in apical channel. Top view. Hoescht, c-peptide, glucagon, CD31 and merge stain. Best focus projection from top.
Figure 15:
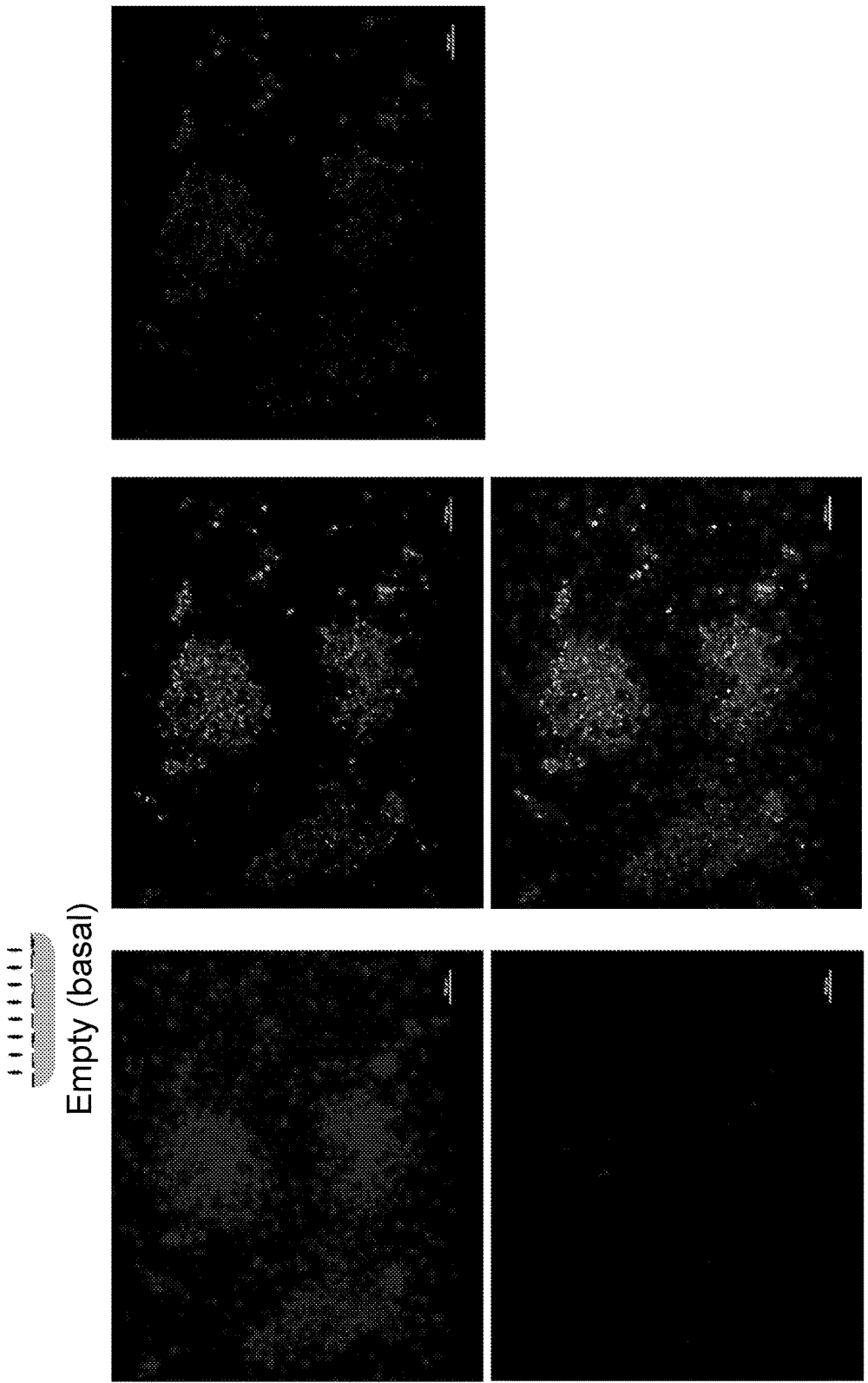
FIG. 15. Cadaveric islets in apical channel. Maximum intensity projection. Hoescht, c-peptide, glucagon, CD31 and merge stain. Best focus projection from top.
Figure 16:
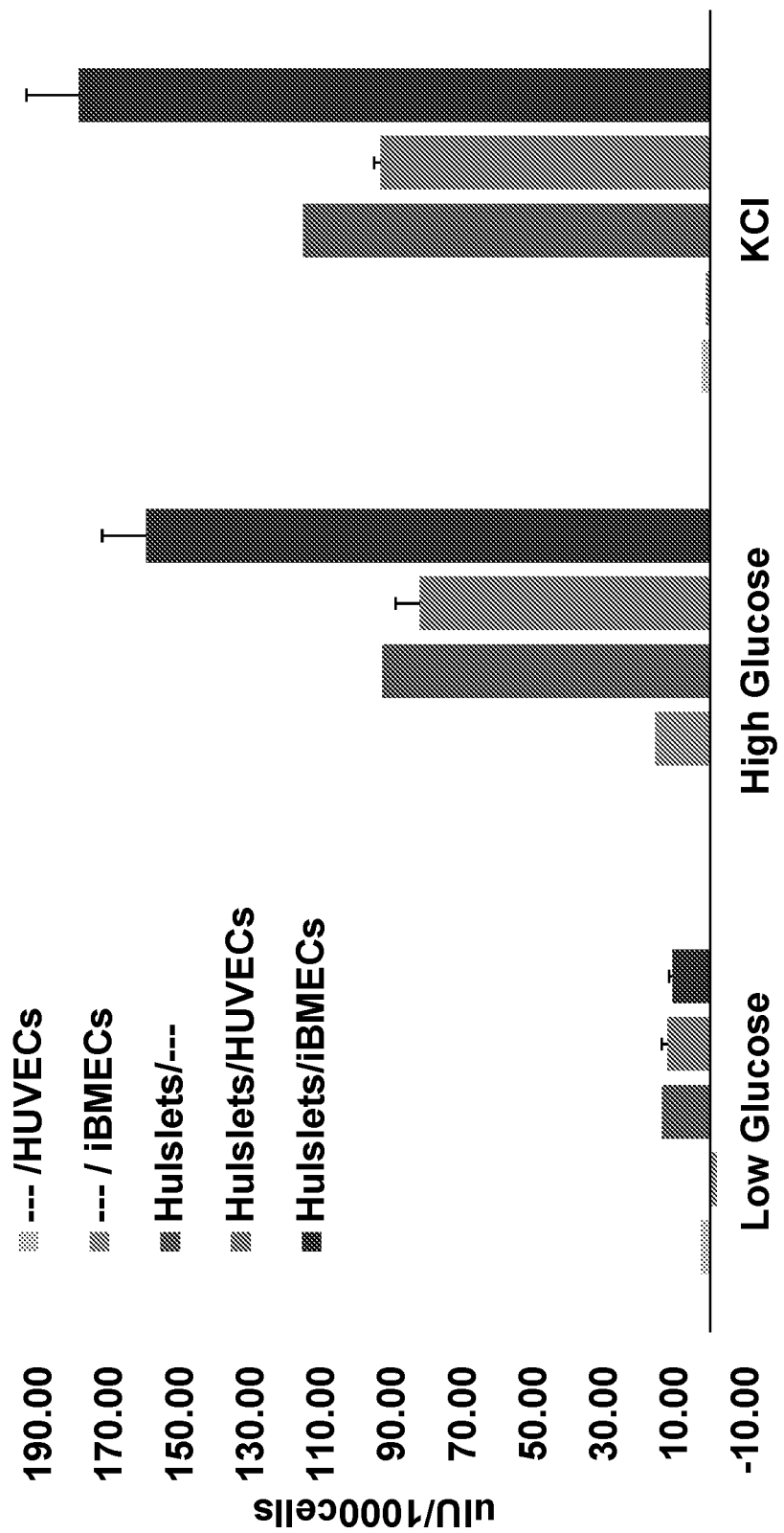
FIG. 16. Glucose-stimulated insulin secretion (GSIS) assays. Human insulin ELISA showing measured secreted insulin levels in the various chips as indicated in the graph. Insulin secretion was normalized. Control samples of HUVECs and iBMECs in basal channel, human islets alone in top channel, co-culture of human islets HUVECs and iBMECs. In agreement with the ICC, Hulslets co-seeded with iBMECs secreted higher levels of insulin compared to Hulslets co-seeded with HUVECs or even the Hulslet only chips. Either of the endothelial cells did not secrete detectable levels of insulin.
Figure 17:
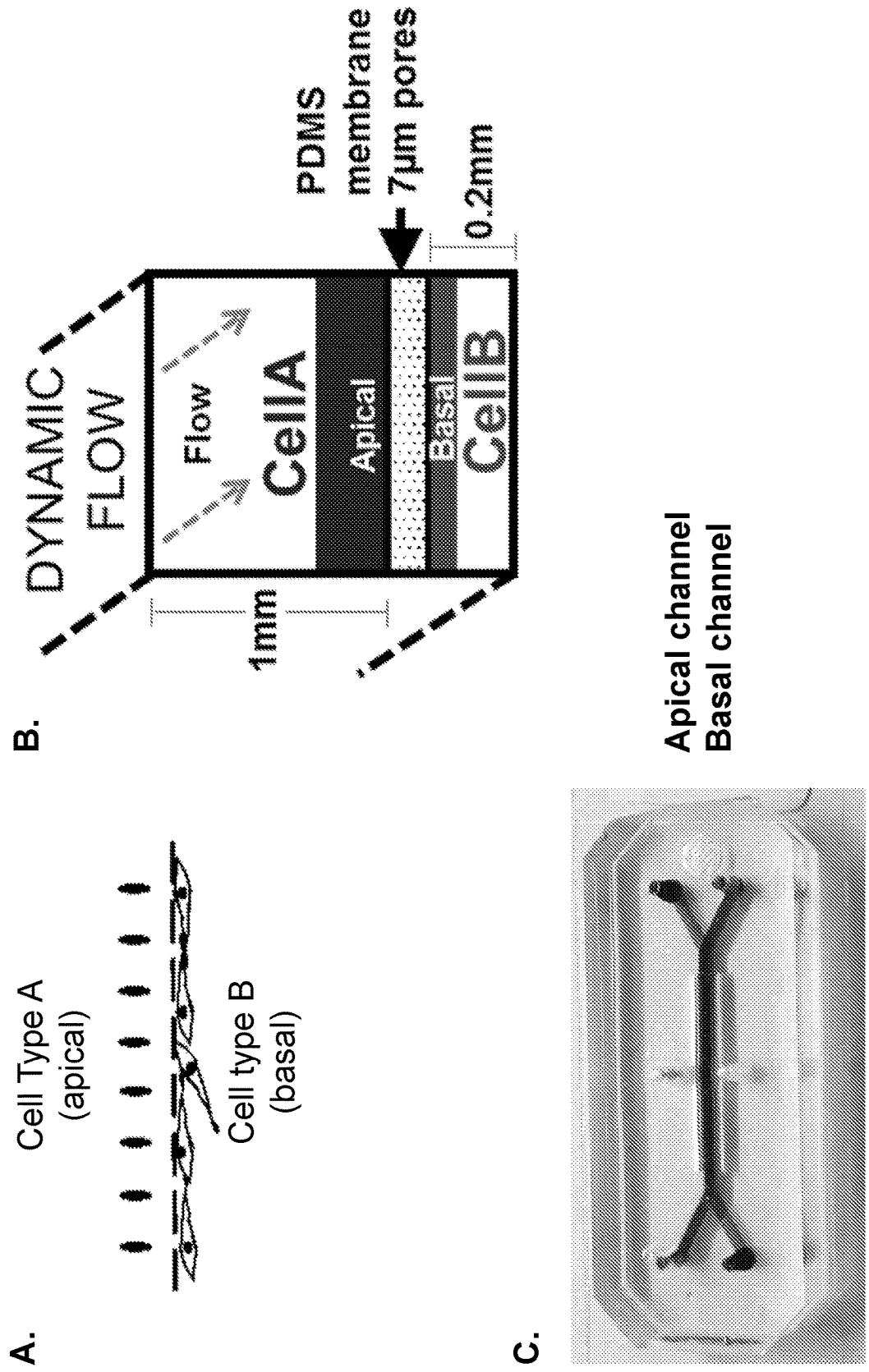
FIG. 17. The organ-chip System: (A)-(C) Chip Architecture and principle (A) Cross section of chip showing seeding of different cell types in the two channels, (B) Chip dimensions of each channel, (C) Image of the MPS chip highlighting the apical channel (red) and the basal channel (purple). The chips include two microfluidics channels—an apical and a basal channel. The apical channel is 1 mm tall and 1 mm wide, while the basal channel is 200 µm tall and 1 mm wide. These two channels are separated by a poly (dimethylsiloxane) (PDMS) membrane which is 10 µm thick, patterned with 7 µm pores. The apical channel, the membrane and the basal channel are plasma bonded to form a complete chip. Each channel can be populated with different cell types and culture medium can be flowed through both channels at desired flow rates to look for cellular interactions between the two cell types. The apical channel can hold 28.041 µL of medium while the basal channel can hold 5.584 µL of medium.
Figure 19:
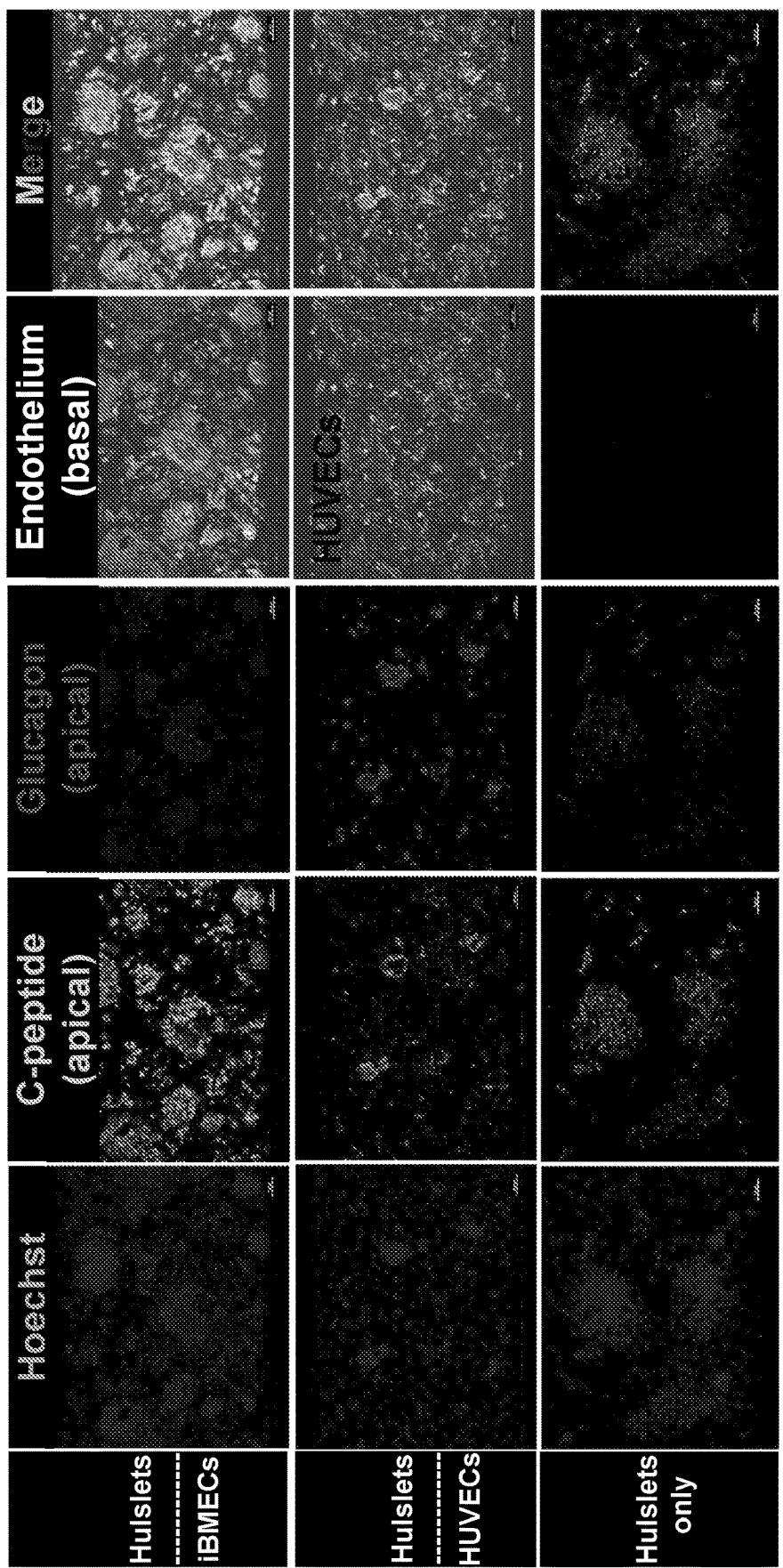
FIG. 19. Representative staining results of Hoescht, c-peptide, glucagon, endothelium and merge stain of human islets/iBMECs, human islets/HUVECs, and human islets only.
Figure 20:
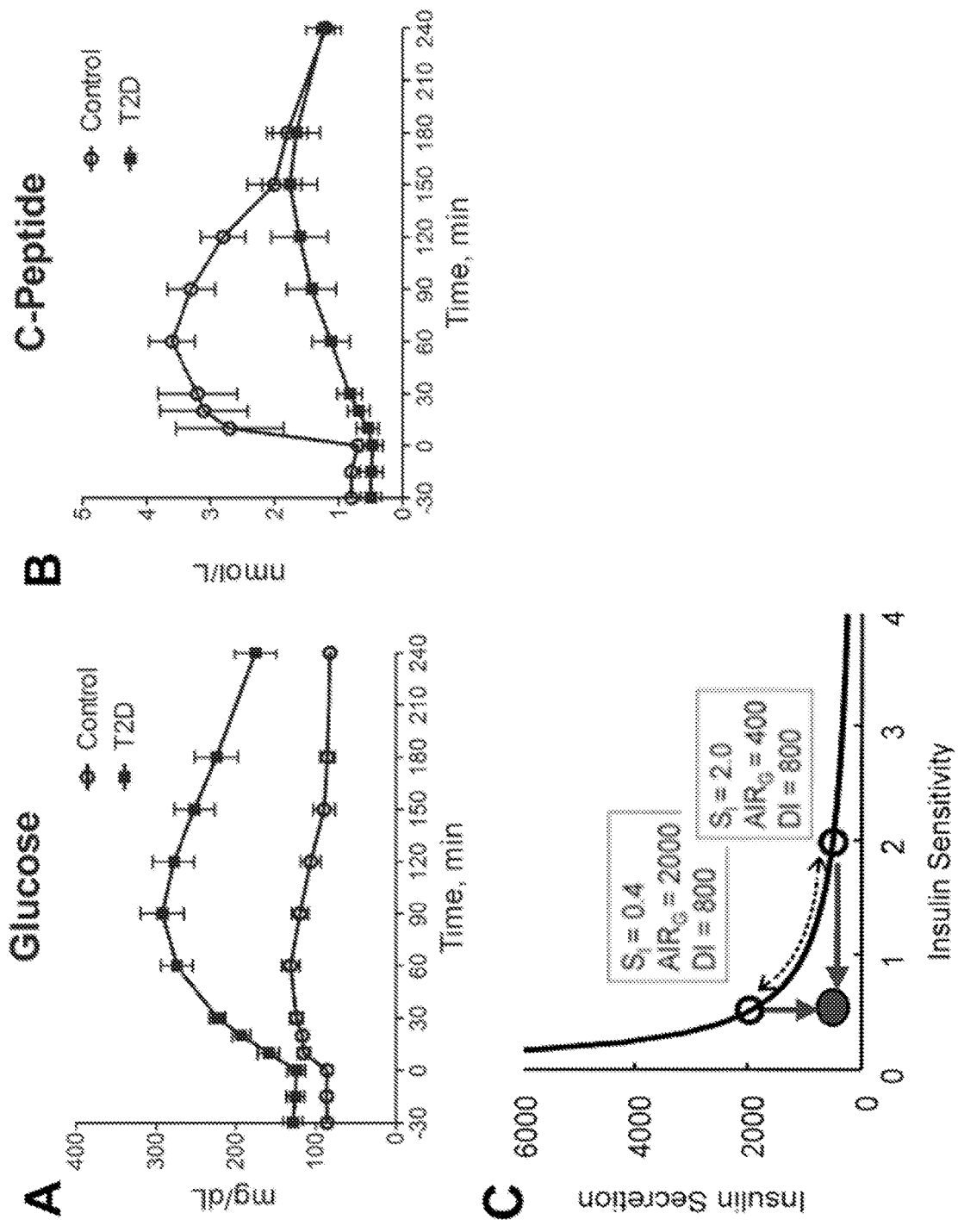
FIG. 20. Plasma glucose (A) and C-peptide (reflects insulin secretion, (B) concentrations in non-diabetic (Control) and T2D subjects before and after mixed meal reveals defect in insulin secretion and sensitivity. (C) Solid line shows relationship between insulin secretion and insulin sensitivity in non-diabetic controls by mixed meal. Red arrows point to individual T2D patient with relative contribution of deficient insulin secretion (vertical arrow) and insulin sensitivity (horizontal arrow) to diabetes.
Figure 21:
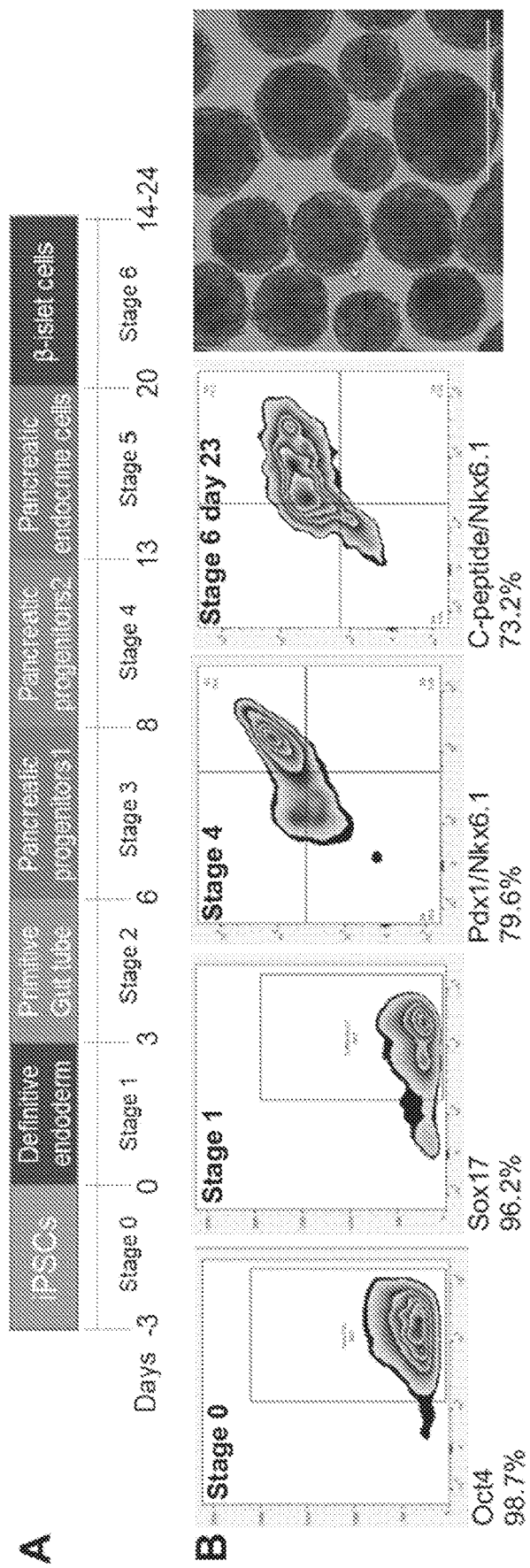
FIG. 21. (A) Schematic of differentiation iPSCs into pancreatic beta cells. (B) FACS analysis performed at indicated stages of differentiation and an image of iPSC-derived islets at the end stage of differentiation. (C) Image of a cross section of iPSC-derived islet immnunostained for insulin. (D) Glucose stimulated insulin secretion (GSIS): Stage 6 iPSC-derived islets were periperfused with 4 mM glucose followed by 20 mM glucose and samples were collected every minute; insulin was measured in perfusate by ELISA.
Figure 22:
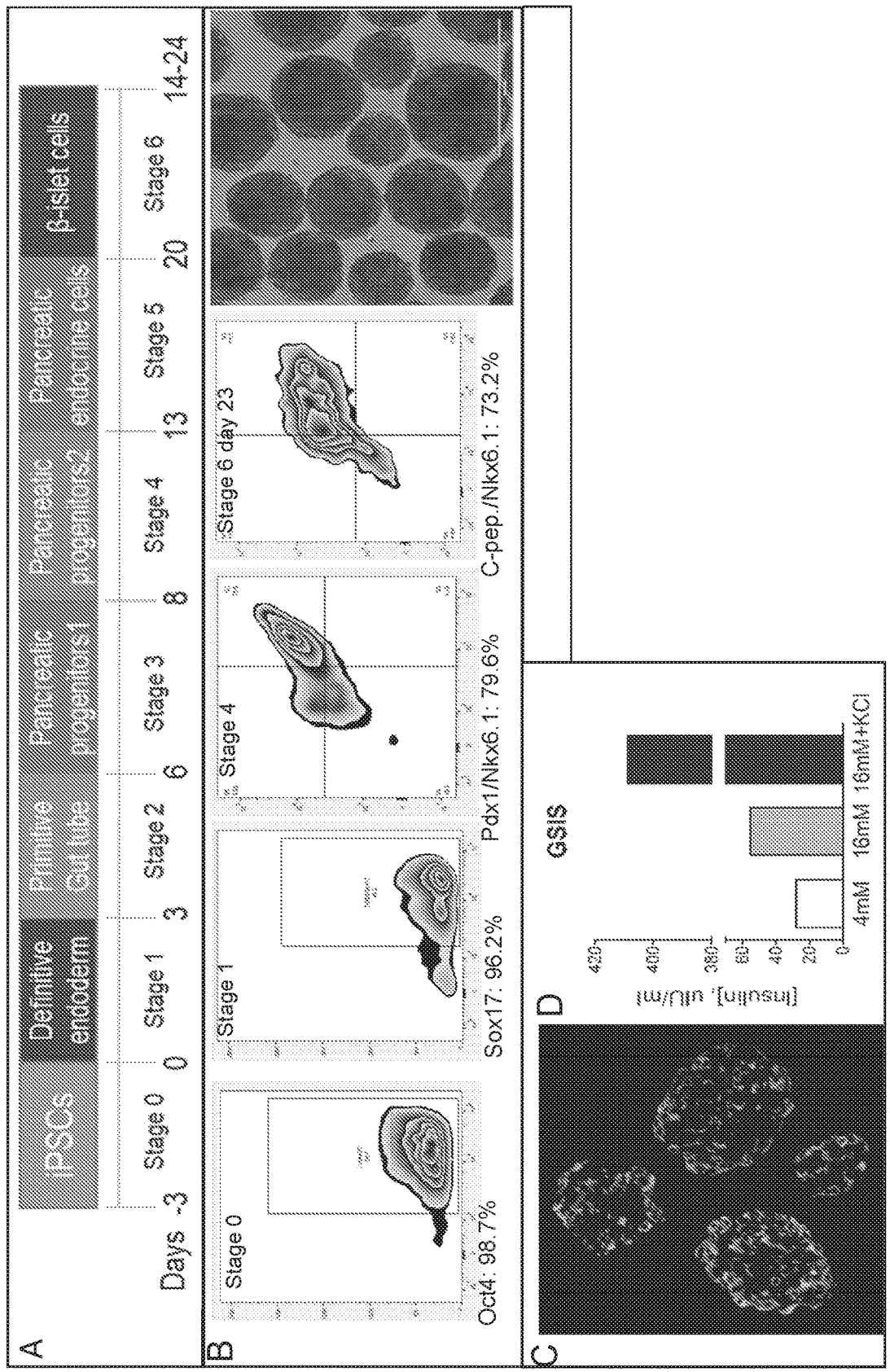
FIG. 22. (A) Schematic of differentiation iPSCs into pancreatic beta cells. (B) FACS analysis performed at indicated stages of differentiation and an image of iPSC-derived islets at the end stage of differentiation. (C) Image of a cross section of iPSC-derived islet immnunostained for insulin. (D) Glucose stimulated insulin secretion (GSIS): Stage 6 iPSC-derived islets were exposed 4 mM glucose, 20 mM glucose, followed by 20 mM KCl to reveal insulin content. Insulin was measured in supernatant by ELISA.
Figure 23:
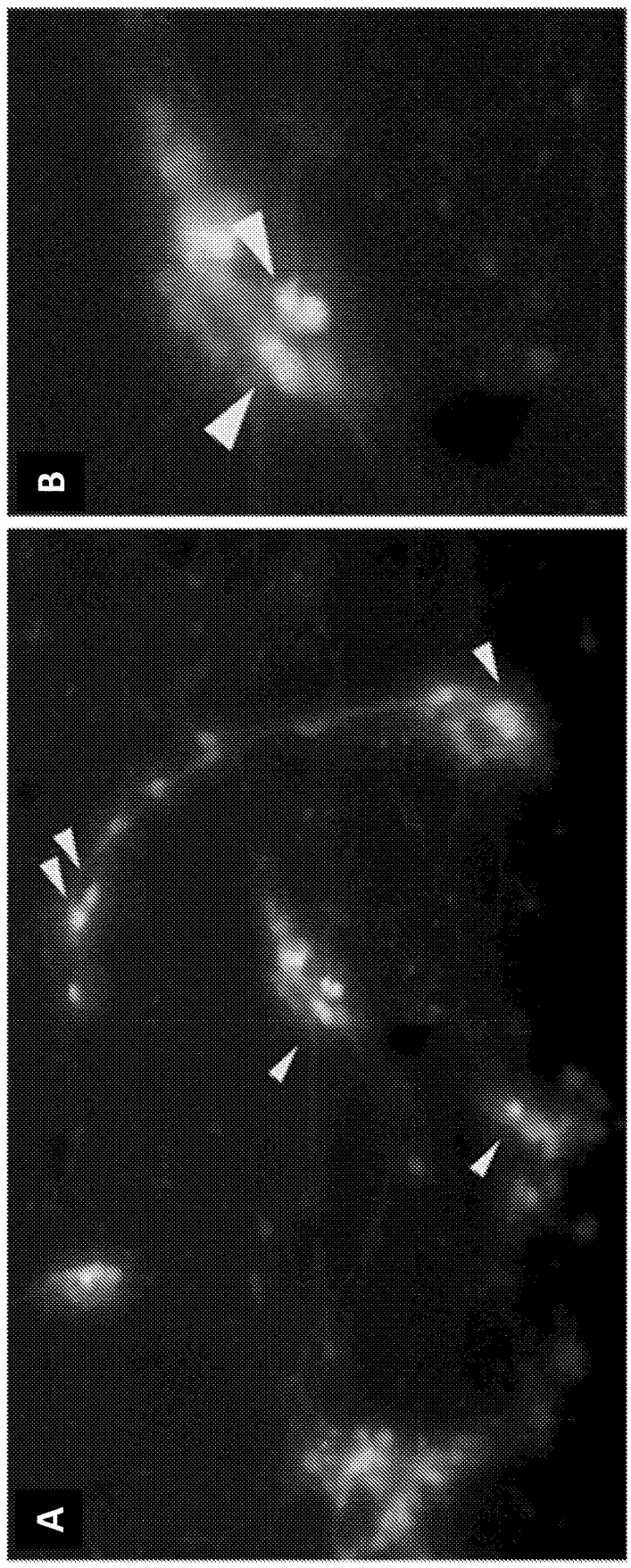
FIG. 23. Feasibility of in-Chip Calcium Imaging: (A)-(B) iPSC-derived motor neurons seeded on top channel of Organs-Chips. (C)-(J) Live time-lapse imaging of live i-Motor neurons showing spontaneous Ca' transients upon loading with calcium indicator fluo-4. Images are pseudo-colored to show increase or decrease in intracellular $Ca^{2+}$ concentration as seen by traces plotted in (K).
Figure 23:
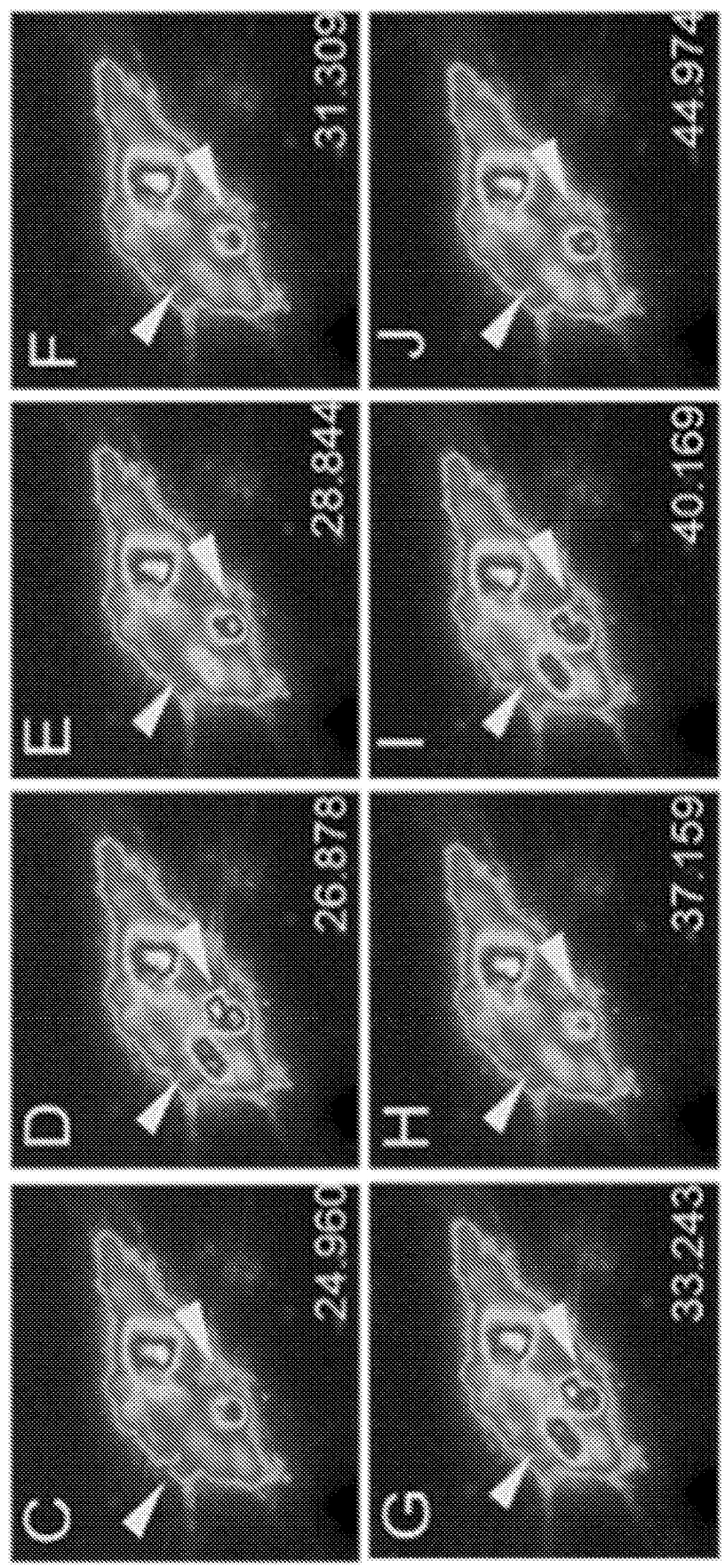
Figure 23:
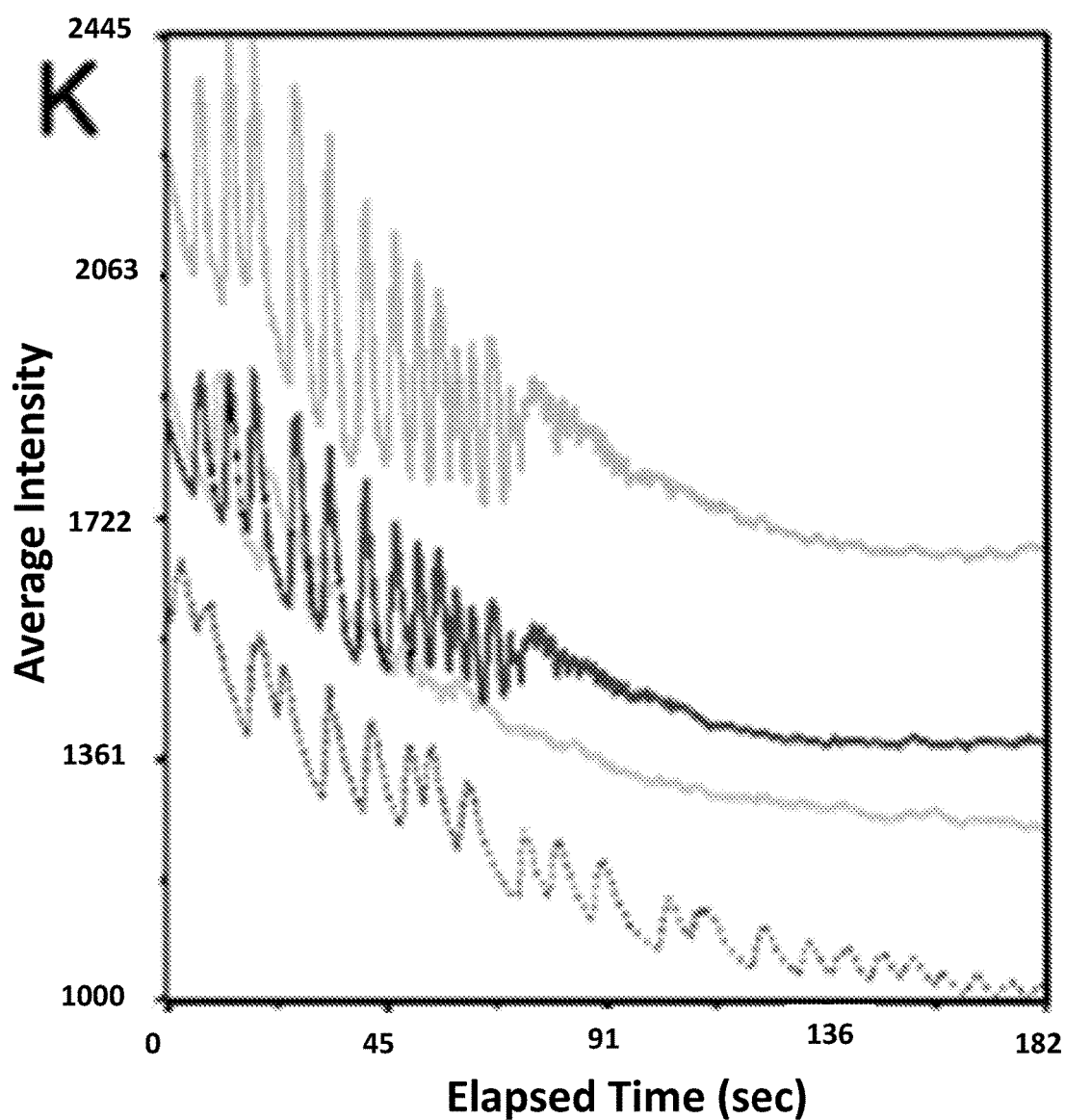
Figure 24:
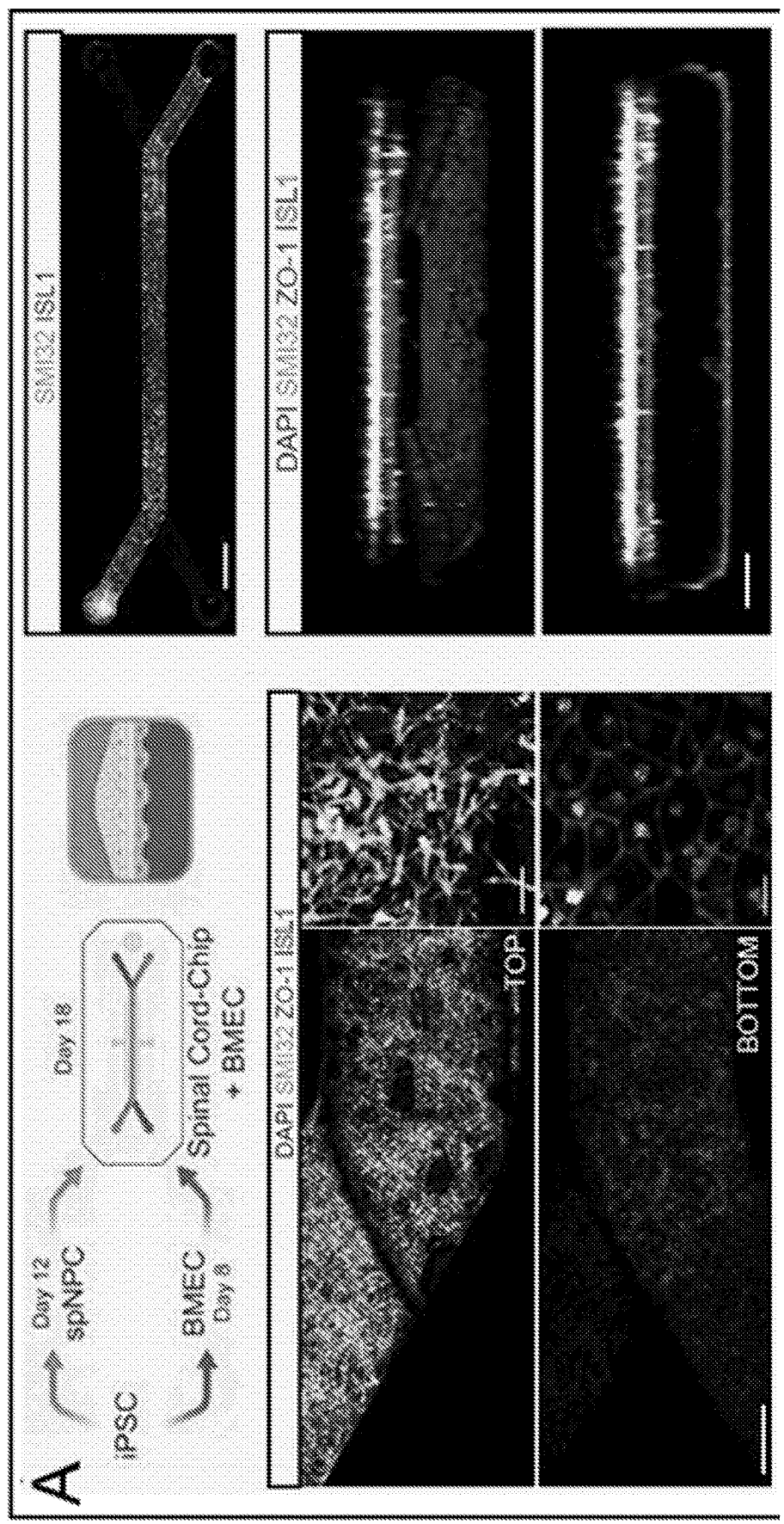
FIG. 24. iPSC-motor neurons co-cultured with vascular endothelium on organ-chips show signatures of vascular interaction and neuronal maturation (Stem Cell Reports. in press).
Figure 24:
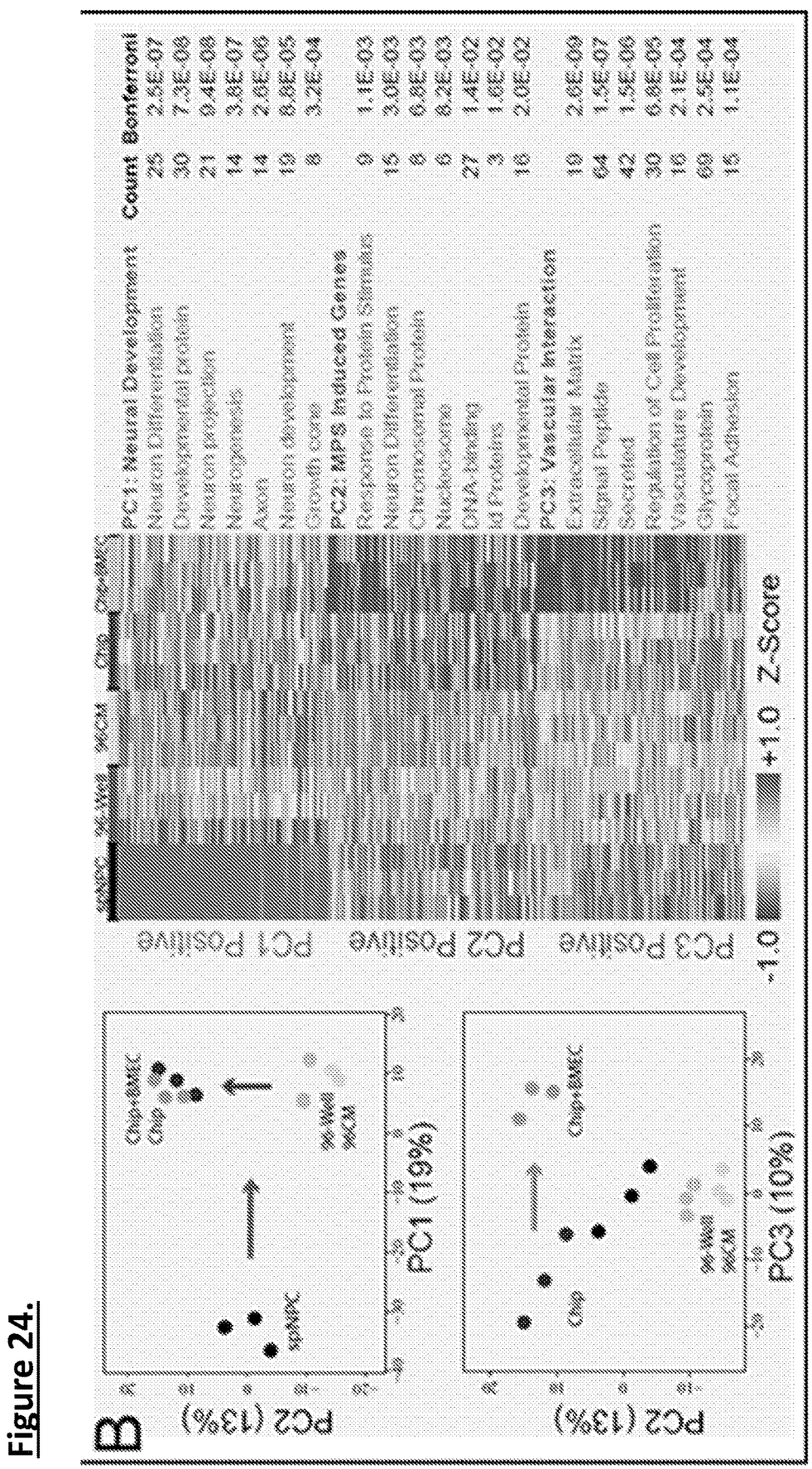

Similar analysis is obtained using primary human islets from brain dead organ donors, after partial trypsin digestion are seeded onto the apical chamber of organ-chips as shown in FIG. 3. The i-Islets from the KCNJ11 mutant iPSCs are subject to static incubation low (4 mM) and high (12 mM) glucose in the presence and absence of sulfonylurea (the same as each patient is taking for therapy). The islets will then also be seeded into the apical chamber with corresponding vascular endothelium in the basal chamber. Organ-chip glucose stimulation and real time Ca' imaging is carried out as above in the presence and absence of the relevant therapeutic sulfonylurea. iPSCs from two of the KCNJ11 clones that perform best in differentiation are subject to repair of the KCNJ11 by CRISPR and then further differentiation and evaluation of GSIS secretion by static incubation and on-chip carried out as above.

The Inventors have reporter iPSC lines labeled with nuclear-GFP (83i-nGFP) and cytoplasmic-RFP (83i-cRFO) under β-actin promoter from single isogenic line[11]. The Inventors will perform single-cell RNA-sequencing by harvesting the i-Islets and i-BMECs from both channels of the chips, sorting for either GFP$^+$ i-islets and RFP$^+$ iBMECs, and profiling for vascular interactions and maturation. (10× genomics), and perform principal component and DAVID. By this process candidate signaling pathways are sought that drive β-cell development to full maturation and function. Such signals would represent important targets for use in final stages of stem cell derived islet differentiation. Moreover, since a current hypothesis for development of T2D is dedifferentiation of β-cells, targeting signaling pathways that enhance β-cell maturation would represent a novel potential therapeutic pathway for T2D.

Example 8

Primary Human and iPSC Derived Skeletal Muscle and iPSC Motor Neurons on Chips

The Inventors have previously developed neuromuscular junctions (NMJs) and innervated skeletal muscle on organ-chips. The Inventors have developed methods for differentiation of and skeletal muscle and motor neurons from iPSCs and formation of NMJs in a dish and on organ-chips.

Briefly, the Inventors procured primary human skeletal muscle from a commercial vendor (Cell Applications), where the Inventors optimized and seeding density and attachment conditions on different organ-chips polymer biomaterials, including chemical cross-linking agents and collagen/fibronectin extracellular matrix, as essential for successful long-term (30 day) attachment of primary muscle on organ-chips. The primary skeletal muscle did not demonstrate any twitching (contraction) without innervation from the neurons. When muscle was co-cultured with iPSC-derived motor neurons (iMNs) on organ-chips, the Inventors observed contraction of the muscle that was dependent on the co-culture of the iMNs and the media. Immunohistology confirmed the presence of functional NMJs on the organ-chips. Thus, these experiments suggest innervated skeletal muscle if functional and likely to be crucial in mimicking human skeletal muscle physiology on organ-chips to assess the effects of insulin-mediated glucose uptake on the muscle in diabetes and health.

For generation of iPSC-derived skeletal muscle (i-SkM), undifferentiated hiPSC lines are maintained and expanded feeder-free on matrigel-coated plates in serum-free E8 medium. I-SkM differentiation experiments are performed in a 5% $O_2$/5% $CO_2$ incubator, by using commercially available skeletal muscle differentiation medium. Briefly, cells are plated at 2,500 cells per cm$^2$ onto Matrigel or collagen I-coated plates and maintained for 10 days in skeletal muscle induction medium containing 5% horse serum, 3 µM CHIR99021, 2 µM Alk5 Inhibitor, 10 ng/ml hr-EGF, 10 mg/ml insulin 0.4 mg/ml dexamethasone, and 200 µM ascorbic acid. At day 10, cells are dissociated with and plated on to Matrigel and collagen-I coated-organ-chips, and maintained for 8 days in skeletal myoblast medium containing 5% horse serum, 10 mg/ml insulin, 10 ng/ml hr-EGF, 20 ng/ml hr-HGF, 10 ng/ml hr-PDGF, 20 ng/ml hr-bFGF, 20 µg/ml oncostatin, 10 ng/ml IGF-1, 2 µM SB431542, and 200 µM ascorbic acid. Further maturation in the presence after 18 days of differentiation, myotube formation is promoted with the addition of 10 mg/ml insulin, 20 mg/ml oncostatin, 50 nM necrosulfonamide, and 200 µM ascorbic acid. Cells are then maintained for 7 days in myotube medium. The iPSC-derived motor neurons (iMNs) are differentiated as the Inventors have previously described.

Skeletal muscle is highly vascularized to meet the high energetic demand for muscle activity. Vascular inflow to skeletal muscles is provided by primary arteries, of which the feed arteries account for as much as 30-50% of the total resistance to blood flow through skeletal muscle. Capillary networks surrounding skeletal muscle play not only supply oxygen and nutrients, but also regulate myogenesis and skeletal muscle repair. Insulin resistance in type 2 diabetes is accompanied by defects in the vasculature of skeletal muscle, which ultimately reduce the ability of insulin and nutrients to reach myocytes[19]. Insulin transport from the bloodstream to its target skeletal muscle requires transport across a vascular endothelial-skeletal muscle barrier. Given the Inventors' observations from the neurovascular organ-chips, the Inventors expect that the presence of endothelial cells to enhance function of iSkM chip and recapitulate more human-specific skeletal muscle pathophysiology on the iSkM organ-chips. In this case the endothelial cells are seeded in the bottom channel and the (iMNs-iSkMs) innervated iSkM are co-cultured on the top channel.

Example 9

Functional iPSC-Derived Skeletal Muscle (i-SkM) on the Organ-Chip Devices

It is suggested that i-SkM in contact with vascular endothelium in an organ-chip has increased metabolic development (mitochondrial density, insulin mediated glucose uptake). Additionally, it is suggested that iInnervation of i-SkM with iPSC-motor neurons increases insulin mediated glucose uptake. Finally, i-SkM from patients with inactivating insulin receptor (IR) mutations have insulin resistance reversed by CRISPR correction of the IR mutation.

The innervation of i-SkM and iMNs can be measured by formation of functional NMJs and immunostaining with α-bungarotoxin, βiii tubulin for neurons, synaptic vesicle 2 (SV2) and MI-IC (muscle). The formation of mature skeletal muscle can be measured formation of myotubes on the chip as shown in image below for example. The fusion index (degree of poly-nucleated myofibers) of the myotubes is determined. Metabolic maturation is evaluated by quantifying key regulatory proteins and enzymes including glucose 4 transporter proteins, hexokinase-2 and mitochondrial density by mitotracker red.

The myofiber contraction frequency can also be measured upon innervation with iMNs with and without endothelial cell co-culture by counting the contractions/minute of the myotubes using phase time-lapse imaging.

Finally, muscle do better on micro-patterned chips where myotubes can organize linearly using channels etched out on the polymer membrane and this would be part of development of the additionally chip designs.

Insulin action in i-SkM and primary skeletal muscle-Chips are measured by insulin mediated glucose uptake. This is evaluated directly by glucose concentration difference across the chip x flow (5 mM perfusate glucose) at basal insulin (10 μU/ml) followed by stimulated insulin (100 μU/ml). For real time insulin mediated glucose transport and phosphorylation the Inventors will also quantify the accumulation of a fluorescent tracer of 2-deoxy-D-glucose, 2-[N-(7-nitrobenz-2-oxa-1,3-diazol-4-yl)amino]-2-deoxy-D-glucose (2-NBDG) in Muscle-Chips.

The Inventors anticipate that insulin mediated glucose uptake is increased by both vascular endothelium and innervation. In contrast, the Inventors anticipate that insulin mediated glucose uptake is minimal in i-SkM from monogenetic loss of function insulin receptor mutants but restored when the gene is repaired in iPSC clones by CRISPR before differentiation.

Example 10

Fully Integrated Chips with Immune Components to Mimic Bimodal System Relevant to Diabetes For establishing the bimodal system relevant for diabetes, the Inventors investigate the islet and muscle chips separately. The Inventors will start with the premise that the iPSC derived islets and muscle from β-T2D and IR-T2D are more vulnerable to disease inducing strategies (chronic stimulation/inflammatory cells for islets and inflammatory cells, innervation density and altered lipid profiles for skeletal muscle). Given that T2D is a disease of aging, and that generation of iPSCs may remove changes of aging, it is plausible that iPSC-derived tissues will not recapitulate disease states even when challenged as proposed. In that case alternative strategies are used by CRISPR technology to recapitulate β-cell dysfunction and skeletal muscle insulin resistance present n T2D.

Example 11

Model of β-Cell Dysfunction T2D in i-Islets

Initial studies using monogenetic diabetes sample will serve to optimize and validatethe i-Islet-on-chip in the UH3 phase. Subsequently, these platforms can be deployed in recruited patients with T2D whose underlying cause for loss of glucose homeostasis is predominantly insulin resistance (IR-T2D) versus those in who the predominant defect is a β-cell defect (β-T2D).

The extent of the defects of β-cell function and insulin resistance for each individual with T2D are evaluated using the Cobelli mixed meal minimal model approach as already used in the ongoing CIRM study. The most well defined risk factor for β-cell failure in T2D is chronic β-cell stimulation. To mimic this i-Islets from each group (β-T2D, IR-T2D and non-diabetic controls) are perfused with a glucose of 6.6 mM (120 mg/dl) for 5 days before study. If i-Islets retain the predisposition of the individuals from who they were developed, the Inventors hypothesize that β-cell dysfunction will develop first in i-Islets differentiated from β-T2D, then IR-T2D and if at all last from non-diabetic controls. Since the underlying cause of β-cell failure is unknown, it is envisaged that additional strategies may need to be undertaken to induce β-cell dysfunction that recapitulates T2D in i-Islets. Strategies that would be rationale would be to expose the i-Isets to a higher glucose concentration ~11 mM, (200 mg/dl) for 5 days to induce glucotoxicity, increased lipids (lipotoxicity), add immune cells harvested from the patients with β-T2D, cytokines known to be enhanced in T2D and potentially combinations of these putative causes of β-cell failure in T2D. Another rationale strategies would be expose i-Islets to altered lipid soluble persistent organic pesticides that have been associated with T2D risk. If none of these strategies was effective, then it may be necessary to use a CRISR approach that recapitulates β-cell failure in T2D. An example might include ATG7 to include the autophagy pathway.

Example 12

Model of Insulin Resistance i-SkM

In common with β-cell dysfunction in T2D, the mechanism underpinning insulin resistance in T2D is controversial with a variety of interrelated hypothesis including immune cell mediated through cytokines released by type 1 macrophages, excess intramuscular lipids or a deficiency of a lipid class termed fatty acid esters of hydroxy fatty acids. Recently density of motor neuron neuromuscular junctions has been implicated in age related insulin resistance, and paraplegia is associated with an increased risk for T2D mediated through insulin resistance. Further studies can involve initially exposing i-SkM-on-chip to circulating immune cells harvested from patients with IR-T2D.

Example 13

Investigating Models of β-Cell Dysfunction and Insulin Resistance

The above compositions and methods allow for MPS models of both T2D with primary β-cell failure and T2D with predominant insulin resistance to gain insights into mechanisms of β-cell failure and insulin resistance respectively. Subsequently, these platforms allowing testing of available diabetes drugs and apply chemicals screens for efficacy in restoring β-cell function and insulin sensitivity in these MPS models of T2D, individually and then linked in series.

Without being bound by any particular theory, it is suggested that chronic stimulation (pre-diabetes [glucose] perfusion of i-Islet-Chips from β-T2D will result in β-cell dysfunction responsive to sulfonylurea and GLP-1. Further, addition of IR-T2D patient specific immune cells to i-SkM-Chips will cause muscle insulin resistance responsive to PPAR-γ agonists.

Example 14 iPSC Lines from Patients with Monogenic Mutations Leading to Neonatal Diabetes Mellitus or Impaired Insulin Action in Skeletal Muscle Using the described platforms, one can generate iPSC lines from patients with monogenic mutations leading to neonatal diabetes mellitus (KCNJ11) or impaired insulin action in skeletal muscle (Insulin receptor (INSR), TBC1D4), and create CRISPR-corrected isogenic controls. This includes clinical phenotyping, collection of blood samples from diseased patients and generation of iPSCs. Generation, characterization and banking of KCNJ11 and INSR patient iPSCs. CRISPR correction to make isogenic mutation-corrected controls of n=2 donors/group. Positive control monogenic iPSC models of Islet dysfunction and All iPSC lines are generated in the same fashion from whole blood (PBMCs) as the lean T2D iPSCs that are currently generated and fully characterized in the clinical CIRM grant. If a line does not pass pluripotency testing and karyotyping, it is discarded and replaced by an additional line.

Additionally, robust differentiation of iPSC-derived islets (i-Islets) and i-Skeletal muscle (i-SkM) from a single healthy non-diabetic control single isogenic line on organ-chips. One can establish robust differentiation parameters, extracellular matrix (ECM) substrates and co-culture with endothelial cells for i-Islet and i-SkM differentiation in MPS for 14 days across replicate chips. Analysis can include evaluation of cell survival of i-Islets and i-SkM on organ-chips. Seeding is tested with different crosslinking substrates in conjugation with ECM components such as laminin, collagen type 1-V, fibronectin, vitronectin, entactin, and Matrigel™. Quantification of cell attachment, seeding density, longevity on chips, and various cell populations are conducted across 10 replicate chips and coefficient of variance (CV) of cell populations <20% for milestone completion. Innervated i-SkM+i-MN chip will have functional NMJs. Here it is suggested that the enhancement of islet and muscle function and maturation as a function of ECM and innervation is well documented, as well as evidence from the Inventors' preliminary data suggest Matrigel (laminin, collagen and entactin). The Inventors have begun these tests and observed functional improvement in cadaveric human islets on Matrigel-coated organ-chip. The Inventors have extensive experience differentiating i-Islets in bioreactors of different sizes iSkM with the Inventors' collaborator. If the Inventors observe that the exclusion of certain of specific ECM component enhances the Inventors' ability to meet this criterion, the Inventors will omit them from the model moving forward. As the Inventors have shown previously, the both i-Islets and i-SkM are capable of functioning with Matrigel and would still allow further disease discovery if cultured without supportive cell types. Matrigel composition is variable from batch-to-batch and preferably a defined human recombinant ECM will be identified for i-Islets and i-SkM on the chips.

Example 15

Parameters of i-Islets and i-SkM Inclusion with Endothelial Cells in Organ-Chips Here the aim is to verify i-Islet and i-SkM survival and long-term stability using co-culture with endothelial cells. This can be pursued by successfully co-culturing i-Islet and i-SkM chips with iPSC-derived endothelial cells or primary HUVECs are determined by immunostaining and confocal microscopy for cell health. Cell populations are quantified across 10 replicate chips with CV<20% after 14-30 days on chips. Media flow rate will also be varied between 15-100 μl/hr. iPSC-derived endothelial cells (iBMECs: Claudin-5$^+$ Occludin$^+$Glut-1$^+$; pan-endothelial: CD31$^+$CD144$^+$, Tie1$^+$) or primary HUVECs must be intact for successful endpoint. To assess impact of vascular interaction, transcriptomic profiles for functional maturation of i-Islets and i-SkM are performed using bulk and single cell-mRNA seq on sorted cells isolated from the chip. It is suggested that the enhancement of islet and skeletal muscle function and maturation through the co-culture with endothelial cells is well documented. The Inventors have begun these tests and expect to see functional improvement in islet function. If the Inventors observe that the addition of either endothelial cell type obstructs the Inventors' ability to meet this criterion, the Inventors will omit them from the model moving forward. As the Inventors have shown previously, both islets and skeletal muscle are capable of functioning without the addition of endothelium.

Example 16

Inter-Run and Inter-Line Stability of i-Islet and i-SkM Function Enhancement

Of additional interest is measuring i-Islet and iSkM function by GSIS (i-Islet), IMGU (i-SkM), mitochondrial and Ca' function, cell survival, myofiber fusion/contraction, immunostaining, and comparative transcriptomic analysis. Towards this aim, one can verify that potential biomarkers seen in of i-Islets and i-SkM organ-chips are enhanced by endothelial cells and provide a reproducible model.

CV<25% in between runs for an iPSC line and also between inter-iPSC lines for cell survival, GSIS for i-Islet chip and IMGU for i-SkM chip. Key secreted biomakers such as insulin, glucagon, and myokines (myostatin, BDNF, myonectin) need to be reproducible. Addition of sulfonylurea on mutant KCNJ11 i-Islets should result in insulin normalization.

It is suggested that the benefits of the addition of endothelium and the extent of Islet and SkM variation between experimental runs is unknown. Stability of the system as well as functional benefit of their inclusion moving forward must be established before completing OM4 Endothelial cells have also been implicated in diabetes. The organ-chip could therefore allow this cell type display novel biological and disease related physiology for the first time in vitro. Strict criteria for reproducibility of survival and function must be met to allow for subsequent analysis for disease specific phenotypes. If the addition of endothelial cells contributes too much variation in these critical biomarkers, they are removed and the simplified model of i-Islets or i-SkM only and stromal fibroblasts are used. If either secreted biomarker is not detectable, or is too variable, an alternate metabolite may be chosen as the standard for future assays.

Example 17

Generating iPSC Lines from Lean and Obese T2D Patients and Non-Diabetic Controls Additionally, of interest is collection of blood samples from diseased patients and generation of iPSCs. Lines are selected for congenital diabetes patients per clinical criteria. Towards this aim, one can generate and bank of 40 iPSC lines from lean (L-T2D) and obese (O-T2D) T2Ds, lean (L-ND) and obese (0-ND) non-diabetics (n=10/group). Isolate macrophages from PBMCs. This will allow establishing disease models from T2D patient iPSCs on organ-chips after validation the MPS platform with monogenic forms of diseased iPSCs. To apply MPS models of both T2D with primary β-cell failure and T2D with predominant insulin resistance to gain insights into mechanisms of β-cell failure and insulin resistance, respectively.

Example 18

Integrate the i-Islet and i-SkM Organ-Chips with Inflammatory Cells

Of interest is understand whether the i-Islet and i-SkM organ-chips from above groups are linked in series with and without inflammatory cells and impact of β-cell (sulfonylureas, GLP-1) and muscle (PPAR-γ agonists) drugs evaluated. Towards these aims, one can conduct chronic stimulation i-Islets on chips from β-T2D will result in β-cell dysfunction responsive to sulfonylurea and GLP-1. Addition of IR-T2D patient specific immune cells to i-SkM on chip will cause muscle insulin resistance responsive to PPAR-γ agonists.

To test GSIS and IMGU responses when exposed to isogenic and patient acquired immune cells from individuals who successfully adapt to insulin resistance (obese nondiabetic) and those who develop T2D in response to obesity (IR-T2D). Evaluate available diabetes drugs and apply chemicals screens for efficacy in restoring β-cell function and insulin sensitivity in these two MPS models of T2D.

Example 19

Establish Disease-Specific Phenotypes in T2D Patient Organ-Chips

The aforementioned methods and compositions support developed of a set of reliable disease specific biomarkers that distinguish T2D from control lines and each other. Each biomarker must be significantly increased or decreased (P<0.05). To achieve this aim, disease-specific biomarkers are identified by comparing to ND controls using secretome (proteomics) and metabolomics. Overall culture health is determined by LDH assay and used as a biomarker if activity is significantly increased P<0.05 over control. % survival and function of i-Islets is assessed using immunostaining of: c-peptide$^+$, glucagon$^+$, Nkx6.1$^+$, Pdx1$^+$, chromogranin A (CHGA)$^+$, and i-SkM are assessed by Pax3/Pax7, MyoD1, MyoG, MHC, Desmin, Mf20. Gene pathway expression analysis is compared to non-diabetic controls. Significantly increased/reduced signatures will be complemented by proteomic analysis for biomarker confirmation. Significant disease biomarkers (P<0.05) are included in a list ranked by CV. If one diseased line does not reproduce disease phenotypes it will be considered an outlier, and phenotype is further characterized using additional lines.

It is suggested that the comprehensive panel of described functional assays will be effective in use for T2D disease-specific phenotype discovery. Changes in secreted proteins, metabolites, gene expression, and mitochondrial function associated with cell death are used as a positive control. The generation of robust disease associated phenotypes from T2D, the genesis of which is unknown, may not necessitate cell death to yield impactful biomarkers.

Thereafter, one will confirm that biomarkers are present in lean and obese T2D iPSC lines using specific analysis for those markers when compared to the non-diabetic control iPSC lines. Inconsistent biomarkers are eliminated from the panel. >5 biomarkers must be significantly different between disease and control P<0.05 and present in at least 5/8 individual patient iPSCs. Full literature search is conducted and results of biomarker comparison to clinical data will be included in a published report to be circulated among clinicians.

Due to the sporadic nature of T2D diseased iPSC lines, the Inventors cannot expect that each line will behave identically. The approach, however, is to study common phenotypes that are shared amongst the patient population. Therefore, common and highly reproducible phenotypes will be given priority. If strong phenotypes are discovered in a subpopulation of lines, more traditional forms of pathological studies will be conducted on these lines and traced back to clinical data. Known biomarkers in clinic will help validate approach and relevance to MPS-derived biomarkers. Novel proteomic, metabolomic and functional phenotypes may be determined by retrospective or prospective analysis of clinical patient samples such as serum, or tissue.

Example 20

Screening Putative Drug Candidates on Organ-Chips for Insulin Normalization in T2D iPSCs The aforementioned methods and compositions support evaluation of available diabetes drugs and apply chemical screens for efficacy in restoring β-cell function and insulin sensitivity in these two MPS models of T2D, added through endothelial channel of the organ-chips.

For example, one can conduct 384-well cytotoxicity screening of available diabetes drugs using compound libraries. Primary screen leading to insulin normalization with generation of ranked list of drug candidates. Conduct dose response experiments for selection of 3 phenotype reversing drug candidates. A major utility of the MPS system is to assess the discovery of compounds into endothelial side of channel. To accelerate the application of novel drug candidates into the clinic, screening will concentrate on drugs that penetrate the endothelial cell layer of the chips, into the i-Islet and i-SkM compartment. In addition to yielding potential drug candidates, novel permeability data will be generated on the NCATS Small molecule library that will aid other diabetes research efforts. If no drugs reverse biomarkers, non-endothelial permeable drugs will be tested on the i-Islet or i-SkM channel directly.

Example 21

Generation of iPSC-Derived Pancreatic Islets

Whereas the earlier described preliminary establish a platform for modeling diabetes, significant improvements can exist in improving efficient yield of differentiated cells and properties of such differentiated cells. In particular, deriving functionally mature pancreatic endocrine cells from iPSCs for use in disease modeling, drug testing, and transplantation therapies to study diabetes remains an important goal.

Towards this end, endocrine development undergoes many critical stages to generate a desired population. Existing protocols suffer in particular from inefficiency of differentiation during early stages. Such inefficiency can give rise to a mix population of unwanted cell types that will drastically reduce end stage efficiency. In disease modeling, the presence of heterogenous cells types can also affect readout by contrubting noise. Thus, there is a great need for a robust differentiation protocol, with emphasis on improving differentiation steps during early stages.

To optimize early stages of differentiation, the Inventor tested several combinations of differentiation growth factors and agents. Testing protocols allowed robust differentiation of PDX1/NKX6.1 endocrine progenitors in 13 days from iPSCs with >90% Efficiency. This is a significant improvement over any comparable protocol. In support of efficient differentiation, very high seeding density appears to support high efficiency of differentiation towards endocrine progenitors.

Example 22

Differentiation of Endocrine Progenitors Towards Beta Cells

To further differentiate endocrine progenitors into beta cells, various reagents were tested to determine which combinations are most efficient in generating immature beta cells. T3 was selected for its role in beta cell survival, function, and identity Alk5 inhibitor II was selected for its specificity in inhibition of TGF beta receptor 1. XXI was selected as Notch inhibitor to exit cell cycle and as a driving force between endocrine vs duct phenotypes. Noggin is selected for BMP inhibition due to evidence that inhibition of this pathway is important for endocrine differentiation. Addition of notch inhibitor XXI reduced NKX6.1 levels and increased glucagon levels. Addition of noggin slightly increases c-peptide levels. GSIS results show cells do not secrete insulin in response to glucose. The aforementioned growth factors can be used in combination for immature beta cell production. Thereafter, there is a need for a maturation step to induce glucose sensitivity on immature induced-islet cells Example 23

Maturation of Induced Islets to Secrete Insulin in Response to Glucose

To gain insulin responsiveness, the induction of the transcription factor MafA was identified as an important factor. The Inventors discovered that inhibiting the Axl pathway and adding antioxidants could induce and maintain MafA expression.

Towards this end, R428 is tested as an Axl inhibitor and N-Acetyl-Cysteine (NAC) is used as antioxidant. MafA appears to localize in the cytoplasm. This is known to be a response to oxidative stress. GSIS shows high concentration of insulin in media before being fed to cells and cells show low basal insulin secretion in culture. Insulin is a stimulator of oxidative phosphorylation. High ox-phos rates due to high insulin concentration in the media could result in high levels of free radicals that cause MafA to localize in the cytoplasm and reduce glucose sensitivity. Based on the last results, the Inventors plan to test removal of insulin from the media as an attempt to induce endogenous insulin secretion when cells are challenged to a high glucose test. Without being bound by any particular theory, it appears that high glucose levels are required to activate MafA. Thus, the Inventors also plan to test modulating glucose levels during the maturation stage of our protocol.

Example 34 iPSC-Derived Endothelial Cells

The earlier preliminary studies relied on available HUVEC and iBMEC cells. While initial studies demonstrate the cross-talk between endothelial cells and endocrine cells, it is of interest to develop a faithful model of metabolic diseases, such as diabetes by generating more physiologically relevant endothelial cell types. Towards this end, the Inventors developed a "pan endothelial" cell type, expressing key markers such as CD31, CD34, VEGF, and VEGFA. Using a combination of growth factors, the Inventors were able to successfully produce endothelial cell types. Based on the described protocols, it appears that endothelial markers are more and purely expressed in Day 20 compared to Day 10 of differentiation→time for maturation. Differentiation to be confirmed with other experiments: Dil-ac-LDL uptake, and TEER (resistance).

Example 25

Co-Culture of iPSC-Derived Islets (i-Islets) with Endothelial Cells

After producing the aforementioned cell populations using the described protocols, the Inventors co-cultured i-Islets with i-Endo cells in transwell plates. This began by introducing i-Endo cells during differentiation of iPSCs into pancreatic progenitors and maturation of i-Islets phases, followed by verifying improvement of i-Islets differentiation and function. In a first 1st co-culture experiment with HUVECs in transwells (polyester-PET), HUVECs were placed on bottom with i-Islets on PET inserts; HUVECs introduced on Stage 1 of i-Islets differentiation.

Example 26

Co-Culture with HUVECs in Transwells (PET): Main Conclusions i-Islets appear do not adapt well to be cultured on the PET inserts (top). Co-culture of i-Islets with HUVECS endothelial cells seem to be beneficial to the endothelial cells in terms of CD31 expression levels. This could be due to some signal exchange between i-Islets and HUVECs in the conditioned media i-Islets do not differentiate well to endocrine fate with HUVECs. This is likely because the majority of the media observed by the i-Islets is the HUVECs media. Co-culture started to early in i-islet fate specification. In an alternative embodiment, one can change the format for i-Islets to be cultured on the bottom Example 27

Co-Culture with HUVECs in Transwells (PET)

In addition studies, the Inventors placed HUVECs on PET inserts. i-Islets on bottom (SLiP media). HUVECs introduced on Stage 6 of i-Islets differentiation (maturation of islets). Test media in which the HUVECs are cultured 2nd co-culture experiment with HUVECs in transwells (PET): main conclusions i-Islets cultured on the bottom appear to be better compared to culture on the inserts. Co-culture of i-Islets with endothelial cells appear to improve the differentiation of islets, especially when endothelial cells are culture with its own media→to be confirmed by upcoming experiments where we will try to reproduce these results using HUVECs or i-Endothelial cells.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to induced pluripotent stem cells (iPSCs), differentiated iPSCs including definitive endoderm, progenitor cells, islet cells, mesoderm, progenitor cells, vascular cells including brain microvasciular endothelial cells, methods and compositions related to use of the aforementioned compositions, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating pancreatic progenitor cells, comprising:
    culturing induced pluripotent stem cells (iPSCs) in the presence of Activin A and CHIR99021 for about 3 days to generate definitive endoderm;
    culturing definitive endoderm in the presence of FGF10, Noggin, and CHIR 99021 for about 2 days to generate gut tube endothelium; and
    culturing gut tube endothelium in the presence of FGF10, Noggin, Sant1, and retinoic acid for about 4 days to generate pancreatic progenitor cells.

2. The method of claim 1, wherein the pancreatic progenitor cells express PDX1, NKX6.1, or both.

3. The method of claim 1, further comprising culturing pancreatic progenitor cells in the presence of EGF, nicotinamide, and Noggin for about 4 days to generate endocrine progenitor cells.

4. The method of claim 3, further comprising culturing endocrine progenitor cells in the presence of triiodothyronine (T3), TGFβ type I receptor (ALK5) kinase inhibitor (Alk5i), and Noggin for about 7 days to generate immature endocrine cells expressing NKX6.1 and one or both of C-peptide and glucagon.

5. The method of claim 1, wherein the definitive endoderm express CXCR, SOX17, or both CXCR and SOX17.

6. The method of claim 4, further comprising culturing immature endocrine cells in the presence of T3, Alk5i, R428 and N-Acetyl-Cysteine (NAC) for about 7 days to generate mature endocrine cells expressing MafA and one or both of C-peptide and glucagon.

7. The method of claim 6, wherein the mature endocrine cells express C-peptide, glucagon, and MafA.

8. The method of claim 4, wherein the immature endocrine cells are islet cells.

9. The method of claim 6, wherein the mature endocrine cells are islet cells.

10. The method of claim 8, wherein the islet cells are beta islet cells.

11. The method of claim 9, wherein the islet cells are beta islet cells.

12. The method of claim 9, wherein the islet cells are capable of producing insulin.

13. The method of claim 9, wherein the islet cells secrete insulin.

14. The method of claim 9, wherein the islet cells are glucose responsive.

15. The method of claim 1, wherein the iPSCs are derived from a diabetic subject.

* * * * *